(12) United States Patent
Lin et al.

(10) Patent No.: US 9,606,100 B2
(45) Date of Patent: Mar. 28, 2017

(54) FLUORESCENT PROTEIN VOLTAGE SENSORS FOR MEASURING MEMBRANE POTENTIAL AND IMAGING HIGH-FREQUENCY NEURONAL ELECTRICAL ACTIVITY

(71) Applicants: Michael Z. Lin, Stanford, CA (US); Francois St-Pierre, Stanford, CA (US)

(72) Inventors: Michael Z. Lin, Stanford, CA (US); Francois St-Pierre, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 73 days.

(21) Appl. No.: 14/537,663

(22) Filed: Nov. 10, 2014

(65) Prior Publication Data
US 2015/0132774 A1    May 14, 2015

Related U.S. Application Data

(60) Provisional application No. 61/902,265, filed on Nov. 10, 2013.

(51) Int. Cl.
| | | |
|---|---|---|
| C12N 15/00 | (2006.01) | |
| G01N 33/483 | (2006.01) | |
| C07K 14/705 | (2006.01) | |
| C12N 9/16 | (2006.01) | |
| G01N 33/68 | (2006.01) | |
| G01N 33/50 | (2006.01) | |
| C07K 14/435 | (2006.01) | |

(52) U.S. Cl.
CPC ... *G01N 33/4833* (2013.01); *C07K 14/43595* (2013.01); *C07K 14/705* (2013.01); *C12N 9/16* (2013.01); *G01N 33/502* (2013.01); *G01N 33/6872* (2013.01); *C07K 2319/03* (2013.01); *C07K 2319/033* (2013.01); *C07K 2319/60* (2013.01); *C12Y 301/03* (2013.01); *G01N 2333/916* (2013.01); *G01N 2500/10* (2013.01)

(58) Field of Classification Search
None
See application file for complete search history.

(56) References Cited

U.S. PATENT DOCUMENTS 6,699,687 B1    3/2004    Tsien et al.
2013/0224756 A1    8/2013    Cohen et al.

FOREIGN PATENT DOCUMENTS

WO    2013052946 A9    4/2013

OTHER PUBLICATIONS

Jin et al., "Single Action Potentials and Subthreshold electrical events imaged in neurons with a fluorescent protein voltage probe", Neuron 75, 779-785 (2012).*
Lam et al., "Improving FRET dynamic range with bright green and red fluorescent proteins", Nature Methods vol. 9, No. 10, 1005-1017 (2012).*
Siegel and Isacoff, "A Genetically Encoded Optical Probe of Membrane Voltage", Neuron 19, 735-741 (1997).*
Chen et al. (2013) Ultrasensitive fluorescent proteins for imaging neuronal activity. Nature 499:295-300.
Kralj et al. (2012) Optical recording of action potentials in mammalian neurons using a microbial rhodopsin. Nat. Methods 9:90-95.
Gong et al. (2013) Enhanced Archaerhodopsin Fluorescent Protein Voltage Indicators. PLoS One 8:e66959.
Lundby et al. (2008) Engineering of a genetically encodable fluorescent voltage sensor exploiting fast Ci-VSP voltage-sensing movements. PLoS One 3:e2514.
Jin et al. (2012) Single action potentials and subthreshold electrical events imaged in neurons with a fluorescent protein voltage probe. Neuron 75:779-785.
Kurokawa et al. (2012) 3' Phosphatase activity toward phosphatidylinositol 3,4-bisphosphate [PI(3,4)P2] by voltage-sensing phosphatase (VSP). Proc. Natl. Acad. Sci. U.S.A. 109:10089-10094.
Dimitrov et al. (2007) Engineering and characterization of an enhanced fluorescent protein voltage sensor. PLoS One 2:e440.
Pedelacq et al. (2006) Engineering and characterization of a superfolder green fluorescent protein. Nat. Biotechnol. 24:79-88.
Akerboom et al. (2012) Optimization of a GCaMP calcium indicator for neural activity imaging. J. Neurosci. 32:13819-13840.
Akerboom et al. (2013) Genetically encoded calcium indicators for multi-color neural activity imaging and combination with optogenetics. Front. Mol. Neurosci 6:2.
Tian et al. (2009) Imaging neural activity in worms, flies and mice with improved GCaMP calcium indicators. Nat Methods 6:875-881.
Patti et al. (2013) Measuring membrane voltage with fluorescent proteins. Cold Spring Harb. Protoc. 2013 (7):606-613.
Barnett et al. (2012) A fluorescent, genetically-encoded voltage probe capable of resolving action potentials. PLoS One 7(9):e43454.
Zhao et al. (2011) An expanded palette of genetically encoded Ca2+ indicators. Science 333:1888-1891.

* cited by examiner

*Primary Examiner* — Anand Desai
(74) *Attorney, Agent, or Firm* — Jenny Buchbinder

(57) ABSTRACT

Fluorescent protein voltage sensors for measuring membrane potential and imaging high-frequency neuronal electrical activity are disclosed. In particular, the invention relates to engineered protein voltage sensors that comprise a voltage-sensing domain comprising four transmembrane domains linked to a circularly permuted fluorescent protein, which is inserted into the extracellular loop between the third (S3) and fourth (S4) transmembrane segments of the voltage-sensing domain. Such fluorescent protein voltage sensors can be used for measuring the electrical activity of neurons, including single action potentials, trains of action potentials, and subthreshold potential changes and, in particular, for imaging high-frequency neuronal electrical activity. Additionally, fluorescent protein voltage sensors can be used for a variety of other purposes, including measuring the membrane potential of any cell, including other excitable cells such as cardiac cells and endocrine cells, and for screening agents that target ion channels for their effects on membrane potential.

62 Claims, 34 Drawing Sheets

|  | | ASAP1 | ArcLight Q239 |
|---|---|---|---|
| activation | $\tau_1$ (ms) | 2.05 ± 0.18 | 11.8 ± 1.6 |
| activation | $\tau_2$ (ms) | 71.5 ± 1.6 | 91.3 ± 20.3 |
| activation | % fast | 60.2 ± 1.2 | 57.7 ± 4.9 |
| inactivat. | $\tau_1$ (ms) | 1.98 ± 0.08 | 31.4 ± 7.1 |
| inactivat. | $\tau_2$ (ms) | 50.8 ± 1.2 | 150 ± 26 |
| inactivat. | % fast | 43.7 ± 0.6 | 71.0 ± 1.6 |

FIG. 1E

SEQUENCE LISTING

```
<160> NUMBER OF SEQ ID NOS: 20

<210> SEQ ID NO 1
<211> LENGTH: 427
<212> TYPE: PRT
<213> ORGANISM: Artificial Sequence
<220> FEATURE:
<223> OTHER INFORMATION: ASAP1 (A148::cpGFP::T149)

<400> SEQUENCE: 1
```

-continued

```
Met Glu Thr Thr Val Arg Tyr Glu Gln Gly Ser Glu Leu Thr Lys Thr
1               5                   10                  15

Ser Ser Ser Pro Thr Ala Asp Glu Pro Thr Ile Lys Ile Asp Asp Gly
            20                  25                  30

Arg Asp Glu Gly Asn Glu Gln Asp Ser Cys Ser Asn Thr Ile Arg Arg
        35                  40                  45

Lys Ile Ser Pro Phe Val Met Ser Phe Gly Phe Arg Val Phe Gly Val
50                  55                  60

Val Leu Ile Ile Val Asp Ile Ile Val Ile Val Asp Leu Ala Ile
65                  70                  75                  80

Ser Glu Lys Lys Arg Gly Ile Arg Glu Ile Leu Glu Gly Val Ser Leu
                85                  90                  95

Ala Ile Ala Leu Phe Phe Leu Val Asp Val Leu Met Arg Val Phe Val
                100                 105                 110

Glu Gly Phe Lys Asn Tyr Phe Arg Ser Lys Leu Asn Thr Leu Asp Ala
            115                 120                 125

Val Ile Val Val Gly Thr Leu Leu Ile Asn Met Thr Tyr Ser Phe Ser
        130                 135                 140

Asp Leu Ala Ala Phe Asn Ser His Asn Val Tyr Ile Thr Ala Asp Lys
145                 150                 155                 160

Gln Lys Asn Gly Ile Lys Ala Asn Phe Thr Val Arg His Asn Val Glu
                165                 170                 175

Asp Gly Ser Val Gln Leu Ala Asp His Tyr Gln Gln Asn Thr Pro Ile
                180                 185                 190

Gly Asp Gly Pro Val Leu Leu Pro Asp Asn His Tyr Leu Ser Thr Gln
            195                 200                 205

Thr Val Leu Ser Lys Asp Pro Asn Glu Lys Arg Asp His Met Val Leu
        210                 215                 220

Leu Glu Phe Val Thr Ala Ala Gly Ile Thr His Gly Met Asp Glu Leu
225                 230                 235                 240

Tyr Gly Gly Thr Gly Gly Ser Ala Ser Gln Gly Glu Glu Leu Phe Thr
                245                 250                 255

Gly Val Val Pro Ile Leu Val Glu Leu Asp Gly Asp Val Asn Gly His
                260                 265                 270

Lys Phe Ser Val Arg Gly Glu Gly Glu Gly Asp Ala Thr Ile Gly Lys
            275                 280                 285

Leu Thr Leu Lys Phe Ile Cys Thr Thr Gly Lys Leu Pro Val Pro Trp
        290                 295                 300

Pro Thr Leu Val Thr Thr Leu Thr Tyr Gly Val Gln Cys Phe Ser Arg
305                 310                 315                 320

Tyr Pro Asp His Met Lys Arg His Asp Phe Phe Lys Ser Ala Met Pro
                325                 330                 335

Glu Gly Tyr Val Gln Glu Arg Thr Ile Ser Phe Lys Asp Asp Gly Lys
            340                 345                 350

Tyr Lys Thr Arg Ala Val Val Lys Phe Glu Gly Asp Thr Leu Val Asn
        355                 360                 365

Arg Ile Glu Leu Lys Gly Thr Asp Phe Lys Glu Asp Gly Asn Ile Leu
    370                 375                 380

Gly His Lys Leu Glu Tyr Asn Thr Asp Gln Met Pro Gln Met Val Thr
385                 390                 395                 400

Leu Leu Arg Val Leu Arg Ile Val Ile Leu Ile Arg Ile Phe Arg Leu
                405                 410                 415
```

Ala Ser Gln Lys Lys Gln Leu Glu Val Val Thr
            420                 425

<210> SEQ ID NO 2
<211> LENGTH: 427
<212> TYPE: PRT
<213> ORGANISM: Artificial Sequence
<220> FEATURE:
<223> OTHER INFORMATION: ASAP1 (A147::cpGFP::A148)

<400> SEQUENCE: 2

Met Glu Thr Thr Val Arg Tyr Glu Gln Gly Ser Glu Leu Thr Lys Thr
1               5                   10                  15

Ser Ser Ser Pro Thr Ala Asp Glu Pro Thr Ile Lys Ile Asp Asp Gly
            20                  25                  30

Arg Asp Glu Gly Asn Glu Gln Asp Ser Cys Ser Asn Thr Ile Arg Arg
        35                  40                  45

Lys Ile Ser Pro Phe Val Met Ser Phe Gly Phe Arg Val Phe Gly Val
    50                  55                  60

Val Leu Ile Ile Val Asp Ile Ile Val Val Ile Val Asp Leu Ala Ile
65                  70                  75                  80

Ser Glu Lys Lys Arg Gly Ile Arg Glu Ile Leu Glu Gly Val Ser Leu
                85                  90                  95

Ala Ile Ala Leu Phe Phe Leu Val Asp Val Leu Met Arg Val Phe Val
            100                 105                 110

Glu Gly Phe Lys Asn Tyr Phe Arg Ser Lys Leu Asn Thr Leu Asp Ala
        115                 120                 125

Val Ile Val Val Gly Thr Leu Leu Ile Asn Met Thr Tyr Ser Phe Ser
    130                 135                 140

Asp Leu Ala Phe Asn Ser His Asn Val Tyr Ile Thr Ala Asp Lys Gln
145                 150                 155                 160

Lys Asn Gly Ile Lys Ala Asn Phe Thr Val Arg His Asn Val Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Thr
        195                 200                 205

Val Leu Ser Lys Asp Pro Asn Glu Lys Arg Asp His Met Val Leu Leu
    210                 215                 220

Glu Phe Val Thr Ala Ala Gly Ile Thr His Gly Met Asp Glu Leu Tyr
225                 230                 235                 240

Gly Gly Thr Gly Gly Ser Ala Ser Gln Gly Glu Glu Leu Phe Thr Gly
                245                 250                 255

Val Val Pro Ile Leu Val Glu Leu Asp Gly Asp Val Asn Gly His Lys
            260                 265                 270

Phe Ser Val Arg Gly Glu Gly Glu Gly Asp Ala Thr Ile Gly Lys Leu
        275                 280                 285

Thr Leu Lys Phe Ile Cys Thr Thr Gly Lys Leu Pro Val Pro Trp Pro
    290                 295                 300

Thr Leu Val Thr Thr Leu Thr Tyr Gly Val Gln Cys Phe Ser Arg Tyr
305                 310                 315                 320

Pro Asp His Met Lys Arg His Asp Phe Phe Lys Ser Ala Met Pro Glu
                325                 330                 335

Gly Tyr Val Gln Glu Arg Thr Ile Ser Phe Lys Asp Asp Gly Lys Tyr
            340                 345                 350

-continued

```
Lys Thr Arg Ala Val Val Lys Phe Glu Gly Asp Thr Leu Val Asn Arg
                355                 360                 365
Ile Glu Leu Lys Gly Thr Asp Phe Lys Glu Asp Gly Asn Ile Leu Gly
    370                 375                 380
His Lys Leu Glu Tyr Asn Ala Thr Asp Gln Met Pro Gln Met Val Thr
385                 390                 395                 400
Leu Leu Arg Val Leu Arg Ile Val Ile Leu Ile Arg Ile Phe Arg Leu
                405                 410                 415
Ala Ser Gln Lys Lys Gln Leu Glu Val Val Thr
                420                 425

<210> SEQ ID NO 3
<211> LENGTH: 427
<212> TYPE: PRT
<213> ORGANISM: Artificial Sequence
<220> FEATURE:
<223> OTHER INFORMATION: ASAP1 (T149::cpGFP::D150)

<400> SEQUENCE: 3

Met Glu Thr Thr Val Arg Tyr Glu Gln Gly Ser Glu Leu Thr Lys Thr
1               5                   10                  15
Ser Ser Ser Pro Thr Ala Asp Glu Pro Thr Ile Lys Ile Asp Asp Gly
                20                  25                  30
Arg Asp Glu Gly Asn Glu Gln Asp Ser Cys Ser Asn Thr Ile Arg Arg
            35                  40                  45
Lys Ile Ser Pro Phe Val Met Ser Phe Gly Phe Arg Val Phe Gly Val
        50                  55                  60
Val Leu Ile Ile Val Asp Ile Ile Val Val Ile Asp Leu Ala Ile
65                  70                  75                  80
Ser Glu Lys Lys Arg Gly Ile Arg Glu Ile Leu Glu Gly Val Ser Leu
                85                  90                  95
Ala Ile Ala Leu Phe Phe Leu Val Asp Val Leu Met Arg Val Phe Val
                100                 105                 110
Glu Gly Phe Lys Asn Tyr Phe Arg Ser Lys Leu Asn Thr Leu Asp Ala
            115                 120                 125
Val Ile Val Val Gly Thr Leu Leu Ile Asn Met Thr Tyr Ser Phe Ser
        130                 135                 140
Asp Leu Ala Ala Thr Phe Asn Ser His Asn Val Tyr Ile Thr Ala Asp
145                 150                 155                 160
Lys Gln Lys Asn Gly Ile Lys Ala Asn Phe Thr Val Arg His Asn Val
                165                 170                 175
Glu Asp Gly Ser Val Gln Leu Ala Asp His Tyr Gln Gln Asn Thr Pro
                180                 185                 190
Ile Gly Asp Gly Pro Val Leu Leu Pro Asp Asn His Tyr Leu Ser Thr
            195                 200                 205
Gln Thr Val Leu Ser Lys Asp Pro Asn Glu Lys Arg Asp His Met Val
        210                 215                 220
Leu Leu Glu Phe Val Thr Ala Ala Gly Ile Thr His Gly Met Asp Glu
225                 230                 235                 240
Leu Tyr Gly Gly Thr Gly Gly Ser Ala Ser Gln Gly Glu Glu Leu Phe
                245                 250                 255
Thr Gly Val Val Pro Ile Leu Val Glu Leu Asp Gly Asp Val Asn Gly
                260                 265                 270
His Lys Phe Ser Val Arg Gly Glu Gly Glu Gly Asp Ala Thr Ile Gly
            275                 280                 285
```

```
Lys Leu Thr Leu Lys Phe Ile Cys Thr Thr Gly Lys Leu Pro Val Pro
            290                 295                 300

Trp Pro Thr Leu Val Thr Thr Leu Thr Tyr Gly Val Gln Cys Phe Ser
305                 310                 315                 320

Arg Tyr Pro Asp His Met Lys Arg His Asp Phe Phe Lys Ser Ala Met
                325                 330                 335

Pro Glu Gly Tyr Val Gln Glu Arg Thr Ile Ser Phe Lys Asp Asp Gly
            340                 345                 350

Lys Tyr Lys Thr Arg Ala Val Val Lys Phe Glu Gly Asp Thr Leu Val
            355                 360                 365

Asn Arg Ile Glu Leu Lys Gly Thr Asp Phe Lys Glu Asp Gly Asn Ile
370                 375                 380

Leu Gly His Lys Leu Glu Tyr Asn Asp Gln Met Pro Gln Met Val Thr
385                 390                 395                 400

Leu Leu Arg Val Leu Arg Ile Val Ile Leu Ile Arg Ile Phe Arg Leu
                405                 410                 415

Ala Ser Gln Lys Lys Gln Leu Glu Val Val Thr
            420                 425

<210> SEQ ID NO 4
<211> LENGTH: 183
<212> TYPE: PRT
<213> ORGANISM: Gallus gallus

<400> SEQUENCE: 4

Met Glu Thr Thr Val Arg Tyr Glu Gln Gly Ser Glu Leu Thr Lys Thr
1               5                   10                  15

Ser Ser Ser Pro Thr Ala Asp Glu Pro Thr Ile Lys Ile Asp Asp Gly
            20                  25                  30

Arg Asp Glu Gly Asn Glu Gln Asp Ser Cys Ser Asn Thr Ile Arg Arg
        35                  40                  45

Lys Ile Ser Pro Phe Val Met Ser Phe Gly Phe Arg Val Phe Gly Val
    50                  55                  60

Val Leu Ile Ile Val Asp Ile Val Val Ile Val Asp Leu Ala Ile
65                  70                  75                  80

Ser Glu Lys Lys Arg Gly Ile Arg Glu Ile Leu Glu Gly Val Ser Leu
                85                  90                  95

Ala Ile Ala Leu Phe Phe Leu Val Asp Val Leu Met Arg Val Phe Val
            100                 105                 110

Glu Gly Phe Lys Asn Tyr Phe Arg Ser Lys Leu Asn Thr Leu Asp Ala
        115                 120                 125

Val Ile Val Val Gly Thr Leu Leu Ile Asn Met Thr Tyr Ser Phe Ser
    130                 135                 140

Asp Leu Ala Ala Asp Gln Met Pro Gln Met Val Thr Leu Leu Arg Val
145                 150                 155                 160

Leu Arg Ile Val Ile Leu Ile Arg Ile Phe Arg Leu Ala Ser Gln Lys
                165                 170                 175

Lys Gln Leu Glu Val Val Thr
            180

<210> SEQ ID NO 5
<211> LENGTH: 244
<212> TYPE: PRT
<213> ORGANISM: Artificial Sequence
<220> FEATURE:
<223> OTHER INFORMATION: circularly permuted green fluorescent protein
      (cpGFP)
```

<400> SEQUENCE: 5

Phe Asn Ser His Asn Val Tyr Ile Thr Ala Asp Lys Gln Lys Asn Gly
1               5                   10                  15

Ile Lys Ala Asn Phe Thr Val Arg His Asn Val Glu Asp Gly Ser Val
            20                  25                  30

Gln Leu Ala Asp His Tyr Gln Gln Asn Thr Pro Ile Gly Asp Gly Pro
        35                  40                  45

Val Leu Leu Pro Asp Asn His Tyr Leu Ser Thr Gln Thr Val Leu Ser
    50                  55                  60

Lys Asp Pro Asn Glu Lys Arg Asp His Met Val Leu Leu Glu Phe Val
65                  70                  75                  80

Thr Ala Ala Gly Ile Thr His Gly Met Asp Glu Leu Tyr Gly Gly Thr
                85                  90                  95

Gly Gly Ser Ala Ser Gln Gly Glu Glu Leu Phe Thr Gly Val Val Pro
            100                 105                 110

Ile Leu Val Glu Leu Asp Gly Asp Val Asn Gly His Lys Phe Ser Val
        115                 120                 125

Arg Gly Glu Gly Glu Gly Asp Ala Thr Ile Gly Lys Leu Thr Leu Lys
130                 135                 140

Phe Ile Cys Thr Thr Gly Lys Leu Pro Val Pro Trp Pro Thr Leu Val
145                 150                 155                 160

Thr Thr Leu Thr Tyr Gly Val Gln Cys Phe Ser Arg Tyr Pro Asp His
                165                 170                 175

Met Lys Arg His Asp Phe Phe Lys Ser Ala Met Pro Glu Gly Tyr Val
            180                 185                 190

Gln Glu Arg Thr Ile Ser Phe Lys Asp Asp Gly Lys Tyr Lys Thr Arg
        195                 200                 205

Ala Val Val Lys Phe Glu Gly Asp Thr Leu Val Asn Arg Ile Glu Leu
    210                 215                 220

Lys Gly Thr Asp Phe Lys Glu Asp Gly Asn Ile Leu Gly His Lys Leu
225                 230                 235                 240

Glu Tyr Asn Thr

<210> SEQ ID NO 6
<211> LENGTH: 8
<212> TYPE: PRT
<213> ORGANISM: Artificial Sequence
<220> FEATURE:
<223> OTHER INFORMATION: plasma membrane targeting sequence

<400> SEQUENCE: 6

Gly Ser Ser Lys Ser Lys Pro Lys
1               5

<210> SEQ ID NO 7
<211> LENGTH: 4
<212> TYPE: PRT
<213> ORGANISM: Artificial Sequence
<220> FEATURE:
<223> OTHER INFORMATION: plasma membrane targeting sequence
<220> FEATURE:
<221> NAME/KEY: misc_feature
<222> LOCATION: (2)..(3)
<223> OTHER INFORMATION: Xaa can be any naturally occurring amino acid

<400> SEQUENCE: 7

Cys Xaa Xaa Leu
1

<210> SEQ ID NO 8
<211> LENGTH: 4
<212> TYPE: PRT
<213> ORGANISM: Artificial Sequence
<220> FEATURE:
<223> OTHER INFORMATION: plasma membrane targeting sequence
<220> FEATURE:
<221> NAME/KEY: MISC_FEATURE
<222> LOCATION: (2)..(3)
<223> OTHER INFORMATION: Xaa is an aliphatic amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 8

Cys Xaa Xaa Xaa
1

<210> SEQ ID NO 9
<211> LENGTH: 4
<212> TYPE: PRT
<213> ORGANISM: Artificial Sequence
<220> FEATURE:
<223> OTHER INFORMATION: plasma membrane targeting sequence
<220> FEATURE:
<221> NAME/KEY: misc_feature
<222> LOCATION: (3)..(4)
<223> OTHER INFORMATION: Xaa can be any naturally occurring amino acid

<400> SEQUENCE: 9

Cys Cys Xaa Xaa
1

<210> SEQ ID NO 10
<211> LENGTH: 26
<212> TYPE: PRT
<213> ORGANISM: Artificial Sequence
<220> FEATURE:
<223> OTHER INFORMATION: mitochondrial targeting sequence

<400> SEQUENCE: 10

Met Leu Arg Thr Ser Ser Leu Phe Thr Arg Arg Val Gln Pro Ser Leu
1               5                   10                  15

Phe Arg Asn Ile Leu Arg Leu Gln Ser Thr
            20                  25

<210> SEQ ID NO 11
<211> LENGTH: 4
<212> TYPE: PRT
<213> ORGANISM: Artificial Sequence
<220> FEATURE:
<223> OTHER INFORMATION: endoplasmic reticulum targeting sequence

<400> SEQUENCE: 11

Lys Asp Glu Leu
1

<210> SEQ ID NO 12
<211> LENGTH: 1281
<212> TYPE: DNA
<213> ORGANISM: Artificial Sequence
<220> FEATURE:
<223> OTHER INFORMATION: ASAP1

<400> SEQUENCE: 12
atggagacga ctgtgaggta tgaacagggg tcagagctca ctaaaacttc gagctctcca    60

```
acagcagatg agcccacgat aaagattgat gatggtcgtg atgagggtaa tgaacaagac    120
agctgttcca ataccattag gagaaaaatt tccccgtttg tgatgtcatt tggattcaga    180
gtatttggag ttgtgcttat cattgtagac atcatagtgg tgattgtgga tctggccatc    240
agtgagaaga aaagaggcat tagagagatt cttgaaggtg tttccctggc tatagcactc    300
ttcttccttg ttgatgttct catgagagtg tttgttgaag cttcaagaa ctatttccgg    360 tccaaactga atactttgga tgcagtcata gtagtgggca ctctgctaat taatatgacc    420
tactccttct ctgaccttgc tgcctttaac agccataacg tgtatattac cgcggataaa    480
cagaaaaacg gcattaaagc gaactttacc gtgcgccata acgtggaaga tggcagcgtg    540
cagctggcgg atcattatca gcagaacacc ccgattggcg atggcccggt gctgctgccg    600
gataaccatt atctgagcac ccagaccgtg ctgagcaaag atccgaacga aaacgcgat    660 cacatggtgc tgctggaatt tgtgaccgca gcgggcatta cacacggcat ggatgaactg    720
tatggcggca ccggcggcag cgcgagccag ggcgaagaac tgtttaccgg cgtggtgccg    780
attctggtgg aactggatgg cgatgtgaac ggccataaat ttagcgtgcg cggcgaaggc    840
gaaggcgatg cgaccattgg caaactgacc ctgaaattta tttgcaccac cggcaaacta    900
ccggtgccgt ggccgaccct ggtgaccacc ttaacctatg gcgtgcagtg ctttagccgc    960
tatccggatc atatgaaacg ccatgatttt tttaaaagcg cgatgccgga aggctatgtg   1020
caggaacgca ccattagctt taaagatgat ggcaaatata aaacccgcgc ggtggtgaaa   1080
tttgaaggcg atacccctggt gaaccgcatt gaactgaaag caccgatttt aaagaagat   1140 ggcaacattc tggggcataa actggaatat aacacagatc agatgccgca gatggttact   1200
cttcttcgag ttctgagaat tgttatctta ataagaatat tcgcctggc ttcacagaag   1260 aaacaacttg aagtggtaac c                                            1281
```

<210> SEQ ID NO 13
<211> LENGTH: 427
<212> TYPE: PRT
<213> ORGANISM: Artificial Sequence
<220> FEATURE:
<223> OTHER INFORMATION: Alligator mississippiensis ASAP variant

<400> SEQUENCE: 13

```
Met Glu Thr Thr Val Arg Tyr Glu Gln Gly Ser Glu Pro Pro Glu Val
1               5                   10                  15

Gln Asp Phe Glu Lys Pro Pro Glu Ala Ser Val Lys Ile Asp Asp Gly
            20                  25                  30

Arg Asp Glu Asp Gly Glu Pro Asp Ser Cys Ile Lys Asp Ile Lys Thr
        35                  40                  45

Gln Ile Ser Pro Phe Val Met Ser Phe Gly Phe Arg Val Phe Gly Ile
    50                  55                  60

Val Leu Ile Phe Val Asp Ile Ala Leu Leu Ile Val Asp Leu Ala Val
65                  70                  75                  80

Ser Asp Thr Gln Arg Asn Thr Lys Gln Thr Leu Glu Gly Val Ser Leu
                85                  90                  95

Gly Ile Ala Leu Phe Phe Phe Val Asp Val His Leu Arg Val Phe Val
            100                 105                 110

Glu Gly Phe Arg Thr Tyr Phe Arg Ser Lys Leu Asn Ile Leu Asp Ala
        115                 120                 125

Leu Ile Val Val Gly Thr Leu Leu Ile Asn Met Val Tyr Ser Phe Ser
    130                 135                 140
```

```
Gly Phe Ser Ala Phe Asn Ser His Asn Val Tyr Ile Thr Ala Asp Lys
145                 150                 155                 160

Gln Lys Asn Gly Ile Lys Ala Asn Phe Thr Val Arg His Asn Val Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
        195                 200                 205

Thr Val Leu Ser Lys Asp Pro Asn Glu Lys Arg Asp His Met Val Leu
    210                 215                 220

Leu Glu Phe Val Thr Ala Ala Gly Ile Thr His Gly Met Asp Glu Leu
225                 230                 235                 240

Tyr Gly Gly Thr Gly Gly Ser Ala Ser Gln Gly Glu Glu Leu Phe Thr
                245                 250                 255

Gly Val Val Pro Ile Leu Val Glu Leu Asp Gly Asp Val Asn Gly His
                260                 265                 270

Lys Phe Ser Val Arg Gly Glu Gly Glu Gly Asp Ala Thr Ile Gly Lys
            275                 280                 285

Leu Thr Leu Lys Phe Ile Cys Thr Thr Gly Lys Leu Pro Val Pro Trp
    290                 295                 300

Pro Thr Leu Val Thr Thr Leu Thr Tyr Gly Val Gln Cys Phe Ser Arg
305                 310                 315                 320

Tyr Pro Asp His Met Lys Arg His Asp Phe Phe Lys Ser Ala Met Pro
                325                 330                 335

Glu Gly Tyr Val Gln Glu Arg Thr Ile Ser Phe Lys Asp Asp Gly Lys
                340                 345                 350

Tyr Lys Thr Arg Ala Val Val Lys Phe Glu Gly Asp Thr Leu Val Asn
            355                 360                 365

Arg Ile Glu Leu Lys Gly Thr Asp Phe Lys Glu Asp Gly Asn Ile Leu
        370                 375                 380

Gly His Lys Leu Glu Tyr Asn Ala Asp Lys Ile Pro Gln Met Val Ile
385                 390                 395                 400

Phe Leu Arg Ala Leu Arg Ile Ile Ile Leu Ile Arg Ile Phe Arg Leu
                405                 410                 415

Ala Ser Gln Lys Lys Gln Leu Glu Lys Val Thr
            420                 425

<210> SEQ ID NO 14
<211> LENGTH: 426
<212> TYPE: PRT
<213> ORGANISM: Artificial Sequence
<220> FEATURE:
<223> OTHER INFORMATION: ASAP variant with cpmApple151-150

<400> SEQUENCE: 14

Met Glu Thr Thr Val Arg Tyr Glu Gln Gly Ser Glu Leu Thr Lys Thr
1               5                   10                  15

Ser Ser Ser Pro Thr Ala Asp Glu Pro Thr Ile Lys Ile Asp Asp Gly
                20                  25                  30

Arg Asp Glu Gly Asn Glu Gln Asp Ser Cys Ser Asn Thr Ile Arg Arg
            35                  40                  45

Lys Ile Ser Pro Phe Val Met Ser Phe Gly Phe Arg Val Phe Gly Val
        50                  55                  60

Val Leu Ile Ile Val Asp Ile Ile Val Val Ile Val Asp Leu Ala Ile
65                  70                  75                  80
```

Ser Glu Lys Lys Arg Gly Ile Arg Glu Ile Leu Gly Val Ser Leu
                85                  90                  95

Ala Ile Ala Leu Phe Phe Leu Val Asp Val Leu Met Arg Val Phe Val
            100                 105                 110

Glu Gly Phe Lys Asn Tyr Phe Arg Ser Lys Leu Asn Thr Leu Asp Ala
            115                 120                 125

Val Ile Val Gly Thr Leu Leu Ile Asn Met Thr Tyr Ser Phe Ser
130                 135                 140

Asp Leu Ala Ala Val Ser Glu Arg Met Tyr Pro Glu Asp Gly Ala Leu
145                 150                 155                 160

Lys Ser Glu Ile Lys Lys Gly Leu Arg Leu Lys Asp Gly Gly His Tyr
                165                 170                 175

Ala Ala Glu Val Lys Thr Thr Tyr Lys Ala Lys Lys Pro Val Gln Leu
            180                 185                 190

Pro Gly Ala Tyr Ile Val Asp Ile Lys Leu Asp Ile Val Ser His Asn
            195                 200                 205

Glu Asp Tyr Thr Ile Val Glu Gln Cys Glu Arg Ala Glu Gly Arg His
    210                 215                 220

Ser Thr Gly Gly Met Asp Glu Leu Tyr Lys Gly Gly Thr Gly Gly Ser
225                 230                 235                 240

Leu Val Ser Lys Gly Glu Glu Asp Asn Met Ala Ile Ile Lys Glu Phe
                245                 250                 255

Met Arg Phe Lys Val His Met Glu Gly Ser Val Asn Gly His Glu Phe
            260                 265                 270

Glu Ile Glu Gly Glu Gly Glu Gly Arg Pro Tyr Glu Ala Phe Gln Thr
            275                 280                 285

Ala Lys Leu Lys Val Thr Lys Gly Gly Pro Leu Pro Phe Ala Trp Asp
290                 295                 300

Ile Leu Ser Pro Gln Phe Met Tyr Gly Ser Lys Ala Tyr Ile Lys His
305                 310                 315                 320

Pro Ala Asp Ile Pro Asp Tyr Phe Lys Leu Ser Phe Pro Glu Gly Phe
                325                 330                 335

Arg Trp Glu Arg Val Met Asn Phe Glu Asp Gly Gly Ile Ile His Val
            340                 345                 350

Asn Gln Asp Ser Ser Leu Gln Asp Gly Val Phe Ile Tyr Lys Val Lys
            355                 360                 365

Leu Arg Gly Thr Asn Phe Pro Pro Asp Gly Pro Val Met Gln Lys Lys
370                 375                 380

Thr Met Gly Trp Glu Ala Thr Asp Gln Met Pro Gln Met Val Thr Leu
385                 390                 395                 400

Leu Arg Val Leu Arg Ile Val Ile Leu Ile Arg Ile Phe Arg Leu Ala
                405                 410                 415

Ser Gln Lys Lys Gln Leu Glu Val Val Thr
            420                 425

<210> SEQ ID NO 15
<211> LENGTH: 427
<212> TYPE: PRT
<213> ORGANISM: Artificial Sequence
<220> FEATURE:
<223> OTHER INFORMATION: Danio rerio ASAP variant

<400> SEQUENCE: 15

Met Glu Thr Ser Val His Phe Asn Pro Gly Leu Asp Ser Lys Glu Val
1               5                   10                  15

```
Asn Gly Asn Ser Val Lys Glu Ala Glu Val Gln Ile Asp Asp Gly
             20                  25                  30

Lys Glu Glu Thr Lys Asp Pro Asp Thr Met Tyr His Gln Val Arg Lys
         35                  40                  45

Lys Ile Thr Pro Phe Val Met Ser Phe Gly Phe Arg Val Phe Gly Leu
     50                  55                  60

Val Leu Ile Ile Leu Asp Ile Ile Met Val Ile Val Asp Leu Ser Leu
 65                  70                  75                  80

Ser Glu Lys Ser Arg Asp Val Gly Gly Ala Pro Glu Thr Val Ser Leu
                 85                  90                  95

Val Ile Ser Phe Phe Leu Ile Asp Val Leu Leu Arg Val Tyr Val
                100                 105                 110

Glu Gly Phe Lys Val Tyr Phe Ser Ser Lys Leu Asn Ile Val Asp Ala
             115                 120                 125

Cys Ile Val Val Ile Thr Leu Val Val Thr Met Ile Tyr Ala Phe Ser
130                 135                 140

Asp Phe Ser Gly Phe Asn Ser His Asn Val Tyr Ile Thr Ala Asp Lys
145                 150                 155                 160

Gln Lys Asn Gly Ile Lys Ala Asn Phe Thr Val Arg His Asn Val Glu
                165                 170                 175

Asp Gly Ser Val Gln Leu Ala Asp His Tyr Gln Gln Asn Thr Pro Ile
            180                 185                 190

Gly Asp Gly Pro Val Leu Leu Pro Asp Asn His Tyr Leu Ser Thr Gln
            195                 200                 205

Thr Val Leu Ser Lys Asp Pro Asn Glu Lys Arg Asp His Met Val Leu
        210                 215                 220

Leu Glu Phe Val Thr Ala Ala Gly Ile Thr His Gly Met Asp Glu Leu
225                 230                 235                 240

Tyr Gly Gly Thr Gly Gly Ser Ala Ser Gln Gly Glu Glu Leu Phe Thr
                245                 250                 255

Gly Val Val Pro Ile Leu Val Glu Leu Asp Gly Asp Val Asn Gly His
            260                 265                 270

Lys Phe Ser Val Arg Gly Glu Gly Glu Gly Asp Ala Thr Ile Gly Lys
        275                 280                 285

Leu Thr Leu Lys Phe Ile Cys Thr Thr Gly Lys Leu Pro Val Pro Trp
    290                 295                 300

Pro Thr Leu Val Thr Thr Leu Thr Tyr Gly Val Gln Cys Phe Ser Arg
305                 310                 315                 320

Tyr Pro Asp His Met Lys Arg His Asp Phe Phe Lys Ser Ala Met Pro
                325                 330                 335

Glu Gly Tyr Val Gln Glu Arg Thr Ile Ser Phe Lys Asp Asp Gly Lys
            340                 345                 350

Tyr Lys Thr Arg Ala Val Val Lys Phe Glu Gly Asp Thr Leu Val Asn
        355                 360                 365

Arg Ile Glu Leu Lys Gly Thr Asp Phe Lys Glu Asp Gly Asn Ile Leu
    370                 375                 380

Gly His Lys Leu Glu Tyr Asn Ala Ser Leu Ile Pro Gln Val Val Thr
385                 390                 395                 400

Phe Leu Arg Ser Leu Arg Ile Leu Ile Leu Val Arg Ile Phe Arg Leu
                405                 410                 415

Ala Ser Gln Lys Arg Glu Leu Glu Lys Val Thr
            420                 425
```

<210> SEQ ID NO 16
<211> LENGTH: 469
<212> TYPE: PRT
<213> ORGANISM: Artificial Sequence
<220> FEATURE:
<223> OTHER INFORMATION: Metaseiulus occidentalis ASAP variant

<400> SEQUENCE: 16

```
Met Glu Pro Ser Tyr Asp Arg Phe Asn Asn Asp Ser Asn Asn Val Ser
1               5                   10                  15

Ser Asn Asn Asp Ile Asn Asn Lys Arg Asn Arg Ala Gly Asn Asp Asp
            20                  25                  30

Ser Asp Asp His Thr Ala Gly Ser Asp Gly Gly Lys Asp Lys Leu Asn
        35                  40                  45

Asn Asn Ile Ser Ser Val Ala Glu Thr Arg Leu Ser Met Gly Val Gly
    50                  55                  60

Asp Tyr Asp Lys Thr Ala Asp Asp Gly Gly His Lys Leu Asn Thr Asp
65                  70                  75                  80

Ala Leu Asn Gln Thr Pro Leu Glu His His Ile Leu Arg Arg Ile Val
                85                  90                  95

His His Leu Ala Phe Arg Leu Leu Ser Leu Ile Leu Ile Leu Ile Asp
            100                 105                 110

Ile Ala Ile Leu Ile Ala Ser Leu Arg Glu Asn Pro Glu Gly Asp Val
        115                 120                 125

Gln Arg Thr Tyr Asn Tyr Ile Ala Met Ala Phe Ser Val Val Phe Ile
    130                 135                 140

Ala Glu Leu Cys Leu Arg Val Tyr Thr Gln Gly Thr Ser Asp Phe Phe
145                 150                 155                 160

Ser Lys Trp Tyr Asn Lys Val Asp Phe Cys Ile Ile Ala Leu Thr Phe
                165                 170                 175

Val Gly Ser Val Ser Val Leu Leu Ile Thr Asp Leu Lys Pro Phe Asn
            180                 185                 190

Ser His Asn Val Tyr Ile Thr Ala Asp Lys Gln Lys Asn Gly Ile Lys
        195                 200                 205

Ala Asn Phe Thr Val Arg His Asn Val Glu Asp Gly Ser Val Gln Leu
    210                 215                 220

Ala Asp His Tyr Gln Gln Asn Thr Pro Ile Gly Asp Gly Pro Val Leu
225                 230                 235                 240

Leu Pro Asp Asn His Tyr Leu Ser Thr Gln Thr Val Leu Ser Lys Asp
                245                 250                 255

Pro Asn Glu Lys Arg Asp His Met Val Leu Leu Glu Phe Val Thr Ala
            260                 265                 270

Ala Gly Ile Thr His Gly Met Asp Glu Leu Tyr Gly Gly Thr Gly Gly
        275                 280                 285

Ser Ala Ser Gln Gly Glu Glu Leu Phe Thr Gly Val Val Pro Ile Leu
    290                 295                 300

Val Glu Leu Asp Gly Asp Val Asn Gly His Lys Phe Ser Val Arg Gly
305                 310                 315                 320

Glu Gly Glu Gly Asp Ala Thr Ile Gly Lys Leu Thr Leu Lys Phe Ile
                325                 330                 335

Cys Thr Thr Gly Lys Leu Pro Val Pro Trp Pro Thr Leu Val Thr Thr
            340                 345                 350

Leu Thr Tyr Gly Val Gln Cys Phe Ser Arg Tyr Pro Asp His Met Lys
        355                 360                 365
```

```
Arg His Asp Phe Phe Lys Ser Ala Met Pro Glu Gly Tyr Val Gln Glu
    370                 375                 380

Arg Thr Ile Ser Phe Lys Asp Asp Gly Lys Tyr Lys Thr Arg Ala Val
385                 390                 395                 400

Val Lys Phe Glu Gly Asp Thr Leu Val Asn Arg Ile Glu Leu Lys Gly
                405                 410                 415

Thr Asp Phe Lys Glu Asp Gly Asn Ile Leu Gly His Lys Leu Glu Tyr
                420                 425                 430

Asn Ile His Arg Phe Gln Gln Ala Val Val Leu Gly Arg Leu Val Arg
            435                 440                 445

Ile Val Gly Phe Val Arg Phe Met Arg Phe Tyr Thr Glu Lys Lys Asn
450                 455                 460

Leu Thr Lys Gly Ala
465

<210> SEQ ID NO 17
<211> LENGTH: 426
<212> TYPE: PRT
<213> ORGANISM: Artificial Sequence
<220> FEATURE:
<223> OTHER INFORMATION: Xenopus laevis ASAP variant

<400> SEQUENCE: 17

Met Glu Ser Ser Val Thr Asp Glu Gln Arg Glu Pro Ser Met Val
1               5                   10                  15

Asn Gly Phe Gly Lys Thr Glu Ala Lys Val Ile Ile Asp Asn Gly Lys
                20                  25                  30

Asn Glu Val Glu Glu Pro Ala Thr Trp Trp Asn Lys Leu Arg Lys Val
            35                  40                  45

Ile Ser Pro Phe Val Met Ser Phe Gly Phe Arg Val Phe Gly Val Val
50                  55                  60

Leu Ile Ile Val Asp Phe Val Leu Val Ile Val Asp Leu Ser Val Ile
65                  70                  75                  80

Asp Lys Ser Arg Glu Ala Thr Thr Ala Ile Ser Ser Ile Ser Leu Ala
                85                  90                  95

Ile Ser Phe Phe Leu Ile Asp Val Leu Leu His Ile Phe Val Glu
                100                 105                 110

Gly Phe Arg Gln Tyr Phe Ser Ser Lys Leu Asn Ile Phe Asp Ala Ala
            115                 120                 125

Ile Val Ile Val Thr Leu Leu Val Thr Leu Val Tyr Ala Phe Thr Asp
130                 135                 140

Phe Ser Gly Phe Asn Ser His Asn Val Tyr Ile Thr Ala Asp Lys Gln
145                 150                 155                 160

Lys Asn Gly Ile Lys Ala Asn Phe Thr Val Arg His Asn Val Glu Asp
                165                 170                 175

Gly Ser Val Gln Leu Ala Asp His Tyr Gln Gln Asn Thr Pro Ile Gly
            180                 185                 190

Asp Gly Pro Val Leu Leu Pro Asp Asn His Tyr Leu Ser Thr Gln Thr
        195                 200                 205

Val Leu Ser Lys Asp Pro Asn Glu Lys Arg Asp His Met Val Leu Leu
    210                 215                 220

Glu Phe Val Thr Ala Ala Gly Ile Thr His Gly Met Asp Glu Leu Tyr
225                 230                 235                 240

Gly Gly Thr Gly Gly Ser Ala Ser Gln Gly Glu Glu Leu Phe Thr Gly
                245                 250                 255
```

```
Val Val Pro Ile Leu Val Glu Leu Asp Gly Asp Val Asn Gly His Lys
                260                 265                 270

Phe Ser Val Arg Gly Glu Gly Glu Gly Asp Ala Thr Ile Gly Lys Leu
            275                 280                 285

Thr Leu Lys Phe Ile Cys Thr Thr Gly Lys Leu Pro Val Pro Trp Pro
        290                 295                 300

Thr Leu Val Thr Thr Leu Thr Tyr Gly Val Gln Cys Phe Ser Arg Tyr
305                 310                 315                 320

Pro Asp His Met Lys Arg His Asp Phe Phe Lys Ser Ala Met Pro Glu
                325                 330                 335

Gly Tyr Val Gln Glu Arg Thr Ile Ser Phe Lys Asp Asp Gly Lys Tyr
            340                 345                 350

Lys Thr Arg Ala Val Val Lys Phe Glu Gly Asp Thr Leu Val Asn Arg
        355                 360                 365

Ile Glu Leu Lys Gly Thr Asp Phe Lys Glu Asp Gly Asn Ile Leu Gly
    370                 375                 380

His Lys Leu Glu Tyr Asn Ala Thr Asn Ile Pro Gln Leu Val Asn Phe
385                 390                 395                 400

Leu Arg Gly Leu Arg Ile Ile Ile Leu Val Arg Ile Leu Arg Leu Ala
                405                 410                 415

Ser Gln Lys Arg Gln Leu Glu Lys Val Thr
            420                 425

<210> SEQ ID NO 18
<211> LENGTH: 242
<212> TYPE: PRT
<213> ORGANISM: Artificial Sequence
<220> FEATURE:
<223> OTHER INFORMATION: circularly permuted mApple (cpmApple)

<400> SEQUENCE: 18

Val Ser Glu Arg Met Tyr Pro Glu Asp Gly Ala Leu Lys Ser Glu Ile
1               5                   10                  15

Lys Lys Gly Leu Arg Leu Lys Asp Gly Gly His Tyr Ala Ala Glu Val
                20                  25                  30

Lys Thr Thr Tyr Lys Ala Lys Lys Pro Val Gln Leu Pro Gly Ala Tyr
            35                  40                  45

Ile Val Asp Ile Lys Leu Asp Ile Val Ser His Asn Glu Asp Tyr Thr
    50                  55                  60

Ile Val Glu Gln Cys Glu Arg Ala Glu Gly Arg His Ser Thr Gly Gly
65                  70                  75                  80

Met Asp Glu Leu Tyr Lys Gly Gly Thr Gly Gly Ser Leu Val Ser Lys
                85                  90                  95

Gly Glu Glu Asp Asn Met Ala Ile Ile Lys Glu Phe Met Arg Phe Lys
            100                 105                 110

Val His Met Glu Gly Ser Val Asn Gly His Glu Phe Glu Ile Glu Gly
        115                 120                 125

Glu Gly Glu Gly Arg Pro Tyr Glu Ala Phe Gln Thr Ala Lys Leu Lys
    130                 135                 140

Val Thr Lys Gly Gly Pro Leu Pro Phe Ala Trp Asp Ile Leu Ser Pro
145                 150                 155                 160

Gln Phe Met Tyr Gly Ser Lys Ala Tyr Ile Lys His Pro Ala Asp Ile
                165                 170                 175

Pro Asp Tyr Phe Lys Leu Ser Phe Pro Glu Gly Phe Arg Trp Glu Arg
            180                 185                 190
```

```
Val Met Asn Phe Glu Asp Gly Ile Ile His Val Asn Gln Asp Ser
        195                 200                 205

Ser Leu Gln Asp Gly Val Phe Ile Tyr Lys Val Lys Leu Arg Gly Thr
    210                 215                 220

Asn Phe Pro Pro Asp Gly Pro Val Met Gln Lys Lys Thr Met Gly Trp
225                 230                 235                 240

Glu Ala
```

<210> SEQ ID NO 19
<211> LENGTH: 184
<212> TYPE: PRT
<213> ORGANISM: Artificial Sequence
<220> FEATURE:
<223> OTHER INFORMATION: Alligator mississippiensis VSD with a R153Q
      mutation and an addition of a glutamic acid after the starting
      methionine

<400> SEQUENCE: 19

```
Met Glu Thr Thr Val Arg Tyr Glu Gln Gly Ser Glu Pro Pro Glu Val
1               5                   10                  15

Gln Asp Phe Glu Lys Pro Pro Glu Ala Ser Val Lys Ile Asp Asp Gly
            20                  25                  30

Arg Asp Glu Asp Gly Glu Pro Asp Ser Cys Ile Lys Asp Ile Lys Thr
        35                  40                  45

Gln Ile Ser Pro Phe Val Met Ser Phe Gly Arg Val Phe Gly Ile
    50                  55                  60

Val Leu Ile Phe Val Asp Ile Ala Leu Leu Ile Val Asp Leu Ala Val
65                  70                  75                  80

Ser Asp Thr Gln Arg Asn Thr Lys Gln Thr Leu Glu Gly Val Ser Leu
                85                  90                  95

Gly Ile Ala Leu Phe Phe Phe Val Asp Val His Leu Arg Val Phe Val
            100                 105                 110

Glu Gly Phe Arg Thr Tyr Phe Arg Ser Lys Leu Asn Ile Leu Asp Ala
        115                 120                 125

Leu Ile Val Val Gly Thr Leu Leu Ile Asn Met Val Tyr Ser Phe Ser
    130                 135                 140

Gly Phe Ser Ala Ala Asp Lys Ile Pro Gln Met Val Ile Phe Leu Arg
145                 150                 155                 160

Ala Leu Arg Ile Ile Ile Leu Ile Arg Ile Phe Arg Leu Ala Ser Gln
                165                 170                 175

Lys Lys Gln Leu Glu Lys Val Thr
            180
```

<210> SEQ ID NO 20
<211> LENGTH: 226
<212> TYPE: PRT
<213> ORGANISM: Artificial Sequence
<220> FEATURE:
<223> OTHER INFORMATION: Metaseiulus occidentalis VSD with a K195Q
      mutation and an addition of a glutamic acid after the starting
      methionine

<400> SEQUENCE: 20

```
Met Glu Pro Ser Tyr Asp Arg Phe Asn Asn Asp Ser Asn Asn Val Ser
1               5                   10                  15

Ser Asn Asn Asp Ile Asn Asn Lys Arg Asn Arg Ala Gly Asn Asp Asp
            20                  25                  30

Ser Asp Asp His Thr Ala Gly Ser Asp Gly Gly Lys Asp Lys Leu Asn
        35                  40                  45
```

```
Asn Asn Ile Ser Ser Val Ala Glu Thr Arg Leu Ser Met Gly Val Gly
    50              55                  60

Asp Tyr Asp Lys Thr Ala Asp Asp Gly Gly His Lys Leu Asn Thr Asp
65              70                  75                      80

Ala Leu Asn Gln Thr Pro Leu Glu His His Ile Leu Arg Arg Ile Val
                85                  90                  95

His His Leu Ala Phe Arg Leu Leu Ser Leu Ile Leu Ile Leu Ile Asp
            100                 105                 110

Ile Ala Ile Leu Ile Ala Ser Leu Arg Glu Asn Pro Glu Gly Asp Val
        115                 120                 125

Gln Arg Thr Tyr Asn Tyr Ile Ala Met Ala Phe Ser Val Val Phe Ile
    130                 135                 140

Ala Glu Leu Cys Leu Arg Val Tyr Thr Gln Gly Thr Ser Asp Phe Phe
145             150                 155                     160

Ser Lys Trp Tyr Asn Lys Val Asp Phe Cys Ile Ile Ala Leu Thr Phe
                165                 170                 175

Val Gly Ser Val Ser Val Leu Leu Ile Thr Asp Leu Lys Pro Ile His
            180                 185                 190

Arg Phe Gln Gln Ala Val Val Leu Gly Arg Leu Val Arg Ile Val Gly
        195                 200                 205

Phe Val Arg Phe Met Arg Phe Tyr Thr Glu Lys Lys Asn Leu Thr Lys
    210                 215                 220

Gly Ala
225
```

FLUORESCENT PROTEIN VOLTAGE SENSORS FOR MEASURING MEMBRANE POTENTIAL AND IMAGING HIGH-FREQUENCY NEURONAL ELECTRICAL ACTIVITY

CROSS-REFERENCE TO RELATED APPLICATION

This application claims benefit under 35 U.S.C. §119(e) of provisional application 61/902,265, filed Nov. 10, 2013, which is hereby incorporated by reference in its entirety.

STATEMENT REGARDING FEDERALLY SPONSORED RESEARCH OR DEVELOPMENT

This invention was made with Government support under contract 1134416 awarded by the National Science Foundation. The Government has certain rights in this invention.

TECHNICAL FIELD

The present invention pertains generally to the fields of electrophysiology and neuroscience and methods of measuring membrane potential. In particular, the invention relates to engineered fluorescent protein voltage sensors, which comprise a voltage-sensing domain (VSD) comprising four transmembrane segments linked to a circularly permuted fluorescent protein that is inserted into the extracellular loop between the third transmembrane segment (S3) and the fourth transmembrane segment (S4) of the VSD, and methods of using such fluorescent protein voltage sensors for measuring the electrical activity of cells.

BACKGROUND

Understanding how information is processed in the brain would benefit from precise spatio-temporal recording of electrical activity in individual neurons and larger neuronal circuits. Optical reporting of neuronal activity using genetically encoded fluorescent reporters is a promising approach, as it allows for a set of neurons in a region to be genetically defined and simultaneously visualized without the need for chemical access. To unravel the rules of neural coding, an ideal sensor should not only be able to detect all types of membrane electrical activity—not only single action potentials (APs), or spikes, that represent neuronal outputs, but also monitor the amplitude and spatio-temporal distributions of inputs that are received and integrated by neurons (Magee (2000) Nat. Rev. Neurosci. 1:181-190; Zecevic et al. (2003) Imaging nervous system activity with voltage-sensitive dyes, Curr. Protoc. Neurosci Chapter 6, Unit 6.17). The ability to visualize subthreshold potential changes would also allow tracking of up and down states throughout a population of neurons, enabling questions regarding synchrony to be addressed (Castro-Alamancos (2009) Neuroscientist 15:625-634). Finally, tracking high-frequency firing would be useful for visualizing how bursts of neurotransmission are decoded by the postsynaptic neuron (Branco & Hausser (2011) Neuron 69:885-892) and for understanding how the 50-200 Hz firing of fast-spiking interneurons regulates information processing in the brain (Puig et al. (2008) Proc. Natl. Acad. Sci. U.S.A. 105:8428-8433; Royer et al. (2012) Nat. Neurosci. 15:769-775) or is affected in disease (Zhou & Roper (2011) Cereb. Cortex 21:1645-1658).

A genetically encoded sensor with these multiple capabilities remains to be developed. Following intense engineering efforts, reporters for calcium based on fluorescent proteins can now detect single action potentials (Chen et al. (2013) Nature 499, 295-300); however, they remain unable to monitor subthreshold depolarizations and hyperpolarizations, since those events are not typically characterized by large calcium fluxes. Furthermore, calcium transients persist in neurons for hundreds of milliseconds, and thus calcium responses cannot track high-frequency action potential trains (Murthy et al. (2000) Proc. Natl. Acad. Sci. U.S.A. 97:901-906). For example, GCaMP6f, the fastest variant of the latest iteration of calcium sensors, has a mean decay time ($\tau_{1/2}$) of 400 milliseconds (Chen et al. (2013) Nature 499: 295-300). Voltage sensors provide a more direct measure of membrane potential and, in some cases, are faster than calcium sensors. Sensors based on seven-helix microbial rhodopsin are a promising new class of voltage sensor, but currently cannot report neuronal activity over background fluorescence in brain slices or in vivo (Kralj et al. (2012) Nat. Methods 9:90-95; Gong et al. (2013) PLoS One 8:e66959). Moreover, the 5- to 15-milliseconds on- and off-rates of Arch-EEQ (Gong et al., supra), the fastest rhodopsin-based non-conducting sensor to date, are still slow compared to the typical 2-milliseconds duration of action potentials in pyramidal neurons (Staff et al. (2000) J. Neurophysiol. 84:2398-2408). Voltage sensors based on four-helix transmembrane voltage-sensing domains (VSDs) require light at the more phototoxic <450 nm CFP-exciting wavelengths (Lundby et al. (2008) PLoS One 3:e2514), produce suboptimal fluorescence responses to neuronal activity (Lundby et al., supra), or exhibit inactivation kinetics substantially slower than needed to follow fast trains of action potentials (Staff et al., supra). In particular, the recently developed ArcLight family of sensors produce the largest fluorescence response to APs among previously reported VSD-based sensors and are relatively bright, but slow kinetics limit their ability to resolve spikes separated by less than about 50 milliseconds (Cao et al. (2013) Cell 154:904-913; Jin et al. (2012) Neuron 75:779-785). Thus, no existing genetically encoded activity sensor possesses all the characteristics needed for accurate optical reporting of neuronal activity in vivo.

Thus, there remains a need for better voltage sensors and methods for imaging neuronal electrical activity.

SUMMARY

The invention relates to engineered fluorescent protein voltage sensors and methods of using such fluorescent protein voltage sensors for measuring the electrical activity of cells. In particular, fluorescent protein voltage sensors can be used for noninvasive optical monitoring of electrical events in cells, including hyperpolarizations, subthreshold depolarizations, and individual action potentials (APs).

In one aspect, the invention includes a fluorescent protein voltage sensor comprising: a) a voltage-sensing domain (VSD) comprising four transmembrane segments; and b) a circularly permuted fluorescent protein, wherein the circularly permuted fluorescent protein is inserted into an extracellular loop between the third transmembrane segment (S3) and the fourth transmembrane segment (S4) of the VSD. In certain embodiments, the circularly permuted fluorescent protein is inserted at a position 4, 5, or 6 amino acids downstream of the C-terminal end of S3 of the VSD. The fluorescent protein voltage sensor may further comprise a targeting sequence, such as a membrane-targeting sequence (e.g., a signal peptide comprising a plasma membrane targeting sequence, prenylation sequence, or other membrane targeting sequence or organelle targeting sequence) or other targeting sequence that localizes the fluorescent protein to a particular subcellular region.

In certain embodiments, the fluorescent protein voltage sensor comprises a polypeptide selected from the group consisting of a polypeptide comprising an amino acid sequence selected from the group consisting of SEQ ID NOS:1-3 and SEQ ID NOS:13-17, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the polypeptide has voltage sensing characteristics and shows changes in fluorescence intensity in response to depolarization.

The VSD of the fluorescent protein voltage sensor may be derived from a voltage sensitive phosphatase or a voltage-gated ion channel or transporter. In certain embodiments, the fluorescent protein voltage sensor comprises a VSD from a mammal, bird, fish, amphibian, reptile, or insect. Exemplary fluorescent protein voltage sensors comprising voltage sensitive phosphatase VSDs from *Gallus gallus, Xenopus laevis, Danio rerio, Alligator mississippiensis*, and *Metaseiulus occidentalis* are described in Examples 1 and 2. In certain embodiments, the VSD comprises an amino acid sequence selected from the group consisting of SEQ ID NO:4, SEQ ID NO:19, and SEQ ID NO:20, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fluorescent protein voltage sensor has voltage sensing characteristics. In one embodiment, the VSD comprises a mutation comprising a substitution of a glutamine for the amino acid at the position corresponding to 153 numbered relative to the reference sequence of SEQ ID NO:4.

The fluorescent protein voltage sensor can be constructed with any circularly permuted fluorescent protein, wherein the fluorescence intensity of the fluorescent protein voltage sensor is voltage dependent. The choice of a particular circularly permuted fluorescent protein for use in a fluorescent protein voltage sensor may depend on the desired emission spectrum for detection, and includes, but is not limited to, circularly permuted fluorescent proteins with green, blue, cyan, yellow, orange, red, or far-red emissions. Exemplary circularly permuted fluorescent proteins that can be used in the practice of the invention include circularly permuted green fluorescent protein (cpGFP), circularly permuted superfolder GFP (cpsfGFP), circularly permuted mApple (cpmApple), circularly permuted mCherry (cpmCherry), circularly permuted mKate (cpmKate), circularly permuted enhanced green fluorescent protein (cpEGFP), circularly permuted Venus (cpVenus), circularly permuted Citrine (cpCitrine), and circularly permuted enhanced yellow fluorescent protein (cpEYFP). In certain embodiments, the circularly permuted fluorescent protein comprises a polypeptide selected from the group consisting of a polypeptide comprising an amino acid sequence selected from the group consisting of SEQ ID NO:5 and SEQ ID NO:18, or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fluorescence intensity of the fluorescent protein voltage sensor is voltage dependent.

In another aspect, the invention includes a polynucleotide encoding a fluorescent protein voltage sensor. In one embodiment, the invention includes a recombinant polynucleotide comprising a polynucleotide encoding a fluorescent protein voltage sensor operably linked to a promoter. In one embodiment, the promoter is a cell-type specific promoter, for example, a neuron-specific promoter or a cardiac-specific promoter.

In certain embodiments, the recombinant polynucleotide comprises a polynucleotide selected from the group consisting of: a polynucleotide comprising the nucleotide sequence of SEQ ID NO:12 or a variant thereof having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fluorescence intensity of the encoded polypeptide is voltage dependent; and a polynucleotide encoding a polypeptide comprising an amino acid sequence selected from the group consisting of SEQ ID NOS:1-3 and SEQ ID NOS:13-17, or a variant thereof having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fluorescence intensity of the polypeptide is voltage dependent.

In another aspect, the invention includes a host cell comprising a recombinant polynucleotide encoding a fluorescent protein voltage sensor operably linked to a promoter. In certain embodiments, the host cell is an excitable cell (e.g., a neuron, a cardiac cell, or an endocrine cell).

In another aspect, the invention includes a method for monitoring membrane potential using a fluorescent protein voltage sensor described herein. Fluorescent protein voltage sensors can be used to measure the membrane potential of any cell or any phospholipid bilayer enclosed structure.

In one embodiment, the method comprises: a) transfecting a cell with a recombinant polynucleotide encoding a fluorescent protein voltage sensor operably linked to a promoter, whereby the fluorescent protein voltage sensor is expressed and localizes to a membrane of the cell; and b) illuminating the cell with light at an excitation wavelength of the fluorescent protein voltage sensor; and c) monitoring the fluorescence response, wherein the intensity of the fluorescence emitted by the fluorescent protein voltage sensor is correlated with the membrane potential of the cell (e.g. changes in the fluorescence emitted by a fluorescent protein voltage sensor indicate depolarization). The cell may be transfected in vitro or in vivo.

In another embodiment, the method comprises: a) inserting a fluorescent protein voltage sensor into a membrane of the cell; b) illuminating the cell with light at an excitation wavelength of the fluorescent protein voltage sensor; and c) monitoring the fluorescence response, wherein the intensity of the fluorescence emitted by the fluorescent protein voltage sensor is correlated with the membrane potential of the cell.

In certain embodiments, the cell is an excitable cell (e.g., a neuron, a cardiac cell, or an endocrine cell). If the cell having its membrane potential monitored is a neuron, the fluorescent protein voltage sensor may be localized to the plasma membrane of a cell body or projection (e.g., dendrite or axon) of the neuron.

In certain embodiments, monitoring the fluorescence response comprises detecting a single action potential or a train of action potentials (including action potential waveforms having a frequency of up to 200 Hz), a subthreshold potential change, depolarization, or hyperpolarization.

In certain embodiments, the fluorescence response is monitored after exposing the cell to a stimulus. A stimulus may include anything capable of changing the membrane potential or suspected of being able to change the membrane potential of a cell. For example, a stimulus may comprise an electrical current, a drug, a ligand for a receptor, a ligand for an ion channel or transporter, a hormone, or a second messenger. In one embodiment, the membrane potential of the cell is monitored before and after exposure of the cell to the stimulus to allow the magnitude of the change in membrane potential as a result of exposure of the cell to the stimulus to be quantitated.

In another aspect, the invention includes a method of screening an agent for its effect on the membrane potential of a cell, the method comprising: a) monitoring the membrane potential of the cell, according to a method described herein, before and after treatment of the cell with the agent; and b) comparing the membrane potential before and after treatment of the cell with the agent to detect any changes in the membrane potential resulting from treatment of the cell with the agent. Exemplary agents that may be screened by this method include an ion channel modulator (e.g., agonist or antagonist), an ion channel blocker, an ion channel opener, a ligand for an ion channel, transporter, or receptor, a hormone, a second messenger, or a drug or other organic or inorganic molecule suspected of affecting membrane potential.

In another aspect, the invention includes a method for producing a fluorescent protein voltage sensor, the method comprising: transforming a host cell with a recombinant polynucleotide encoding a fluorescent protein voltage sensor operably linked to a promoter; culturing the transformed host cell under conditions whereby the fluorescent protein voltage sensor is expressed; and isolating the fluorescent protein voltage sensor from the host cell.

In another aspect, the invention includes a polypeptide comprising an engineered VSD described herein. In certain embodiments, the VSD comprises an amino acid sequence selected from the group consisting of SEQ ID NO:19 and SEQ ID NO:20; or a variant thereof having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the polypeptide has voltage sensing characteristics.

In another aspect, the invention includes a kit for preparing or using fluorescent protein voltage sensors according to the methods described herein. Such kits may comprise one or more fluorescent protein voltage sensors, or nucleic acids encoding such fluorescent protein voltage sensors, or expression vectors, or cells, or other reagents for preparing fluorescent protein voltage sensors, as described herein.

In the practice of the invention, the fluorescence of a fluorescent protein voltage sensor can be monitored by any suitable method. For example, fluorescence of fluorescent protein voltage sensors can be detected by a fluorimeter, a fluorescence microscope, a fluorescence microplate reader, a fluorometric imaging plate reader, or fluorescence-activated cell sorting. In certain embodiments, the fluorescent protein voltage sensor is detected using confocal microscopy, two-photon excitation microscopy, light sheet microscopy, or light-field microscopy.

These and other embodiments of the subject invention will readily occur to those of skill in the art in view of the disclosure herein.

BRIEF DESCRIPTION OF THE FIGURES

FIGS. 1A-1G show the ASAP1 design and voltage response characteristics. FIG. 1A shows that ASAP1 consists of a circularly permuted fluorescent protein domain inserted into the S3-S4 loop of a voltage-sensing domain. Depolarization leads to a change in fluorescence. FIG. 1B shows that ASAP1 was localized to the plasma membrane in a 12-day-in-vitro (DIV) dissociated rat neuron imaged by confocal microscopy (top) and in a neuron within a fixed brain slice from an 8 week old mouse transfected in utero imaged by two-photon microscopy (bottom). Right panels show details from the left panels. Scale bar, 10 pm. FIG. 1C shows fluorescence responses in a representative HEK293 cell (above) to voltage steps from −160 to 80 mV (below). Responses were measured 25 milliseconds apart and were calculated relative to fluorescence at −70 mV baseline. FIG. 1D shows the mean fluorescence response (n=8) versus transmembrane voltage. Error bars are standard error of the mean (SEM). FIG. 1E shows activation and inactivation kinetics of ASAP1. FIG. 1F shows a comparison of ASAP1 and ArcLight Q239 responses to representative action potentials induced by current injection in cultured hippocampal neurons. AP half-widths were 3.3 and 3.6 milliseconds for the ASAP1- and ArcLight Q239-expressing neurons, respectively. Fluorescence spike half-widths were 3.7 milliseconds and 6.5 milliseconds for ASAP1 and ArcLight Q239, respectively. FIG. 1G shows that ASAP produces larger fluorescence responses to individual current-triggered APs in cultured neurons than ArcLight Q239 (two-tailed Student t-test, p=0.0038, n=5 each). Error bars are standard error of the mean (SEM) of the average response of individual neurons across 12 to 25 APs per neuron.

FIG. 2A shows that ASAP1 can follow 200 Hz trains of action potential waveforms (2.0 milliseconds half-width, 75 mV peak amplitude) mammalian cells, while ArcLight Q239 can follow trains of 30 Hz but not of 100 Hz. FIG. 2B shows that ASAP1 can detect subthreshold potential and hyperpolarization waveforms in neurons. Subthreshold depolarizations and hyperpolarizations have peak amplitudes of 5, 10, 15 and 20 mV, and peak half-widths of 17 milliseconds (depolarizations) and 38 milliseconds (hyperpolarizations). FIG. 2C shows that ASAP1 has faster kinetics, which allow improved resolution of a 100 Hz, three-AP waveform sequence in neurons. Spike width is 1.8 milliseconds.

FIG. 3A shows fluorescence responses of ASAP1 (left) and ArcLight Q239 (right) to spontaneous subthreshold potentials and APs in cultured hippocampal neurons. FIG. 3B shows that ASAP1 followed spontaneous AP trains in a cultured hippocampal neuron. FIG. 3C shows that in an acute cortical slice from a mouse brain transfected in utero, ASAP1 produced large responses to individual current-induced APs in a Layer 5 pyramidal cell. This cell had a resting potential of −80 mV, requiring injection of 1.5 nA current to induce APs. FIG. 3D shows that ASAP1 tracked APs and subthreshold depolarizations in a Layer 2/3 neuron injected with current pulses at 25 Hz. All traces are from single trials either without filtering (FIGS. 3A-3C) or with a 100 Hz low-pass Butterworth filter (FIG. 3D).

FIG. 4A shows an alignment of the S3-S4 region of four VSDs extracted from voltage sensitive phosphatases of different species. FIG. 4B shows the *G. gallus* VSD with the R153Q mutation and an insertion of circularly permuted green fluorescent protein (cpGFP) from GCaMP3 at 4, 5, and 6 amino acids downstream of S3 exhibited bright membrane-localized fluorescence in HEK293A cells. Insertion at other positions yielded suboptimal membrane localization or dimness. Scale bar, 10 pm. FIG. 4C shows the fluorescence response in HEK293A cells to voltage steps from −150 mV to +50 mV relative to the holding potential of −70 mV for three sensor variants with different insertion points. All three variants produced similar fluorescence responses, with an approximately 3% decrease in intensity from −70 mV to +30 mV. Error bars are standard error of the mean (SEM). FIG. 4D shows constructs in which the cpGFP from GCaMP3 between Ala-148 and Thr-149 was replaced with cpGFP from GECO1.2 or the OPT variant of superfolder GFP (cpsfGFP). To normalize for cell-to-cell or well-to-well variability in transfection efficiency or expression, each sensor was coexpressed with mCherryCAAX using an internal ribosome entry site. For each sensor, the green and red fluorescence images were identically scaled and merged. The relative ratio of green to red fluorescence, an indication of sensor brightness, was largest for the cpsfGFP-based voltage sensor. Scale bar, 10 pm.

FIG. 5A shows that substituting the VSD from *Gallus gallus* with the VSD of *Xenopus laevis* or *Danio rerio* does not alter membrane localization in HEK293A cells, while substituting with the VSD of *Ciona intestinalis* results in loss of membrane localization for all insertion positions tested, 1 to 12 amino acids downstream of S3. Reverting the R153Q mutation in ASAP produces comparable membrane localization to the R153Q sensor. Scale bar, 10 pm. FIG. 5B shows that ASAP variants with VSD from alternative species show reduced fluorescence dynamic range in HEK293A cells for voltage steps from −150 mV to +50 mV relative to −70 mV. Holding potential was −11 mV, close to HEK293A resting potential (typically −10 to −20 mV). Error bars are standard error of the mean (SEM). FIG. 5C shows that reverting the R153Q mutation in ASAP does not improve fluorescence dynamic range in HEK293A for voltage steps from −150 mV to +50 mV relative to −70 mV. Holding potential was −11 mV. Error bars, SEM.

FIG. 6A shows that changing termini for circularly permuted variants of sfGFP-OPT did not disrupt efficient membrane localization in HEK293A cells. Numbers indicate location of the new N- and C-termini using non-permuted sfGFP numbering. FIG. 6B shows that these variants exhibited reduced responses in HEK293A to voltage steps. FIG. 6C shows the same data replotted to better show reversal of the fluorescence response in sensors with cpsfGFP-OPT 147-146, 148-147 and 149-147. FIG. 6D shows that variants with deletion of one amino acid at either side of the VSD-GFP or GFP-VSD junction showed efficient membrane localization in HEK293A cells. FIG. 6E shows that deletion of the N-terminal amino acid of cpsfGFP-OPT (Phe-145) dramatically reduced fluorescence response in HEK293A cells. Deletion of any of the other three junctional amino acids did not improve fluorescence responses within the physiological range (−100 mV to +50 mV). cspfGFP correspond to the OPT variant used in ASAP1. For all panels, samples sizes (n) correspond to individual HEK293A cells. Error bars are mean±SEM.

FIG. 7A shows that conservative mutations of the Phe-145 of cpsfGFPOPT immediately C-terminal to the VSD-GFP junction to leucine (F145L), methionine (F145M) or tyrosine (F145Y) produced qualitatively comparable membrane localization to ASAP1 in HEK293A cells. Scale bar, 10 μm. FIG. 7B shows that F145I, F145L, F145M, and F145Y reduced fluorescence responses in HEK293A cells to voltage steps from −150 to +50 mV. Samples sizes (n) correspond to individual cells. Error bars are mean±SEM.

FIG. 9A shows the fluorescence response to five simulated action potentials with 4 ms full-width at half-maximum and 100 mV-peak amplitude. FIG. 9B shows the fluorescence response to ten simulated action potentials delivered at 100 hz. Simulated action potential characteristics are identical to those in FIG. 9A. FIG. 9C shows the maximal fluorescence responses to 1 second voltage steps from a holding potential of −70 mV.

FIG. 10A shows the fluorescence response to five simulated action potentials with 4 ms full-width at half-maximum and 100 mV peak amplitude. FIG. 10B shows the fluorescence response to ten simulated action potentials delivered at 100 hz. Simulated action potential characteristics are identical to those in FIG. 10A. FIG. 10C shows the maximal fluorescence responses to 1 second voltage steps from a holding potential of −70 mV.

DETAILED DESCRIPTION

Figure 1A:
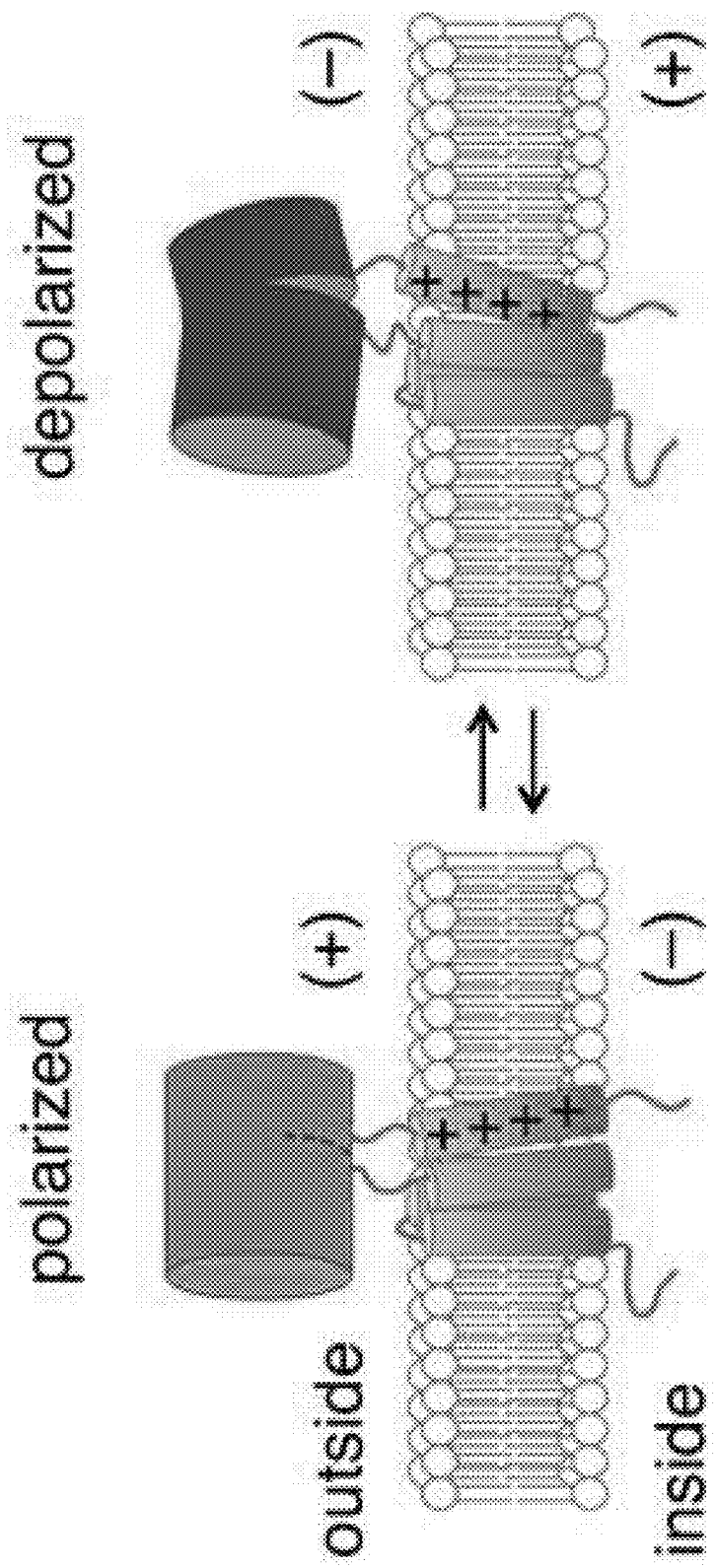

The practice of the present invention will employ, unless otherwise indicated, conventional methods of electrophysiology, neurobiology, medicine, cell biology, chemistry, biochemistry, molecular biology, and recombinant DNA techniques, within the skill of the art. Such techniques are explained fully in the literature. See, e.g., *Single-Channel Recording* (B. Sakmann and E. Neher eds., Springer; $2^{nd}$ edition 1995, $2^{nd}$ printing 2009 edition); Dubois *Action Potential: Biophysical and Cellular Context, Initiation, Phases and Propagation* (Cell Biology Research Progress, Nova Science Publishers, Inc., $1^{st}$ edition, 2010); *Optogenetics, Volume 196: Tools for Controlling and Monitoring Neuronal Activity* (Progress in Brain Research, T. Knopfel, E. S. Boyden eds., Elsevier; $1^{st}$ edition, 2012); *Imaging in Neuroscience: A Laboratory Manual* (F. Helmchen, A. Konnerth, R. Yuste eds., Cold Spring Harbor, $1^{st}$ edition, 2011); A. L. Lehninger, *Biochemistry* (Worth Publishers, Inc., current addition); Sambrook, et al., *Molecular Cloning: A Laboratory Manual* ($3^{rd}$ Edition, 2001); *Methods In Enzymology* (S. Colowick and N. Kaplan eds., Academic Press, Inc.).

All publications, patents and patent applications cited herein, whether supra or infra, are hereby incorporated by reference in their entireties.

I. DEFINITIONS

In describing the present invention, the following terms will be employed, and are intended to be defined as indicated below.

It must be noted that, as used in this specification and the appended claims, the singular forms "a," "an" and "the" include plural referents unless the content clearly dictates otherwise. Thus, for example, reference to "a protein" includes a mixture of two or more proteins, and the like.

The term "about," particularly in reference to a given quantity, is meant to encompass deviations of plus or minus five percent.

"Fluorescent protein" refers to any protein capable of emitting light when excited with appropriate electromagnetic radiation. Fluorescent proteins include proteins having amino acid sequences that are either natural or engineered (e.g., green fluorescent protein (GFP), circularly permuted green fluorescent protein (cpGFP), and variants and derivatives thereof).

The term "fluorescence characteristics" means an ability to emit fluorescence by irradiation of excitation light. The fluorescence characteristics of a fluorescent protein voltage sensor comprising a circularly permuted fluorescent protein may be comparable to or different from those of the fluorescent proteins which have the amino acid sequences shown in SEQ ID NOS:1-3 and SEQ ID NOS:13-17. Examples of parameters of the fluorescence characteristics include fluorescence intensity, excitation wavelength, fluorescence wavelength, and pH sensitivity.

The term "voltage sensing characteristics" refers to an ability to respond to changes in membrane potential in a detectable manner. For example, the voltage sensing characteristics of a fluorescent protein voltage sensor comprising a VSD derive from voltage-induced conformational changes or movement of the VSD, which may in turn detectably change the intensity of fluorescence emitted by a fluorophore attached to an extracellular loop of the VSD.

The terms "polypeptide" and "protein" refer to a polymer of amino acid residues and are not limited to a minimum length. Thus, peptides, oligopeptides, dimers, multimers, and the like, are included within the definition. Both full length proteins and fragments thereof are encompassed by the definition. The terms also include postexpression modifications of the polypeptide, for example, glycosylation, acetylation, phosphorylation, hydroxylation, and the like. Furthermore, for purposes of the present invention, a "polypeptide" refers to a protein which includes modifications, such as deletions, additions and substitutions to the native sequence, so long as the protein maintains the desired activity. These modifications may be deliberate, as through site directed mutagenesis, or may be accidental, such as through mutations of hosts which produce the proteins or errors due to PCR amplification.

By "derivative" is intended any suitable modification of the native polypeptide of interest, of a fragment of the native polypeptide, or of their respective analogs, such as glycosylation, phosphorylation, polymer conjugation (such as with polyethylene glycol), or other addition of foreign moieties, as long as the desired biological activity of the native polypeptide is retained. Methods for making polypeptide fragments, analogs, and derivatives are generally available in the art.

By "fragment" is intended a molecule consisting of only a part of the intact full length sequence and structure. The fragment can include a C-terminal deletion an N-terminal deletion, and/or an internal deletion of the polypeptide. Active fragments of a particular protein or polypeptide will generally include at least about 5-10 contiguous amino acid residues of the full length molecule, preferably at least about 15-25 contiguous amino acid residues of the full length molecule, and most preferably at least about 20-50 or more contiguous amino acid residues of the full length molecule, or any integer between 5 amino acids and the full length sequence, provided that the fragment in question retains biological activity, such as catalytic activity, ligand binding activity, regulatory activity, fluorescence, or voltage-sensing characteristics, as defined herein.

"Substantially purified" generally refers to isolation of a substance (compound, polynucleotide, protein, polypeptide, polypeptide composition) such that the substance comprises the majority percent of the sample in which it resides. Typically in a sample, a substantially purified component comprises 50%, preferably 80%-85%, more preferably 90-95% of the sample. Techniques for purifying polynucleotides and polypeptides of interest are well-known in the art and include, for example, ion-exchange chromatography, affinity chromatography and sedimentation according to density.

By "isolated" is meant, when referring to a polypeptide, that the indicated molecule is separate and discrete from the whole organism with which the molecule is found in nature or is present in the substantial absence of other biological macro molecules of the same type. The term "isolated" with respect to a polynucleotide is a nucleic acid molecule devoid, in whole or part, of sequences normally associated with it in nature; or a sequence, as it exists in nature, but having heterologous sequences in association therewith; or a molecule disassociated from the chromosome.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. The term also includes fluorescent proteins and polypeptides.

"Homology" refers to the percent identity between two polynucleotide or two polypeptide moieties. Two nucleic acid, or two polypeptide sequences are "substantially homologous" to each other when the sequences exhibit at least about 50% sequence identity, preferably at least about 75% sequence identity, more preferably at least about 80%-85% sequence identity, more preferably at least about 90% sequence identity, and most preferably at least about 95%-98% sequence identity over a defined length of the molecules. As used herein, substantially homologous also refers to sequences showing complete identity to the specified sequence.

In general, "identity" refers to an exact nucleotide to nucleotide or amino acid to amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in Atlas of Protein Sequence and Structure M. O. Dayhoff ed., 5 Suppl. 3:353 358, National biomedical Research Foundation, Washington, D.C., which adapts the local homology algorithm of Smith and Waterman Advances in Appl. Math. 2:482 489, 1981 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by =HIGH SCORE; Databases=non redundant, GenBank+EMBL+DDBJ+PDB+ GenBank CDS translations+Swiss protein+Spupdate+PIR. Details of these programs are readily available.

Alternatively, homology can be determined by hybridization of polynucleotides under conditions which form stable duplexes between homologous regions, followed by digestion with single stranded specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; DNA Cloning, supra; Nucleic Acid Hybridization, supra.

"Recombinant" as used herein to describe a nucleic acid molecule means a polynucleotide of genomic, cDNA, viral, semisynthetic, or synthetic origin which, by virtue of its origin or manipulation, is not associated with all or a portion of the polynucleotide with which it is associated in nature. The term "recombinant" as used with respect to a protein or polypeptide means a polypeptide produced by expression of a recombinant polynucleotide. In general, the gene of interest is cloned and then expressed in transformed organisms, as described further below. The host organism expresses the foreign gene to produce the protein under expression conditions.

The term "transformation" refers to the insertion of an exogenous polynucleotide into a host cell, irrespective of the method used for the insertion. For example, direct uptake, transduction or f-mating are included. The exogenous polynucleotide may be maintained as a non-integrated vector, for example, a plasmid, or alternatively, may be integrated into the host genome.

"Recombinant host cells," "host cells," "cells," "cell lines," "cell cultures," and other such terms denoting microorganisms or higher eukaryotic cell lines cultured as unicellular entities refer to cells which can be, or have been, used as recipients for recombinant vector or other transferred DNA, and include the original progeny of the original cell which has been transfected.

A "coding sequence" or a sequence which "encodes" a selected polypeptide, is a nucleic acid molecule which is transcribed (in the case of DNA) and translated (in the case of mRNA) into a polypeptide in vivo when placed under the control of appropriate regulatory sequences (or "control elements"). The boundaries of the coding sequence can be determined by a start codon at the 5' (amino) terminus and a translation stop codon at the 3' (carboxy) terminus. A coding sequence can include, but is not limited to, cDNA from viral, prokaryotic or eukaryotic mRNA, genomic DNA sequences from viral or prokaryotic DNA, and even synthetic DNA sequences. A transcription termination sequence may be located 3' to the coding sequence.

Typical "control elements," include, but are not limited to, transcription promoters, transcription enhancer elements, transcription termination signals, polyadenylation sequences (located 3' to the translation stop codon), sequences for optimization of initiation of translation (located 5' to the coding sequence), and translation termination sequences.

"Operably linked" refers to an arrangement of elements wherein the components so described are configured so as to perform their usual function. Thus, a given promoter operably linked to a coding sequence is capable of effecting the expression of the coding sequence when the proper enzymes are present. The promoter need not be contiguous with the coding sequence, so long as it functions to direct the expression thereof. Thus, for example, intervening untranslated yet transcribed sequences can be present between the promoter sequence and the coding sequence and the promoter sequence can still be considered "operably linked" to the coding sequence.

"Encoded by" refers to a nucleic acid sequence which codes for a polypeptide sequence, wherein the polypeptide sequence or a portion thereof contains an amino acid sequence of at least 3 to 5 amino acids, more preferably at least 8 to 10 amino acids, and even more preferably at least 15 to 20 amino acids from a polypeptide encoded by the nucleic acid sequence.

"Expression cassette" or "expression construct" refers to an assembly which is capable of directing the expression of the sequence(s) or gene(s) of interest. An expression cassette generally includes control elements, as described above, such as a promoter which is operably linked to (so as to direct transcription of) the sequence(s) or gene(s) of interest, and often includes a polyadenylation sequence as well. Within certain embodiments of the invention, the expression cassette described herein may be contained within a plasmid construct. In addition to the components of the expression cassette, the plasmid construct may also include, one or more selectable markers, a signal which allows the plasmid construct to exist as single stranded DNA (e.g., a M13 origin of replication), at least one multiple cloning site, and a "mammalian" origin of replication (e.g., a SV40 or adenovirus origin of replication).

"Purified polynucleotide" refers to a polynucleotide of interest or fragment thereof which is essentially free, e.g., contains less than about 50%, preferably less than about 70%, and more preferably less than about at least 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

The term "transfection" is used to refer to the uptake of foreign DNA by a cell. A cell has been "transfected" when exogenous DNA has been introduced inside the cell membrane. A number of transfection techniques are generally known in the art. See, e.g., Graham et al. (1973) Virology, 52:456, Sambrook et al. (2001) Molecular Cloning, a laboratory manual, 3rd edition, Cold Spring Harbor Laboratories, New York, Davis et al. (1995) Basic Methods in Molecular Biology, 2nd edition, McGraw-Hill, and Chu et al. (1981) Gene 13:197. Such techniques can be used to introduce one or more exogenous DNA moieties into suitable host cells. The term refers to both stable and transient uptake of the genetic material, and includes uptake of recombinant polynucleotides encoding fluorescent protein voltage sensors.

A "vector" is capable of transferring nucleic acid sequences to target cells (e.g., viral vectors, non-viral vectors, particulate carriers, and liposomes). Typically, "vector construct," "expression vector," and "gene transfer vector," mean any nucleic acid construct capable of directing the expression of a nucleic acid of interest and which can transfer nucleic acid sequences to target cells. Thus, the term includes cloning and expression vehicles, as well as viral vectors.

The terms "variant," "analog" and "mutein" refer to biologically active derivatives of the reference molecule that retain desired activity, such as fluorescence or voltage sensing characteristics. In general, the terms "variant" and "analog" refer to compounds having a native polypeptide sequence and structure with one or more amino acid additions, substitutions (generally conservative in nature) and/or deletions, relative to the native molecule, so long as the modifications do not destroy biological activity and which are "substantially homologous" to the reference molecule as defined below. In general, the amino acid sequences of such analogs will have a high degree of sequence homology to the reference sequence, e.g., amino acid sequence homology of more than 50%, generally more than 60%-70%, even more particularly 80%-85% or more, such as at least 90%-95% or more, when the two sequences are aligned. Often, the analogs will include the same number of amino acids but will include substitutions, as explained herein. The term "mutein" further includes polypeptides having one or more amino acid-like molecules including but not limited to compounds comprising only amino and/or imino molecules, polypeptides containing one or more analogs of an amino acid (including, for example, unnatural amino acids, etc.), polypeptides with substituted linkages, as well as other modifications known in the art, both naturally occurring and non-naturally occurring (e.g., synthetic), cyclized, branched molecules and the like. The term also includes molecules comprising one or more N-substituted glycine residues (a "peptoid") and other synthetic amino acids or peptides. (See, e.g., U.S. Pat. Nos. 5,831,005; 5,877,278; and 5,977,301; Nguyen et al., Chem. Biol. (2000) 7:463-473; and Simon et al., Proc. Natl. Acad. Sci. USA (1992) 89:9367-9371 for descriptions of peptoids). Methods for making polypeptide analogs and muteins are known in the art and are described further below.

As explained above, analogs generally include substitutions that are conservative in nature, i.e., those substitutions that take place within a family of amino acids that are related in their side chains. Specifically, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cysteine, serine threonine, and tyrosine. Phenylalanine, tryptophan, and tyrosine are sometimes classified as aromatic amino acids. For example, it is reasonably predictable that an isolated replacement of leucine with isoleucine or valine, an aspartate with a glutamate, a threonine with a serine, or a similar conservative replacement of an amino acid with a structurally related amino acid, will not have a major effect on the biological activity. For example, the polypeptide of interest may include up to about 5-10 conservative or non-conservative amino acid substitutions, or even up to about 15-25 conservative or non-conservative amino acid substitutions, or any integer between 5-25, so long as the desired function of the molecule remains intact. One of skill in the art may readily determine regions of the molecule of interest that can tolerate change by reference to Hopp/Woods and Kyte-Doolittle plots, well known in the art.

"Gene transfer" or "gene delivery" refers to methods or systems for reliably inserting DNA or RNA of interest into a host cell. Such methods can result in transient expression of non-integrated transferred DNA, extrachromosomal replication and expression of transferred replicons (e.g., episomes), or integration of transferred genetic material into the genomic DNA of host cells. Gene delivery expression vectors include, but are not limited to, vectors derived from bacterial plasmid vectors, viral vectors, non-viral vectors, alphaviruses, pox viruses and vaccinia viruses.

The term "derived from" is used herein to identify the original source of a molecule but is not meant to limit the method by which the molecule is made which can be, for example, by chemical synthesis or recombinant means.

A polynucleotide "derived from" a designated sequence refers to a polynucleotide sequence which comprises a contiguous sequence of approximately at least about 6 nucleotides, preferably at least about 8 nucleotides, more preferably at least about 10-12 nucleotides, and even more preferably at least about 15-20 nucleotides corresponding, i.e., identical or complementary to, a region of the designated nucleotide sequence. The derived polynucleotide will not necessarily be derived physically from the nucleotide sequence of interest, but may be generated in any manner, including, but not limited to, chemical synthesis, replication, reverse transcription or transcription, which is based on the information provided by the sequence of bases in the region(s) from which the polynucleotide is derived. As such, it may represent either a sense or an antisense orientation of the original polynucleotide.

The terms "subject," "individual," and "patient," are used interchangeably herein and refer to any subject, eukaryotic or prokaryotic, for whom monitoring membrane potential is desired, including bacteria, protists, fungi, plants, and animals. Subjects may include humans, cattle, dogs, cats, guinea pigs, rabbits, rats, mice, horses, and so on. In some cases, the methods of the invention find use in experimental animals, in veterinary application, and in the development of animal models for disease, including, but not limited to, rodents including mice, rats, and hamsters; and primates.

II. MODES OF CARRYING OUT THE INVENTION

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

The present invention is based on the discovery of engineered fluorescent protein voltage sensors that can be used to measure the membrane potential of cells. In particular, the inventors have constructed a fluorescent protein voltage sensor, referred to as Allosteric Sensor for Action Potentials 1 (ASAP1), comprising a voltage-sensing domain from a voltage-sensitive phosphatase linked to a circularly permuted fluorescent protein, which is inserted into the extracellular loop between the third (S3) and fourth (S4) transmembrane segments of the voltage-sensing domain (see Examples 1 and 2). The inventors have further shown that such a fluorescent protein voltage sensor can be used for measuring the electrical activity of neurons, including single action potentials, trains of action potentials, and subthreshold potential changes and, in particular, for imaging high-frequency neuronal electrical activity (see Examples 1 and 2). Additionally, fluorescent protein voltage sensors can be used for a variety of other purposes, including measuring the membrane potential of other excitable cells, such as cardiac cells and endocrine cells, and for screening agents that target ion channels or transporters for their effects on membrane potential.

In order to further an understanding of the invention, a more detailed discussion is provided below regarding fluorescent protein voltage sensors and methods of using them for measuring membrane potential and imaging high-frequency neuronal electrical activity.

A. Fluorescent Protein Voltage Sensors

A fluorescent protein voltage sensor comprises a VSD comprising four transmembrane segments and a fluorophore, which is inserted into the extracellular loop between the third transmembrane segment (S3) and the fourth transmembrane segment (S4) of the VSD. Voltage-induced conformational changes or movement of the VSD result in detectable changes in the intensity of the fluorescence emitted by the fluorophore attached to the extracellular loop of the VSD, which allows optical monitoring of changes in membrane potential. In certain embodiments, the fluorophore is inserted at a position 4, 5, or 6 amino acids downstream of the C-terminal end of S3 of the VSD. In certain embodiments, the fluorescent protein voltage sensor comprises an amino acid sequence selected from the group consisting of SEQ ID NOS:1-3 and SEQ ID NOS:13-17; or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fluorescent protein voltage sensor has voltage sensing characteristics and shows changes in fluorescence intensity in response to depolarization.

In certain embodiments, the VSD is derived from a voltage sensitive phosphatase or a voltage-gated ion channel or transporter. A number of VSD nucleic acid and protein sequences are known. Representative VSD sequences of voltage sensitive phosphatases are shown in the National Center for Biotechnology Information (NCBI) database. See, for example, NCBI entries: Accession Nos. XP_417079, XP_005014905, XP_005501909, XP_005446669, XP_005240290, XP_005147697, EMC87706, XP_005516390, XP_005037985, XP_002195057, XP_005305673, EMP28021, XP_006025846, XP_003203348, XP_005482478, XP_005420846, XP_005305674, EOB04857, XP_005155316, XP_005501910, NP_001020629, BAG50379, XP_005472302, XP_003446945, NP_001267536, XP_005305675, XP_005746686, XP_005746683, XP_004550094, XP_005928077, NP_001090072, CAG00470, XP_004076268, XP_005746687, XP_003971378, XP_006002818, NP_001015951, XP_005807119, XP_005635462, XP_005635461, XP_005635460, XP_005635458, XP_004482145, XP_002917732, XP_004388137, XP_004399551, XP_005668431, XP_006259938, XP_003745380, AAI54862, XP_001513133, XP_005601238, ERE88737, ERE88738, XP_003801862, XP_003503371, XP_003412628, XP_005687666, XP_005966581, XP_004012323, XP_005368915, XP_004680395, XP_005900323, XP_003586758, XP_002749061, XP_005213782, ELR53153, XP_005213781, XP_004619623, NP_001102347, XP_004274689, XP_004323024, XP_005330305, XP_003477330, XP_003934442, XP_001082960, NP_954866, CAC44243, XP_003778255, AAI07330, CAC44244, EDL32896, NP_954869, CAC44245, XP_005877021, AAP45144, EDL32897, NP_954868, AAH28719, NP_954870, P56180, AAC34574, XP_003913711, XP_005596114, NP_001028998, EGV95012, XP_002800726, Q4R6N0, XP_004062630; all of which sequences (as entered by the date of filing of this application) are herein incorporated by reference. In addition, representative VSD sequences of voltage-gated ion channels are also shown in the National Center for Biotechnology Information (NCBI) database. See, for example, NCBI entries: Accession Nos. NM_001204269, NM_004974, NM_008417, NG_027997, NM_001085753, XM_005270842, NM_001110418, NM_012970, NM_013186, NM_004975, NM_008420, NM_001085788, AF090124, NM_001112741, NM_004976, NM_001112739, NM_008421, NM_012856, NM_004979, NG_012515, NW_001842363, NM_008423, NM_001105748, NM_013178, NM_000334, NM_133199, NG_011699, XM_005257566, NM_001008880, NM_001081761, NM_174934, NM_001142349, NM_001142348, NR_024527, XM_396385, NM_001112739, NM_008421, NM_001273072, NM_001273071, NM_164554, NM_057373, NM_001144310, XM_003371258, XM_964837, NM_001243812, NM_000718, XM_003374154, XM_003380160, NM_199248, NM_199247, NM_000723, NM_001145798, NM_001005747, NM_001005746, NM_000726, NM_002233, NM_001199861, NM_001199860, NM_172130, NM_003636, NM_001172975, NM_001199863, NM_001199862, NM_201572, NM_201571, NM_001167945, NM_201593, NM_201570, NM_201597, NM_000724, NM_201590, NM_201596, NM_212837, NM_002232, NM_172159, NM_002234, NM_004974, NM_003471, NM_172160, NM_001204269, NM_139216, and NM_139217; all of which sequences (as entered by the date of filing of this application) are herein incorporated by reference. Any of these sequences (i.e., VSD sequences from a voltage-sensitive phosphatase or a voltage-gated ion channel or transporter) or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, can be used to construct a fluorescent protein voltage sensor, or a nucleic acid encoding a fluorescent protein voltage sensor, as described herein. In certain embodiments, the fluorescent protein voltage sensor comprises a voltage sensitive phosphatase VSD from a mammal, bird, fish, amphibian, reptile, or insect. Exemplary fluorescent protein voltage sensors comprising voltage sensitive phosphatase VSDs derived from *Gallus gallus, Xenopus laevis, Danio rerio, Alligator mississippiensis*, or *Metaseiulus occidentalis* are described in Examples 1 and 2.

In one embodiment, the fluorescent protein voltage sensor comprises a VSD derived from a *Gallus gallus* voltage sensitive phosphatase (VSP). A representative amino acid sequence of a VSD from *Gallus gallus* is presented in SEQ ID NO:4. A polypeptide comprising the sequence of SEQ ID NO:4 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the polypeptide has voltage sensing characteristics, can be used to construct a fluorescent protein voltage sensor, as described herein. In one embodiment, the VSD comprises a mutation comprising a substitution of a glutamine for the amino acid at the position corresponding to 153 numbered relative to the reference sequence of SEQ ID NO:4.

In another embodiment, the fluorescent protein voltage sensor comprises a VSD derived from a *Alligator mississippiensis* voltage sensitive phosphatase (VSP). A representative amino acid sequence of a VSD from *Alligator mississippiensis* is presented in SEQ ID NO:19. A polypeptide comprising the sequence of SEQ ID NO:19 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the polypeptide has voltage sensing characteristics, can be used to construct a fluorescent protein voltage sensor, as described herein. In one embodiment, the VSD comprises a mutation comprising a substitution of a glutamine for the amino acid at the position corresponding to 153 numbered relative to the reference sequence of SEQ ID NO:19.

In yet another embodiment, the fluorescent protein voltage sensor comprises a VSD derived from a *Metaseiulus occidentalis* voltage sensitive phosphatase (VSP). A representative amino acid sequence of a VSD from *Metaseiulus occidentalis* is presented in SEQ ID NO:20. A polypeptide comprising the sequence of SEQ ID NO:20 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the polypeptide has voltage sensing characteristics, can be used to construct a fluorescent protein voltage sensor, as described herein. In one embodiment, the VSD comprises a mutation comprising a substitution of a glutamine for the amino acid at the position corresponding to 195 numbered relative to the reference sequence of SEQ ID NO:20.

In certain embodiments, the fluorophore is a circularly permuted fluorescent protein. The fluorescent protein voltage sensor can be constructed with any circularly permuted fluorescent protein, wherein the fluorescence intensity of the fluorescent protein voltage sensor is voltage dependent. The choice of a particular circularly permuted fluorescent protein for use in a fluorescent protein voltage sensor may depend on the desired emission spectrum for detection, and include, but is not limited to, circularly permuted fluorescent proteins with green, blue, cyan, yellow, orange, red, or far-red emissions. A number of circularly permuted fluorescent proteins are known. See, e.g., Pedelacq et al. (2006) Nat. Biotechnol. 24:79-88 for a description of circularly permuted superfolder GFP variant (cpsfGFP), Zhao et al. (2011) Science 333:1888-1891 for a description of circularly permuted mApple; Shui et al. (2011) PLoS One; 6(5): e20505 for a description of circularly permuted variants of mApple and mKate; Carlson et al. (2010) Protein Science 19:1490-1499 for a description of circularly permuted red fluorescent proteins, Gautam et al. (2009) Front. Neuroeng. 2:14 for a description of circularly permuted variants of enhanced green fluorescent protein (EGFP) and mKate, Zhao et al. (2011) Science 333(6051):1888-1891 for a description of a circularly permuted variant of mApple; Liu et al. (2011) Biochem. Biophys. Res. Commun. 412(1):155-159 for a description of circularly permuted variants of Venus and Citrine, Li et al. (2008) Photochem. Photobiol. 84(1):111-119 for a description of circularly permuted variants of mCherry, and Perez-Jimenez et al. (2006) J. Biol. Chem. December 29; 281(52):40010-40014 for a description of circularly permuted variants of enhanced yellow fluorescent protein (EYFP); all of which references are herein incorporated by reference in their entireties.

In one embodiment, the circularly permuted fluorophore of the fluorescent protein voltage sensor comprises a circularly permuted green fluorescent protein (cpGFP), wherein the cpGFP is inserted into an extracellular loop between S3 and S4 of the VSD. A representative amino acid sequence of a cpGFP is presented in SEQ ID NO:5. A polypeptide comprising the sequence of SEQ ID NO:5 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fluorescence intensity of the fluorescent protein voltage sensor is voltage dependent, can be used to construct a fluorescent protein voltage sensor, as described herein. In certain embodiments, the cpGFP is inserted at a position 4, 5, or 6 amino acids downstream of the C-terminal end of S3 of the VSD.

In another embodiment, the circularly permuted fluorophore of the fluorescent protein voltage sensor comprises a circularly permuted mApple (cpmApple) red fluorescent protein, wherein the cpmApple is inserted into an extracellular loop between S3 and S4 of the VSD. A representative amino acid sequence of a cpmApple is presented in SEQ ID NO:18. A polypeptide comprising the sequence of SEQ ID NO:18 or a variant thereof comprising a sequence having at least about 80-100% sequence identity thereto, including any percent identity within this range, such as 81, 82, 83, 84, 85, 86, 87, 88, 89, 90, 91, 92, 93, 94, 95, 96, 97, 98, or 99% sequence identity thereto, wherein the fluorescence intensity of the fluorescent protein voltage sensor is voltage dependent, can be used to construct a fluorescent protein voltage sensor, as described herein. In certain embodiments, the cpmApple is inserted at a position 4, 5, or 6 amino acids downstream of the C-terminal end of S3 of the VSD.

Fluorescent protein voltage sensors can be used to measure the membrane potential of any cell or any phospholipid bilayer enclosed structure. The cell can be of any cell type including, but not limited to, epithelial, endothelial, neuronal, adipose, cardiac, skeletal muscle, fibroblast, immune cells, hepatic, splenic, lung, circulating blood cells, reproductive cells, gastrointestinal, renal, bone marrow, and pancreatic cells. The cell can be from a cell line, a stem cell, or a primary cell isolated from any tissue including, but not limited to brain, heart, liver, lung, gut, stomach, fat, muscle, testes, uterus, ovary, skin, spleen, endocrine organ and bone, etc. Where the cell is maintained under in vitro conditions, conventional tissue culture conditions and methods can be used, and are known to those of skill in the art. Isolation and culture methods for various cells are well within the knowledge of one skilled in the art. The cell can be a prokaryotic cell, a eukaryotic cell, a mammalian cell, or a human cell. In certain embodiments, the cell is an excitable cell, such as a neuron, cardiac cell, or endocrine cell.

For example, fluorescent protein voltage sensors can be used to measure the membrane potential of the plasma membrane or a membrane of an intracellular organelle such as, but not limited to a mitochondrion, endoplasmic reticulum, sarcoplasmic reticulum, peroxisome, synaptic vesicle, or phagosome. Accordingly, the fluorescent protein voltage sensor may further comprise a targeting sequence (e.g., a signal peptide, prenylation sequence, or other membrane or organelle targeting sequence, or sequence targeting a particular subcellular region) to localize the fluorescent protein voltage sensor to the plasma membrane or an organelle membrane or subcellular region of a cell. Examples of plasma membrane targeting sequences include GSSKSKPK (SEQ ID NO:6), CXXL (SEQ ID NO:7), CaaX (SEQ ID NO:8) where "a" is an aliphatic amino acid, CC, CXC, and CCXX (SEQ ID NO:9). If the cell having its membrane potential monitored is a neuron, the fluorescent voltage sensor may be localized to the plasma membrane of a cell body or a projection (e.g., dendrite or axon) using a targeting sequence. Examples of neuron targeting sequences include ankyrinG-specific spectrin-binding and tail domains that bind to sites on the plasma membrane of neuronal cell bodies or axons (see, e.g., Zhang et al. (1998) J. Cell Biol. 142(6): 1571-1581; herein incorporated by reference). Examples of organelle targeting sequences include those targeting mitochondria (e.g., MLRTSSLFTRRVQPSLFRNILRLQST, SEQ ID NO:10), endoplasmic reticulum (e.g., KDEL, SEQ ID NO:11), peroxisomes (e.g., SKL), synapses (e.g., S/TDV or fusion to GAP 43, kinesin or tau). Such targeting sequences may be used to increase the concentration of fluorescent protein voltage sensors at a particular membrane of the cell.

In one embodiment, the invention includes a method for monitoring the membrane potential of a cell comprising: a) transfecting a cell with a recombinant polynucleotide encoding a fluorescent protein voltage sensor operably linked to a promoter, whereby the fluorescent voltage sensor is expressed and localizes to a membrane of the cell; and b) illuminating the cell with light at an excitation wavelength of the fluorescent protein voltage sensor; and c) monitoring the fluorescence response, wherein the intensity of the fluorescence emitted by the fluorescent protein voltage sensor is correlated with the membrane potential of the cell (e.g. decreased intensity of the fluorescence emitted by the ASAP1 fluorescent protein voltage sensor indicates depolarization). Cells may be transfected in vitro or in vivo.

In another embodiment, the invention includes a method for monitoring the membrane potential of a cell comprising: a) inserting a fluorescent voltage sensor into a membrane of the cell; b) illuminating the cell with light at an excitation wavelength of the fluorescent protein voltage sensor; and c) monitoring the fluorescence response, wherein the intensity of the fluorescence emitted by the fluorescent protein voltage sensor is correlated with the membrane potential of the cell.

In certain embodiments, the fluorescence response is monitored after exposing a cell to a stimulus. A stimulus may include anything capable of changing the membrane potential or suspected of being able to change the membrane potential of a cell. For example, a stimulus may comprise an electrical current, a drug, a ligand for a receptor, a ligand for an ion channel or transporter, a hormone, or a second messenger. In one embodiment, the membrane potential of a cell is monitored before and after exposure of the cell to the stimulus to determine the magnitude of the change in membrane potential as a result of exposure of the cell to the stimulus.

In one embodiment, the invention includes a method of screening an agent for its effect on the membrane potential of a cell, the method comprising: a) monitoring the membrane potential of the cell, according to a method described herein, before and after treatment of the cell with the agent; and b) comparing the membrane potential before and after treatment of the cell with the agent to detect any changes in the membrane potential resulting from treatment of the cell with the agent. Exemplary agents that may be screened by this method include an ion channel modulator (e.g., agonist or antagonist), an ion channel blocker, an ion channel opener, a ligand for an ion channel, transporter, or receptor, a hormone, a second messenger, or a drug or other organic or inorganic molecule suspected of affecting membrane potential.

In the practice of the invention, the fluorescence of fluorescent protein voltage sensors can be monitored by any suitable method. For example, fluorescence of fluorescent protein voltage sensors can be detected by a fluorimeter, a fluorescence microscope, a fluorescence microplate reader, a fluorometric imaging plate reader, or fluorescence-activated cell sorting. In addition, a variety of microscopy techniques known in the art may be used, including, but not limited to, confocal microscopy, two-photon excitation microscopy, light sheet microscopy, or light-field microscopy. See, e.g., *Fluorescence Microscopy: Super-Resolution and other Novel Techniques* (A. Cornea, P. M. Conn eds., Academic Press, 2014); E. H. K. Stelzer, K. Greger, and E. G. Reynaud *Light Sheet Based Fluorescence Microscopy: Principles and Practice* (Wiley-Blackwell 1$^{st}$ edition); *Handbook of Biological Confocal Microscopy* (J. Pawley ed., Springer, 3$^{rd}$ edition, 2006); *Light Microscopy: Methods and Protocols* (Methods in Molecular Biology, H. Chiarini-Garcia, R. Melo eds., Humana Press, 2011); *Confocal and Two-Photon Microscopy: Foundations, Applications and Advances* (A. Diaspro ed., Wiley-Liss, 2001); and *Cellular Imaging Techniques for Neuroscience and Beyond* (F. G. Wouterlood ed., Academic Press, 2012); herein incorporated by reference in their entireties.

B. Production of Fluorescent Protein Voltage Sensors

Fluorescent protein voltage sensors can be produced in any number of ways, all of which are well known in the art. In one embodiment, the fluorescent protein voltage sensors are generated using recombinant techniques. One of skill in the art can readily determine nucleotide sequences that encode the desired polypeptides using standard methodology and the teachings herein. Oligonucleotide probes can be devised based on the known sequences and used to probe genomic or cDNA libraries. The sequences can then be further isolated using standard techniques and, e.g., restriction enzymes employed to truncate the gene at desired portions of the full-length sequence. Similarly, sequences of interest can be isolated directly from cells and tissues containing the same, using known techniques, such as phenol extraction and the sequence further manipulated to produce the desired truncations. See, e.g., Sambrook et al., supra, for a description of techniques used to obtain and isolate DNA.

The sequences encoding polypeptides can also be produced synthetically, for example, based on the known sequences. The nucleotide sequence can be designed with the appropriate codons for the particular amino acid sequence desired. The complete sequence is generally assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311; Stemmer et al. (1995) *Gene* 164:49-53.

Recombinant techniques are readily used to clone sequences encoding polypeptides useful in the claimed fluorescent protein voltage sensors that can then be mutagenized in vitro by the replacement of the appropriate base pair(s) to result in the codon for the desired amino acid. Such a change can include as little as one base pair, effecting a change in a single amino acid, or can encompass several base pair changes. Alternatively, the mutations can be effected using a mismatched primer that hybridizes to the parent nucleotide sequence (generally cDNA corresponding to the RNA sequence), at a temperature below the melting temperature of the mismatched duplex. The primer can be made specific by keeping primer length and base composition within relatively narrow limits and by keeping the mutant base centrally located. See, e.g., Innis et al, (1990) PCR Applications: Protocols for Functional Genomics; Zoller and Smith, *Methods Enzymol.* (1983) 100:468. Primer extension is effected using DNA polymerase, the product cloned and clones containing the mutated DNA, derived by segregation of the primer extended strand, selected. Selection can be accomplished using the mutant primer as a hybridization probe. The technique is also applicable for generating multiple point mutations. See, e.g., Dalbie-McFarland et al. *Proc. Natl. Acad. Sci. USA* (1982) 79:6409.

Once coding sequences have been isolated and/or synthesized, they can be cloned into any suitable vector or replicon for expression. (See, also, Examples 1 and 2). As will be apparent from the teachings herein, a wide variety of vectors encoding modified polypeptides can be generated by creating expression constructs which operably link, in various combinations, polynucleotides encoding polypeptides having deletions or mutations therein.

Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, generally, *DNA Cloning*: Vols. I & II, supra; Sambrook et al., supra; B. Perbal, supra.

Insect cell expression systems, such as baculovirus systems, can also be used and are known to those of skill in the art and described in, e.g., Summers and Smith, *Texas Agricultural Experiment Station Bulletin No.* 1555 (1987). Materials and methods for baculovirus/insect cell expression systems are commercially available in kit form from, inter alia, Invitrogen, San Diego Calif. ("MaxBac" kit).

Plant expression systems can also be used to produce the fluorescent protein voltage sensors described herein. Generally, such systems use virus-based vectors to transfect plant cells with heterologous genes. For a description of such systems see, e.g., Porta et al., *Mol. Biotech.* (1996) 5:209-221; and Hackland et al., *Arch. Virol.* (1994) 139:1-22.

Viral systems, such as a vaccinia based infection/transfection system, as described in Tomei et al., *J. Virol.* (1993) 67:4017-4026 and Selby et al., *J. Gen. Virol.* (1993) 74:1103-1113, will also find use with the present invention. In this system, cells are first transfected in vitro with a vaccinia virus recombinant that encodes the bacteriophage T7 RNA polymerase. This polymerase displays exquisite specificity in that it only transcribes templates bearing T7 promoters. Following infection, cells are transfected with the DNA of interest, driven by a T7 promoter. The polymerase expressed in the cytoplasm from the vaccinia virus recombinant transcribes the transfected DNA into RNA that is then translated into protein by the host translational machinery. The method provides for high level, transient, cytoplasmic production of large quantities of RNA and its translation product(s).

The gene can be placed under the control of a promoter, ribosome binding site (for bacterial expression) and, optionally, an operator (collectively referred to herein as "control" elements), so that the DNA sequence encoding the desired polypeptide is transcribed into RNA in the host cell transformed by a vector containing this expression construction. The coding sequence may or may not contain a signal peptide or leader sequence. With the present invention, both the naturally occurring signal peptides and heterologous sequences can be used. Leader sequences can be removed by the host in post-translational processing. See, e.g., U.S. Pat. Nos. 4,431,739; 4,425,437; 4,338,397. Such sequences include, but are not limited to, the TPA leader, as well as the honey bee mellitin signal sequence.

Other regulatory sequences may also be desirable which allow for regulation of expression of the protein sequences relative to the growth of the host cell. Such regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector. Alternatively, the coding sequence can be cloned directly into an expression vector that already contains the control sequences and an appropriate restriction site.

In some cases it may be necessary to modify the coding sequence so that it may be attached to the control sequences with the appropriate orientation; i.e., to maintain the proper reading frame. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are well known to those skilled in the art. See, e.g., Sambrook et al., supra; *DNA Cloning*, Vols. I and II, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Vero293 cells, as well as others. Similarly, bacterial hosts such as E. coli, Bacillus subtilis, and Streptococcus spp., will find use with the present expression constructs. Yeast hosts useful in the present invention include inter alia, Saccharomyces cerevisiae, Candida albicans, Candida maltosa, Hansenula polymorphs, Kluyveromyces fragilis, Kluyveromyces lactis, Pichia guillerimondii, Pichia pastoris, Schizosaccharomyces pombe and Yarrowia lipolytica. Insect cells for use with baculovirus expression vectors include, inter alia, Aedes aegypti, Autographa californica, Bombyx mori, Drosophila melanogaster, Spodoptera frugiperda, and Trichoplusia ni.

Depending on the expression system and host selected, the fluorescent protein voltage sensors of the present invention are produced by growing host cells transformed by an expression vector described above under conditions whereby the protein of interest is expressed. The selection of the appropriate growth conditions is within the skill of the art.

In one embodiment, the transformed cells secrete the polypeptide product into the surrounding media. Certain regulatory sequences can be included in the vector to enhance secretion of the protein product, for example using a tissue plasminogen activator (TPA) leader sequence, an interferon ($\gamma$ or $\alpha$) signal sequence or other signal peptide sequences from known secretory proteins. The secreted polypeptide product can then be isolated by various techniques described herein, for example, using standard purification techniques such as but not limited to, hydroxyapatite resins, column chromatography, ion-exchange chromatography, size-exclusion chromatography, electrophoresis, HPLC, immunoadsorbent techniques, affinity chromatography, immunoprecipitation, and the like.

Alternatively, the transformed cells are disrupted, using chemical, physical or mechanical means, which lyse the cells yet keep the recombinant polypeptides substantially intact. Intracellular proteins can also be obtained by removing components from the cell wall or membrane, e.g., by the use of detergents or organic solvents, such that leakage of the polypeptides occurs. Such methods are known to those of skill in the art and are described in, e.g., Protein Purification Applications: A Practical Approach, (Simon Roe, Ed., 2001).

For example, methods of disrupting cells for use with the present invention include but are not limited to: sonication or ultrasonication; agitation; liquid or solid extrusion; heat treatment; freeze-thaw; desiccation; explosive decompression; osmotic shock; treatment with lytic enzymes including proteases such as trypsin, neuraminidase and lysozyme; alkali treatment; and the use of detergents and solvents such as bile salts, sodium dodecylsulphate, Triton, NP40 and CHAPS. The particular technique used to disrupt the cells is largely a matter of choice and will depend on the cell type in which the polypeptide is expressed, culture conditions and any pre-treatment used.

Following disruption of the cells, cellular debris is removed, generally by centrifugation, and the intracellularly produced polypeptides are further purified, using standard purification techniques such as but not limited to, column chromatography, ion-exchange chromatography, size-exclusion chromatography, electrophoresis, HPLC, immunoadsorbent techniques, affinity chromatography, immunoprecipitation, and the like.

For example, one method for obtaining the intracellular polypeptides of the present invention involves affinity purification, such as by immunoaffinity chromatography using antibodies (e.g., previously generated antibodies), or by lectin affinity chromatography. Particularly preferred lectin resins are those that recognize mannose moieties such as but not limited to resins derived from Galanthus nivalis agglutinin (GNA), Lens culinaris agglutinin (LCA or lentil lectin), Pisum sativum agglutinin (PSA or pea lectin), Narcissus pseudonarcissus agglutinin (NPA) and Allium ursinum agglutinin (AUA). The choice of a suitable affinity resin is within the skill in the art. After affinity purification, the polypeptides can be further purified using conventional techniques well known in the art, such as by any of the techniques described above.

Polypeptides can be conveniently synthesized chemically, for example by any of several techniques that are known to those skilled in the peptide art. In general, these methods employ the sequential addition of one or more amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in the sequence having the complementary (amino or carboxyl) group suitably protected, under conditions that allow for the formation of an amide linkage. The protecting group is then removed from the newly added amino acid residue and the next amino acid (suitably protected) is then added, and so forth. After the desired amino acids have been linked in the proper sequence, any remaining protecting groups (and any solid support, if solid phase synthesis techniques are used) are removed sequentially or concurrently, to render the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide. See, e.g., J. M. Stewart and J. D. Young, Solid Phase Peptide Synthesis (Pierce Chemical Co., Rockford, Ill. 1984) and G. Barany and R. B. Merrifield, The Peptides: Analysis, Synthesis, Biology, editors E. Gross and J. Meienhofer, Vol. 2, (Academic Press, New York, 1980), pp. 3-254, for solid phase peptide synthesis techniques; and M. Bodansky, Principles of Peptide Synthesis, (Springer-Verlag, Berlin 1984) and E. Gross and J. Meienhofer, Eds., The Peptides: Analysis, Synthesis, Biology, Vol. 1, for classical solution synthesis. These methods are typically used for relatively small polypeptides, i.e., up to about 50-100 amino acids in length, but are also applicable to larger polypeptides.

Typical protecting groups include t-butyloxycarbonyl (Boc), 9-fluorenylmethoxycarbonyl (Fmoc) benzyloxycarbonyl (Cbz); p-toluenesulfonyl (Tx); 2,4-dinitrophenyl; benzyl (Bzl); biphenylisopropyloxycarboxy-carbonyl, t-amyloxycarbonyl, isobornyloxycarbonyl, o-bromobenzyloxycarbonyl, cyclohexyl, isopropyl, acetyl, o-nitrophenylsulfonyl and the like.

Typical solid supports are cross-linked polymeric supports. These can include divinylbenzene cross-linked-styrene-based polymers, for example, divinylbenzene-hydroxymethylstyrene copolymers, divinylbenzene-chloromethylstyrene copolymers and divinylbenzene-benzhydrylaminopolystyrene copolymers.

Polypeptide analogs can also be chemically prepared by other methods such as by the method of simultaneous multiple peptide synthesis. See, e.g., Houghten *Proc. Natl. Acad. Sci. USA* (1985) 82:5131-5135; U.S. Pat. No. 4,631,211.

C. Nucleic Acids Encoding Fluorescent Protein Voltage Sensors

Nucleic acids encoding fluorescent protein voltage sensors can be used, for example, to produce fluorescent protein voltage sensors within a cell to allow the membrane potential of a cell of interest to be monitored. Nucleic acids described herein can be inserted into an expression vector to create an expression cassette capable of producing the fluorescent protein voltage sensors in a suitable host cell, such as an excitable cell of interest (e.g., neuron, cardiac cell, or endocrine cell). The ability of constructs to produce fluorescent protein voltage sensors with localization to a cellular membrane can be empirically determined (e.g., see Example 1 describing detection of the fluorescent protein voltage sensor, ASAP1, in plasma membranes of mammalian cells by fluorescence microscopy).

Expression cassettes typically include control elements operably linked to the coding sequence, which allow for the expression of the gene in vivo in the subject species. For example, typical promoters for mammalian cell expression include the SV40 early promoter, a CMV promoter such as the CMV immediate early promoter, the mouse mammary tumor virus LTR promoter, the adenovirus major late promoter (Ad MLP), and the herpes simplex virus promoter, among others. Other nonviral promoters, such as a promoter derived from the murine metallothionein gene, will also find use for mammalian expression. Typically, transcription termination and polyadenylation sequences will also be present, located 3' to the translation stop codon. Preferably, a sequence for optimization of initiation of translation, located 5' to the coding sequence, is also present. Examples of transcription terminator/polyadenylation signals include those derived from SV40, as described in Sambrook et al., supra, as well as a bovine growth hormone terminator sequence.

Enhancer elements may also be used herein to increase expression levels of the mammalian constructs. Examples include the SV40 early gene enhancer, as described in Dijkema et al., EMPO J. (1985) 4:761, the enhancer/promoter derived from the long terminal repeat (LTR) of the Rous Sarcoma Virus, as described in Gorman et al., Proc. Natl. Acad. Sci. USA (1982b) 79:6777 and elements derived from human CMV, as described in Boshart et al., Cell (1985) 41:521, such as elements included in the CMV intron A sequence.

Membrane targeting sequences may be used to increase levels of the expressed fluorescent protein voltage sensor at a cellular membrane (e.g., plasma membrane, organelle membrane). For example, constructs may include a sequence encoding a signal peptide, prenylation sequence, or other membrane localization sequence or organelle localization sequence. See, e.g., Saraogi et al. (2011) Traffic 12(5):535-542; Clérico et al. (2008) Biopolymers 90(3):307-319.; Luzio et al. (1993) Trends Biochem Sci. 18(10):395-398; Casey and Seabra (1996) J. Biol. Chem. 271 (10):5289-5292; Maltese (1990) FASEB J 4 (15): 3319-3328; herein incorporated by reference. By this method, expressed fluorescent voltage sensors may be localized, for example, to the plasma membrane of the cell body or a projection (e.g., dendrite or axon) of a neuron or the sarcolemma of a muscle cell.

Once complete, the constructs encoding fluorescent protein voltage sensors can be used to transfect cells in culture or be administered to a subject using standard gene delivery protocols. Genes can be delivered either directly to a subject or, alternatively, delivered ex vivo, to cells derived from the subject and the cells reimplanted in the subject. Methods for gene delivery are known in the art. See, e.g., U.S. Pat. Nos. 5,399,346, 5,580,859, 5,589,466.

A number of viral based systems have been developed for gene transfer into mammalian cells. These include adenoviruses, retroviruses (γ-retroviruses and lentiviruses), poxviruses, adeno-associated viruses, baculoviruses, and herpes simplex viruses (see e.g., Warnock et al. (2011) Methods Mol. Biol. 737:1-25; Walther et al. (2000) Drugs 60(2):249-271; and Lundstrom (2003) Trends Biotechnol. 21(3):117-122; herein incorporated by reference).

For example, retroviruses provide a convenient platform for gene delivery systems. Selected sequences can be inserted into a vector and packaged in retroviral particles using techniques known in the art. The recombinant virus can then be isolated and delivered to cells of the subject either in vivo or ex vivo. A number of retroviral systems have been described (U.S. Pat. No. 5,219,740; Miller and Rosman (1989) BioTechniques 7:980-990; Miller, A. D. (1990) Human Gene Therapy 1:5-14; Scarpa et al. (1991) Virology 180:849-852; Burns et al. (1993) Proc. Natl. Acad. Sci. USA 90:8033-8037; Boris-Lawrie and Temin (1993) Cur. Opin. Genet. Develop. 3:102-109; and Ferry et al. (2011) Curr Pharm Des. 17(24):2516-2527). Lentiviruses are a class of retroviruses that are particularly useful for delivering polynucleotides to mammalian cells because they are able to infect both dividing and nondividing cells (see e.g., Lois et al (2002) Science 295:868-872; Durand et al. (2011) Viruses 3(2):132-159; herein incorporated by reference).

A number of adenovirus vectors have also been described. Unlike retroviruses which integrate into the host genome, adenoviruses persist extrachromosomally thus minimizing the risks associated with insertional mutagenesis (Haj-Ahmad and Graham, J. Virol. (1986) 57:267-274; Bett et al., J. Virol. (1993) 67:5911-5921; Mittereder et al., Human Gene Therapy (1994) 5:717-729; Seth et al., J. Virol. (1994) 68:933-940; Barr et al., Gene Therapy (1994) 1:51-58; Berkner, K. L. BioTechniques (1988) 6:616-629; and Rich et al., Human Gene Therapy (1993) 4:461-476). Additionally, various adeno-associated virus (AAV) vector systems have been developed for gene delivery. AAV vectors can be readily constructed using techniques well known in the art. See, e.g., U.S. Pat. Nos. 5,173,414 and 5,139,941; International Publication Nos. WO 92/01070 (published 23 Jan. 1992) and WO 93/03769 (published 4 Mar. 1993); Lebkowski et al., Molec. Cell. Biol. (1988) 8:3988-3996; Vincent et al., Vaccines 90 (1990) (Cold Spring Harbor Laboratory Press); Carter, B. J. Current Opinion in Biotechnology (1992) 3:533-539; Muzyczka, N. Current Topics in Microbiol. and Immunol. (1992) 158:97-129; Kotin, R. M. Human Gene Therapy (1994) 5:793-801; Shelling and Smith, Gene Therapy (1994) 1:165-169; and Zhou et al., J. Exp. Med. (1994) 179:1867-1875.

Another vector system useful for delivering the polynucleotides of the present invention is the enterically administered recombinant poxvirus vaccines described by Small, Jr., P. A., et al. (U.S. Pat. No. 5,676,950, issued Oct. 14, 1997, herein incorporated by reference).

Additional viral vectors which will find use for delivering the nucleic acid molecules encoding the fluorescent protein voltage sensors include those derived from the pox family of viruses, including vaccinia virus and avian poxvirus. By way of example, vaccinia virus recombinants expressing the fluorescent protein voltage sensors can be constructed as follows. The DNA encoding the particular fluorescent protein voltage sensor coding sequence is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the coding sequences of interest into the viral genome. The resulting TK-recombinant can be selected by culturing the cells in the presence of 5-bromodeoxyuridine and picking viral plaques resistant thereto.

Alternatively, avipoxviruses, such as the fowlpox and canarypox viruses, can also be used to deliver the genes. Recombinant avipox viruses, expressing immunogens from mammalian pathogens, are known to confer protective immunity when administered to non-avian species. The use of an avipox vector is particularly desirable in human and other mammalian species since members of the avipox genus can only productively replicate in susceptible avian species and therefore are not infective in mammalian cells. Methods for producing recombinant avipoxviruses are known in the art and employ genetic recombination, as described above with. respect to the production of vaccinia viruses. See, e.g., WO 91/12882; WO 89/03429; and WO 92/03545.

Molecular conjugate vectors, such as the adenovirus chimeric vectors described in Michael et al., J. Biol. Chem. (1993) 268:6866-6869 and Wagner et al., Proc. Natl. Acad. Sci. USA (1992) 89:6099-6103, can also be used for gene delivery.

Members of the Alphavirus genus, such as, but not limited to, vectors derived from the Sindbis virus (SIN), Semliki Forest virus (SFV), and Venezuelan Equine Encephalitis virus (VEE), will also find use as viral vectors for delivering the polynucleotides of the present invention. For a description of Sindbis-virus derived vectors useful for the practice of the instant methods, see, Dubensky et al. (1996) J. Virol. 70:508-519; and International Publication Nos. WO 95/07995, WO 96/17072; as well as, Dubensky, Jr., T. W., et al., U.S. Pat. No. 5,843,723, issued Dec. 1, 1998, and Dubensky, Jr., T. W., U.S. Pat. No. 5,789,245, issued Aug. 4, 1998, both herein incorporated by reference. Particularly preferred are chimeric alphavirus vectors comprised of sequences derived from Sindbis virus and Venezuelan equine encephalitis virus. See, e.g., Perri et al. (2003) J. Virol. 77: 10394-10403 and International Publication Nos. WO 02/099035, WO 02/080982, WO 01/81609, and WO 00/61772; herein incorporated by reference in their entireties.

A vaccinia based infection/transfection system can be conveniently used to provide for inducible, transient expression of the coding sequences of interest (for example, a fluorescent protein voltage sensor expression cassette) in a host cell. In this system, cells are first infected in vitro with a vaccinia virus recombinant that encodes the bacteriophage T7 RNA polymerase. This polymerase displays exquisite specificity in that it only transcribes templates bearing T7 promoters. Following infection, cells are transfected with the polynucleotide of interest, driven by a T7 promoter. The polymerase expressed in the cytoplasm from the vaccinia virus recombinant transcribes the transfected DNA into RNA which is then translated into protein by the host translational machinery. The method provides for high level, transient, cytoplasmic production of large quantities of RNA and its translation products. See, e.g., Elroy-Stein and Moss, Proc. Natl. Acad. Sci. USA (1990) 87:6743-6747; Fuerst et al., Proc. Natl. Acad. Sci. USA (1986) 83:8122-8126.

As an alternative approach to infection with vaccinia or avipox virus recombinants, or to the delivery of genes using other viral vectors, an amplification system can be used that will lead to high level expression following introduction into host cells. Specifically, a T7 RNA polymerase promoter preceding the coding region for T7 RNA polymerase can be engineered. Translation of RNA derived from this template will generate T7 RNA polymerase which in turn will transcribe more template. Concomitantly, there will be a cDNA whose expression is under the control of the T7 promoter. Thus, some of the T7 RNA polymerase generated from translation of the amplification template RNA will lead to transcription of the desired gene. Because some T7 RNA polymerase is required to initiate the amplification, T7 RNA polymerase can be introduced into cells along with the template(s) to prime the transcription reaction. The polymerase can be introduced as a protein or on a plasmid encoding the RNA polymerase. For a further discussion of T7 systems and their use for transforming cells, see, e.g., International Publication No. WO 94/26911; Studier and Moffatt, J. Mol. Biol. (1986) 189:113-130; Deng and Wolff, Gene (1994) 143:245-249; Gao et al., Biochem. Biophys. Res. Commun. (1994) 200:1201-1206; Gao and Huang, Nuc. Acids Res. (1993) 21:2867-2872; Chen et al., Nuc. Acids Res. (1994) 22:2114-2120; and U.S. Pat. No. 5,135,855.

The synthetic expression cassette of interest can also be delivered without a viral vector. For example, the synthetic expression cassette can be packaged as DNA or RNA in liposomes prior to delivery to the subject or to cells derived therefrom. Lipid encapsulation is generally accomplished using liposomes which are able to stably bind or entrap and retain nucleic acid. The ratio of condensed DNA to lipid preparation can vary but will generally be around 1:1 (mg DNA:micromoles lipid), or more of lipid. For a review of the use of liposomes as carriers for delivery of nucleic acids, see, Hug and Sleight, Biochim. Biophys. Acta. (1991.) 1097:1-17; Straubinger et al., in Methods of Enzymology (1983), Vol. 101, pp. 512-527.

Liposomal preparations for use in the present invention include cationic (positively charged), anionic (negatively charged) and neutral preparations, with cationic liposomes particularly preferred. Cationic liposomes have been shown to mediate intracellular delivery of plasmid DNA (Felgner et al., Proc. Natl. Acad. Sci. USA (1987) 84:7413-7416); mRNA (Malone et al., Proc. Natl. Acad. Sci. USA (1989) 86:6077-6081); and purified transcription factors (Debs et al., J. Biol. Chem. (1990) 265:10189-10192), in functional form.

Cationic liposomes are readily available. For example, N[1-2,3-dioleyloxy)propyl]-N,N,N-triethylammonium (DOTMA) liposomes are available under the trademark Lipofectin, from GIBCO BRL, Grand Island, N.Y. (See, also, Felgner et al., Proc. Natl. Acad. Sci. USA (1987) 84:7413-7416). Other commercially available lipids include (DDAB/DOPE) and DOTAP/DOPE (Boerhinger). Other cationic liposomes can be prepared from readily available materials using techniques well known in the art. See, e.g., Szoka et al., Proc. Natl. Acad. Sci. USA (1978) 75:4194-4198; PCT Publication No. WO 90/11092 for a description of the synthesis of DOTAP (1,2-bis(oleoyloxy)-3-(trimethylammonio)propane) liposomes.

Similarly, anionic and neutral liposomes are readily available, such as, from Avanti Polar Lipids (Birmingham, Ala.), or can be easily prepared using readily available materials.

Such materials include phosphatidyl choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

The liposomes can comprise multilammelar vesicles (MLVs), small unilamellar vesicles (SUVs), or large unilamellar vesicles (LUVs). The various liposome-nucleic acid complexes are prepared using methods known in the art. See, e.g., Straubinger et al., in METHODS OF IMMUNOLOGY (1983), Vol. 101, pp. 512-527; Szoka et al., Proc. Natl. Acad. Sci. USA (1978) 75:4194-4198; Papahadjopoulos et al., Biochim. Biophys. Acta (1975) 394:483; Wilson et al., Cell (1979) 17:77); Deamer and Bangham, Biochim. Biophys. Acta (1976) 443:629; Ostro et al., Biochem. Biophys. Res. Commun. (1977) 76:836; Fraley et al., Proc. Natl. Acad. Sci. USA (1979) 76:3348); Enoch and Strittmatter, Proc. Natl. Acad. Sci. USA (1979) 76:145); Fraley et al., J. Biol. Chem. (1980) 255:10431; Szoka and Papahadjopoulos, Proc. Natl. Acad. Sci. USA (1978) 75:145; and Schaefer-Ridder et al., Science (1982) 215:166.

The DNA and/or peptide(s) can also be delivered in cochleate lipid compositions similar to those described by Papahadjopoulos et al., Biochim. Biophys. Acta. (1975) 394:483-491. See, also, U.S. Pat. Nos. 4,663,161 and 4,871,488.

The expression cassette of interest may also be encapsulated, adsorbed to, or associated with, particulate carriers. Examples of particulate carriers include those derived from polymethyl methacrylate polymers, as well as microparticles derived from poly(lactides) and poly(lactide-co-glycolides), known as PLG. See, e.g., Jeffery et al., Pharm. Res. (1993) 10:362-368; McGee J. P., et al., J. Microencapsul. 14(2): 197-210, 1997; O'Hagan D. T., et al., Vaccine 11(2):149-54, 1993.

Furthermore, other particulate systems and polymers can be used for the in vivo or ex vivo delivery of the nucleic acid of interest. For example, polymers such as polylysine, polyarginine, polyornithine, spermine, spermidine, as well as conjugates of these molecules, are useful for transferring a nucleic acid of interest. Similarly, DEAE dextran-mediated transfection, calcium phosphate precipitation or precipitation using other insoluble inorganic salts, such as strontium phosphate, aluminum silicates including bentonite and kaolin, chromic oxide, magnesium silicate, talc, and the like, will find use with the present methods. See, e.g., Felgner, P. L., Advanced Drug Delivery Reviews (1990) 5:163-187, for a review of delivery systems useful for gene transfer. Peptoids (Zuckerman, R. N., et al., U.S. Pat. No. 5,831,005, issued Nov. 3, 1998, herein incorporated by reference) may also be used for delivery of a construct of the present invention.

Additionally, biolistic delivery systems employing particulate carriers such as gold and tungsten, are especially useful for delivering synthetic expression cassettes of the present invention. The particles are coated with the synthetic expression cassette(s) to be delivered and accelerated to high velocity, generally under a reduced atmosphere, using a gun powder discharge from a "gene gun." For a description of such techniques, and apparatuses useful therefore, see, e.g., U.S. Pat. Nos. 4,945,050; 5,036,006; 5,100,792; 5,179,022; 5,371,015; and 5,478,744. Also, needle-less injection systems can be used (Davis, H. L., et al, Vaccine 12:1503-1509, 1994; Bioject, Inc., Portland, Oreg.).

Recombinant vectors carrying a synthetic expression cassette of the present invention are formulated into compositions for delivery to a cell or subject.

The compositions will generally include one or more physiologically acceptable excipients or vehicles such as water, saline, glycerol, polyethyleneglycol, hyaluronic acid, ethanol, etc. Additionally, auxiliary substances, such as wetting or emulsifying agents, pH buffering substances, surfactants and the like, may be present in such vehicles. Certain facilitators of nucleic acid uptake and/or expression can also be included in the compositions or coadministered.

Once formulated, the compositions of the invention can be administered directly to a subject (e.g., as described above) or, alternatively, delivered ex vivo, to cells derived from the subject, using methods such as those described above. For example, methods for the ex vivo delivery and reimplantation of transformed cells into a subject are known in the art and can include, e.g., dextran-mediated transfection, calcium phosphate precipitation, polybrene mediated transfection, lipofectamine and LT-1 mediated transfection, protoplast fusion, electroporation, encapsulation of the polynucleotide(s) in liposomes, and direct microinjection of the DNA into nuclei.

Direct delivery of synthetic expression cassette compositions in vivo will generally be accomplished with or without viral vectors, as described above, by injection using either a conventional syringe, needless devices such as Bioject™ or a gene gun, such as the Accell™ gene delivery system (PowderMed Ltd, Oxford, England).

D. Kits

Fluorescent protein voltage sensors or nucleic acids encoding them can be provided in kits with suitable instructions and other necessary reagents for preparing or using the fluorescent protein voltage sensors, as described above. The kit may contain in separate containers fluorescent protein voltage sensors, or recombinant constructs for producing fluorescent protein voltage sensors, and/or cells (either already transfected or separate). Additionally, instructions (e.g., written, tape, VCR, CD-ROM, DVD, etc.) for using the fluorescent protein voltage sensors to monitor membrane potential may be included in the kit. The kit may also contain other packaged reagents and materials (e.g., transfection reagents, buffers, media, and the like).

In certain embodiments, the kit comprises a fluorescent protein voltage sensor comprising an amino acid sequence selected from the group consisting of SEQ ID NOS:1-3 and SEQ ID NOS:13-17.

In other embodiments, the kit comprises a recombinant polynucleotide comprising a polynucleotide selected from the group consisting of: a) a polynucleotide comprising the nucleotide sequence of SEQ ID NO:12; b) a polynucleotide comprising a nucleotide sequence at least 95% identical to the nucleotide sequence of SEQ ID NO:12, wherein the fluorescence intensity of the encoded polypeptide is voltage dependent; c) a polynucleotide encoding a polypeptide comprising an amino acid sequence selected from the group consisting of SEQ ID NOS:1-3 and SEQ ID NOS:13-17; and d) a polynucleotide encoding a polypeptide comprising a sequence at least 95% identical to an amino acid sequence selected from the group consisting of SEQ ID NOS:1-3 and SEQ ID NOS:13-17, wherein the fluorescence intensity of the polypeptide is voltage dependent.

E. Applications

The fluorescent protein voltage sensors of the invention provide useful tools for measuring membrane potential of cells with the convenience of allowing electrical activity to be monitored optically. They can be used for a variety purposes, including, for example, measuring membrane potential of any cell and, in particular, excitable cells of interest, such as neurons, cardiac cells and endocrine cells; imaging electrical activity of cells, including high-frequency neuronal electrical activity (e.g., trains of action potentials); and screening agents that target ion channels, transporters, or receptors for their effects on membrane potential. Thus, fluorescent protein voltage sensors should find numerous applications in basic research and development.

For example, optical imaging of neural activity with fluorescent protein voltage sensors will be useful in the study and development of treatments for brain disorders. As shown in Example 1, fluorescent protein voltage sensors have sufficient sensitivity to enable monitoring of hyperpolarizations, subthreshold depolarizations and individual action potentials (APs) in neurons, and their rapid kinetics permit detection of rapid trains of action potentials, including action potential waveforms having a frequency of up to 200 Hz. The methods of the invention can be used for mapping brain activity in patients and/or cells of patients with psychiatric and neurological diseases, victims of traumatic injuries, or animal models of neurological disorders. Optical imaging of neuronal activity with fluorescent protein voltage sensors may also aid in improving brain-machine interfaces for people with disabilities.

Fluorescent protein voltage sensors will also be useful in pharmaceutical screening to identify agents that affect membrane potential. The methods of the invention can be used, for example, to screen for ion channel modulators or in toxicity screening to identify drugs with adverse effects on membrane potential. Such screening methods can be performed in a high throughput manner by simultaneously screening multiple agents in cells. In particular, these methods will be applicable for testing drugs targeting the nervous system or heart.

III. EXPERIMENTAL

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Example 1

A Genetically Encoded Voltage Sensor with Fast Kinetics for Imaging High-Frequency Neuronal Electrical Activity Introduction Accurate optical reporting of electrical activity in genetically defined neuronal populations is a longstanding goal in neuroscience. Here we describe Allosteric Sensor for Action Potentials 1 (ASAP1), a novel voltage sensor design in which a circularly permuted green fluorescent protein is inserted within an extracellular loop of a domain derived from a chicken voltage-sensitive phosphatase. ASAP1 demonstrates on- and off-kinetics of 2.05 milliseconds and 1.98 milliseconds, reliably detects single action potentials and subthreshold potential changes, and tracks trains of action potential waveforms up to 200 Hz in single trials.

Results

Figure 4A:
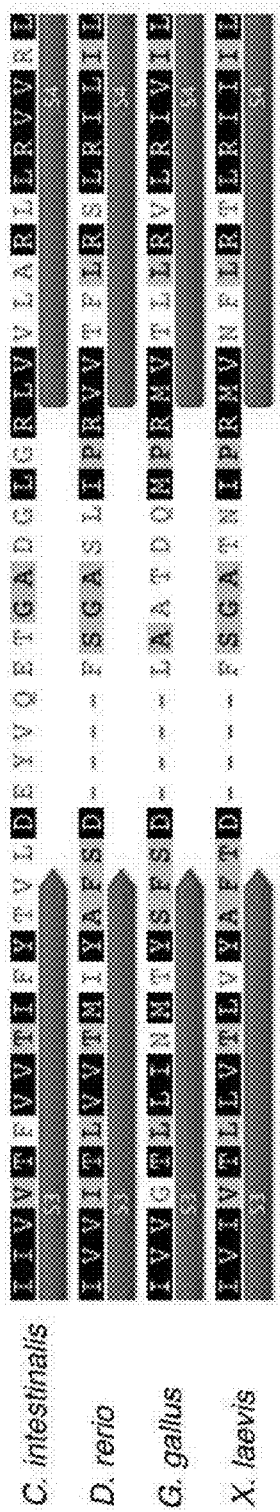
FIGS. 4A-4D show the development of ASAP-class voltage sensors.

We sought to develop a voltage sensor with sufficient brightness, dynamic range and kinetics for detection of neuronal activity from subthreshold potentials to rapid trains of action potentials. An extracellular loop between the third (S3) and fourth (S4) transmembrane segments of voltage-gated potassium channels is thought to undergo substantial conformational changes upon depolarization (Jensen et al. (2012) Science 336:229-233). A fluorescent voltage sensor can be created by insertion of a circularly permuted GFP (cpGFP) into this extracellular loop. Most voltage sensors derived from voltage sensitive phosphatases (VSP) (Kurokawa et al. (2012) Proc. Natl. Acad. Sci. U.S.A. 109:10089-10094) use a VSD from the seasquirt *Ciona intestinalis*. Instead, we chose a VSD from chicken (*Gallus gallus*, abbreviated Gg) as an initial candidate VSD because it has a shorter S3-S4 loop (FIG. 4A), which we hypothesized would aid in transducing voltage-induced movements. We constructed and tested fusions of the circularly permuted GFP (cpGFP) from GCaMP3 (Tian et al. (2009) Nat. Methods 6:875-881) to the chicken voltage sensing domain (GgVSD), with the goal of finding a protein where movements in the S4 helix of the VSD upon voltage changes would affect the GFP fluorescence via allostery. Our initial VSD included a R153Q mutation previously shown to shift the voltage response of *Ciona intestinalis* VSPs to a less negative range of potentials (Dimitrov et al. (2007) PLoS One 2:e440).

Figure 4B:
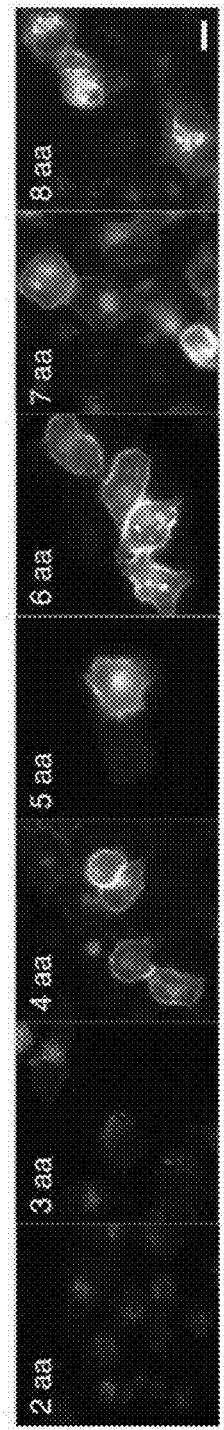
Figure 4C:
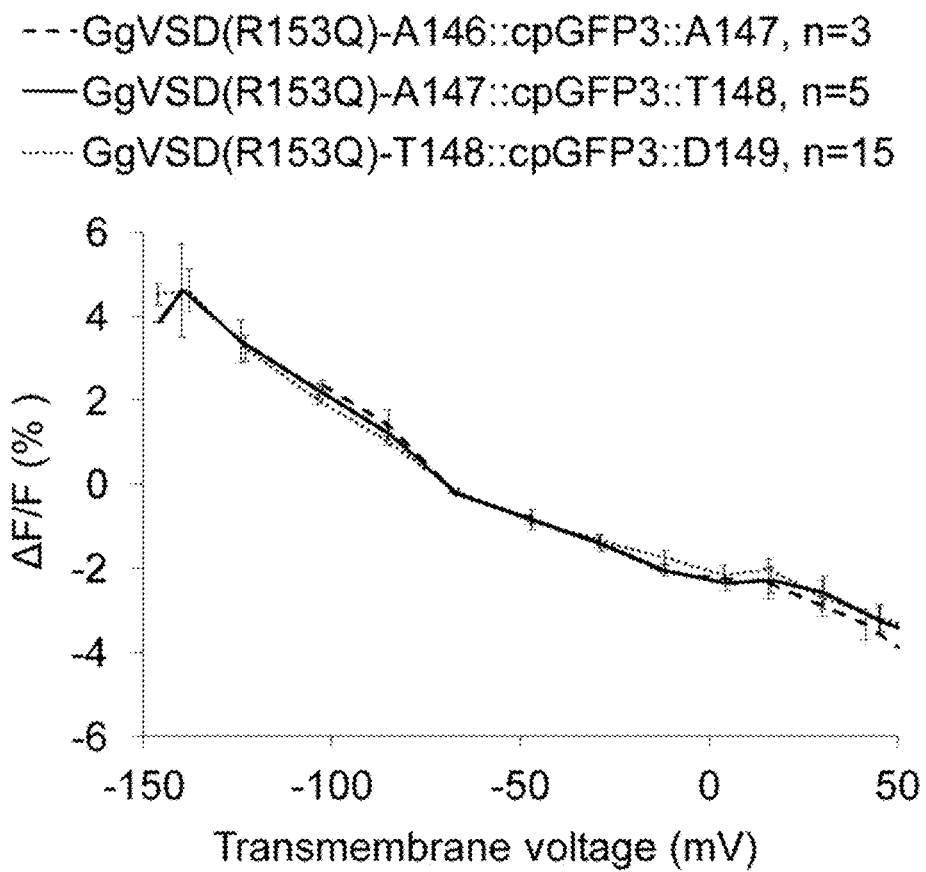
Figure 4D:
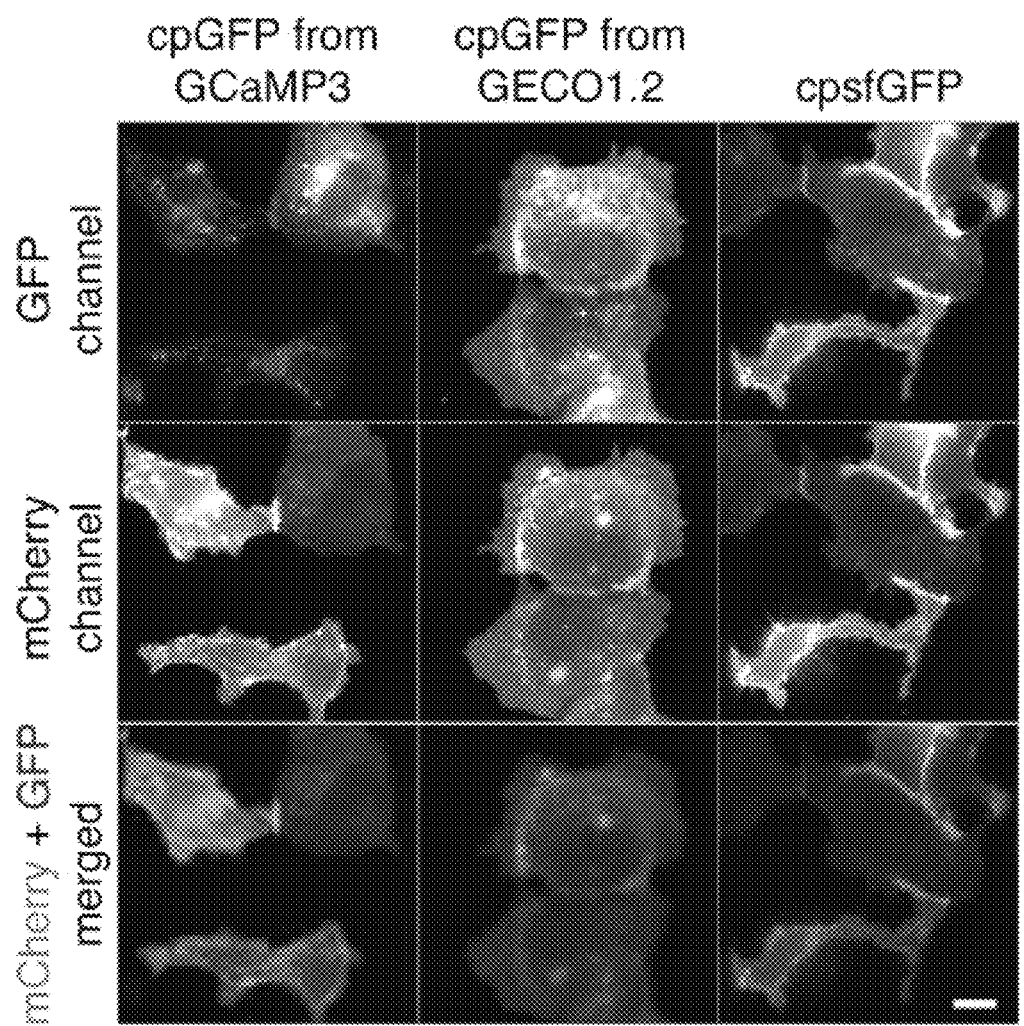

Insertion of cpGFP into the S3-S4 loop of the VSD yielded some constructs that were well expressed at the plasma membrane of mammalian cells (FIG. 4B) and showed a fluorescence decrease in response to membrane depolarization (FIG. 4C). This fluorescence decrease may reflect perturbation of beta-barrel interactions with the chromophore maintaining its deprotonation state, and would support the hypothesis that the S3-S4 linker undergoes a transition from an unstructured to an alpha-helical state upon depolarization, as suggested by molecular dynamics simulations of VSD motions (Jensen et al. (2012) Science 336: 229-233). Beginning with the brightest variant, where cpGFP was inserted between residues 147 and 148 of GgVSD, we tested substitutions of various fluorescent proteins (FIG. 4D), and found that a circularly permuted superfolder GFP variant (Pedelacq et al. (2006) Nat. Biotechnol. 24:79-88) (cpsfGFP) improved both brightness and dynamic range while maintaining efficient expression at the membrane in HEK293 cells. We named this protein Allosteric Sensor for Action Potentials 1 (ASAP1). Its basic design is depicted in FIG. 1A.

Figure 5A:
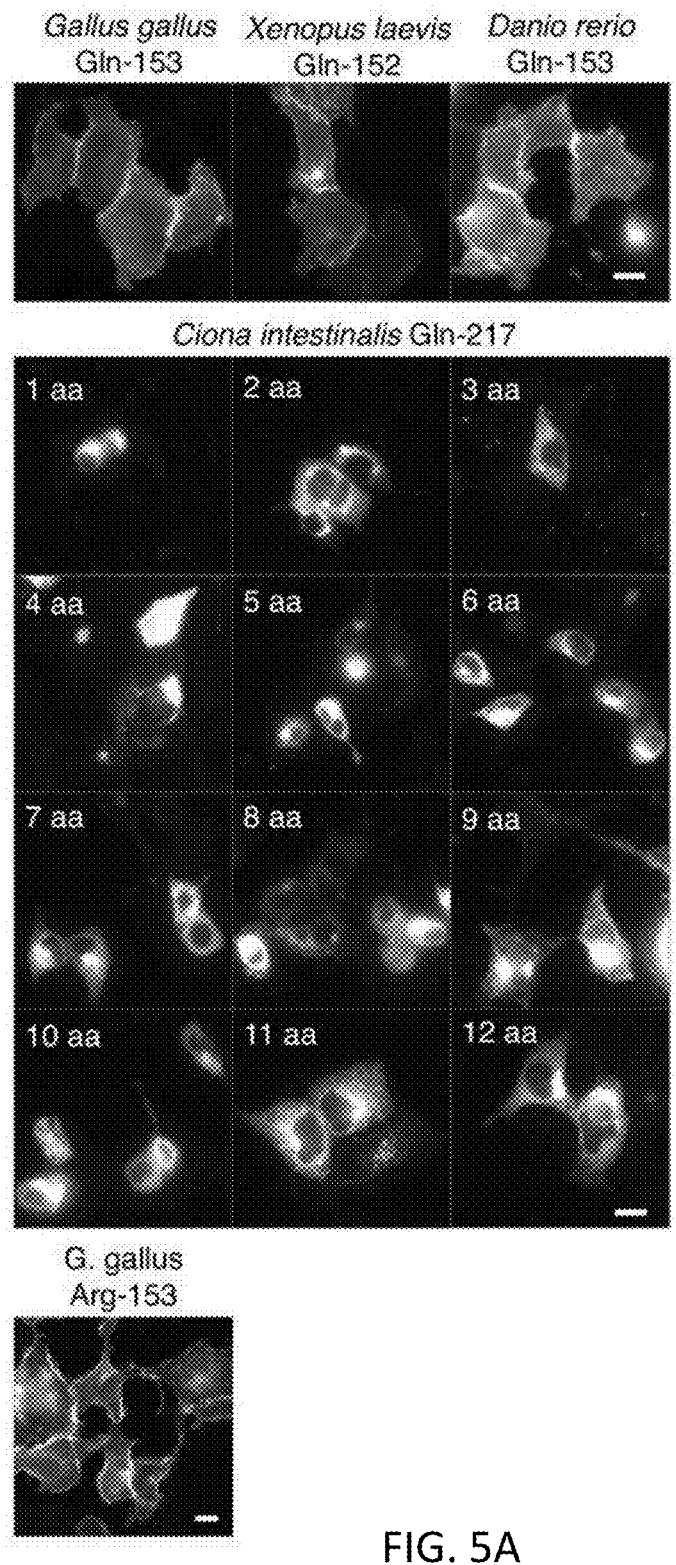
FIGS. 5A-5C show the reduced dynamic range in ASAP variants with alternative voltage sensitive domains (VSDs).
Figure 5B:
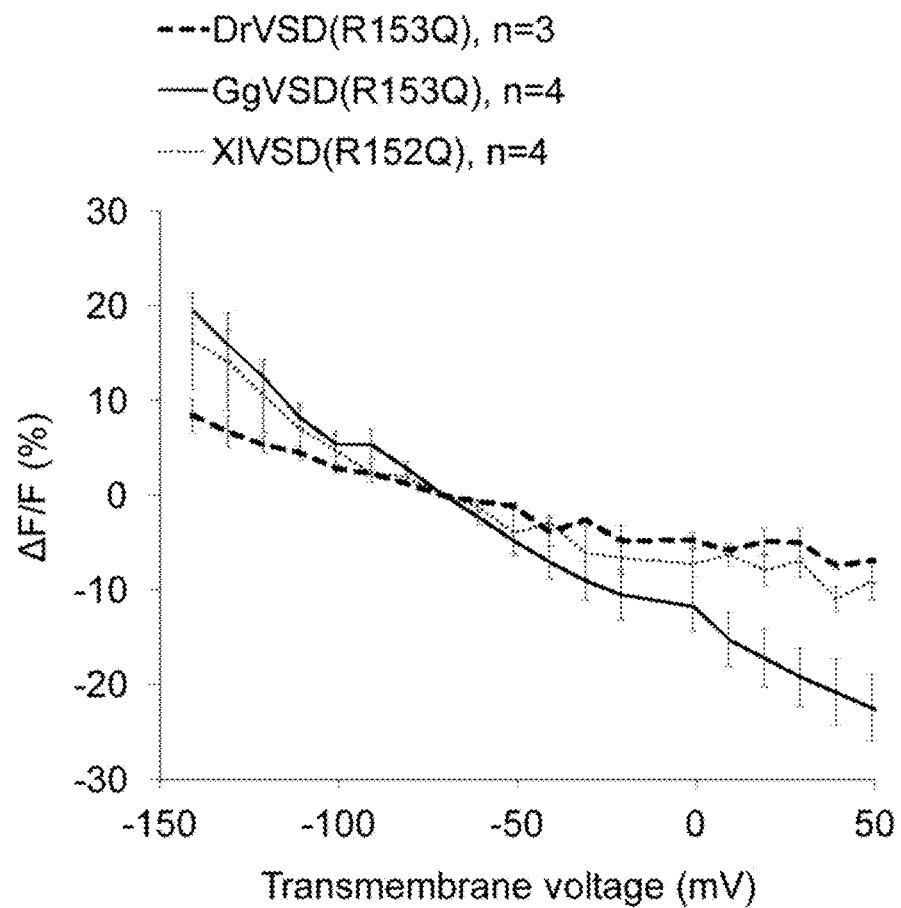
Figure 5C:
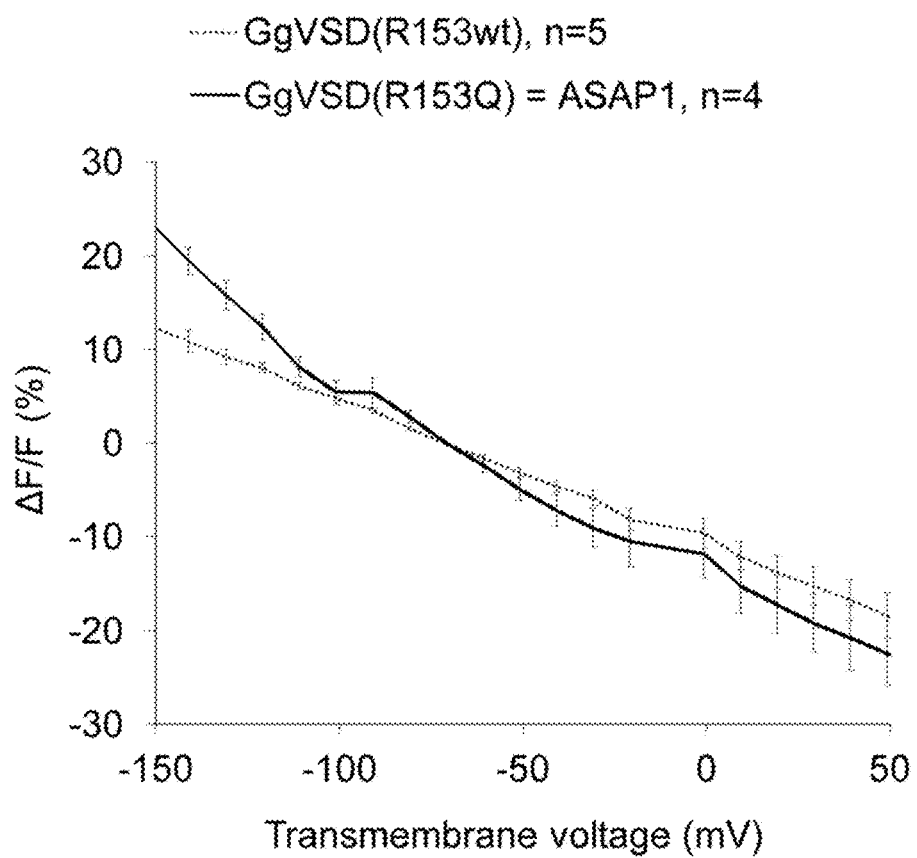
Figure 6A:
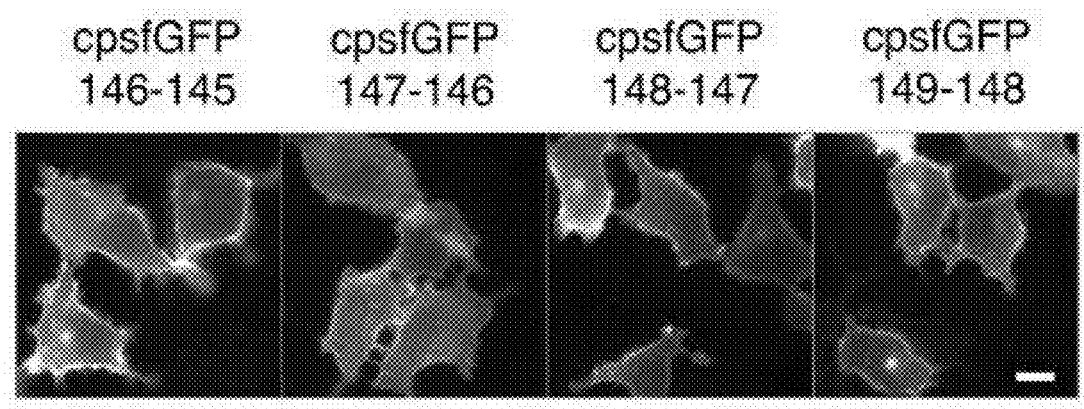
FIGS. 6A-6E show the voltage response characteristics and membrane localization of ASAP1 variants with different VSD-GFP junctions.
Figure 6B:
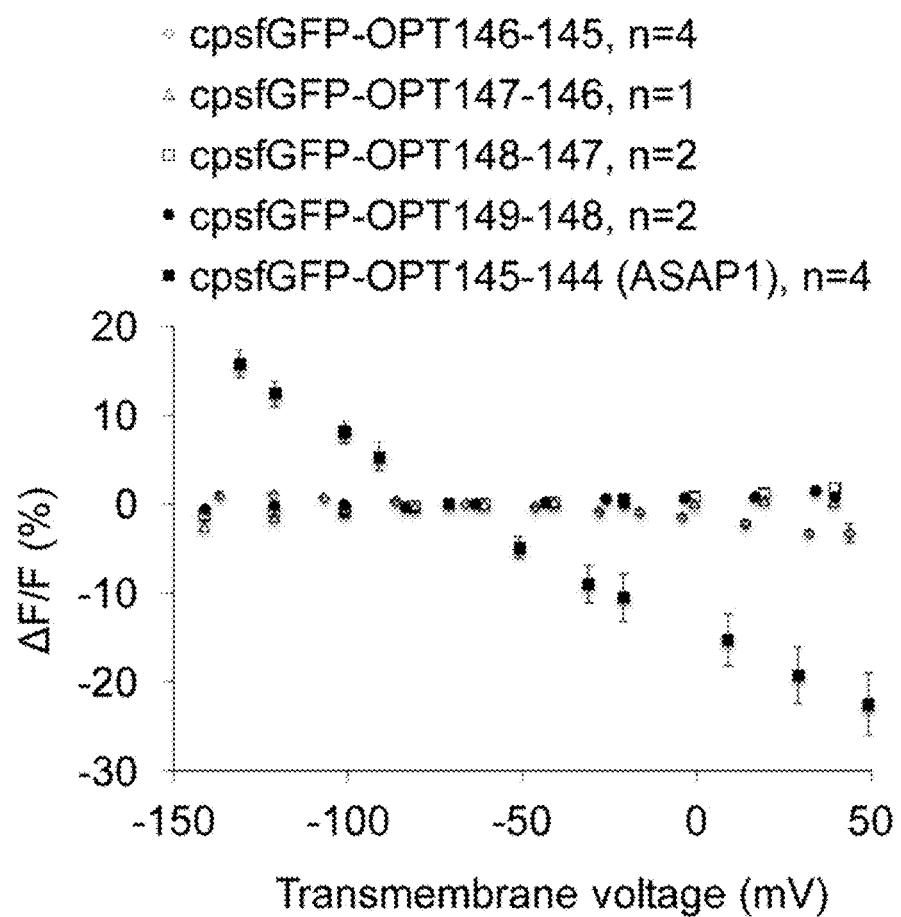
Figure 6C:
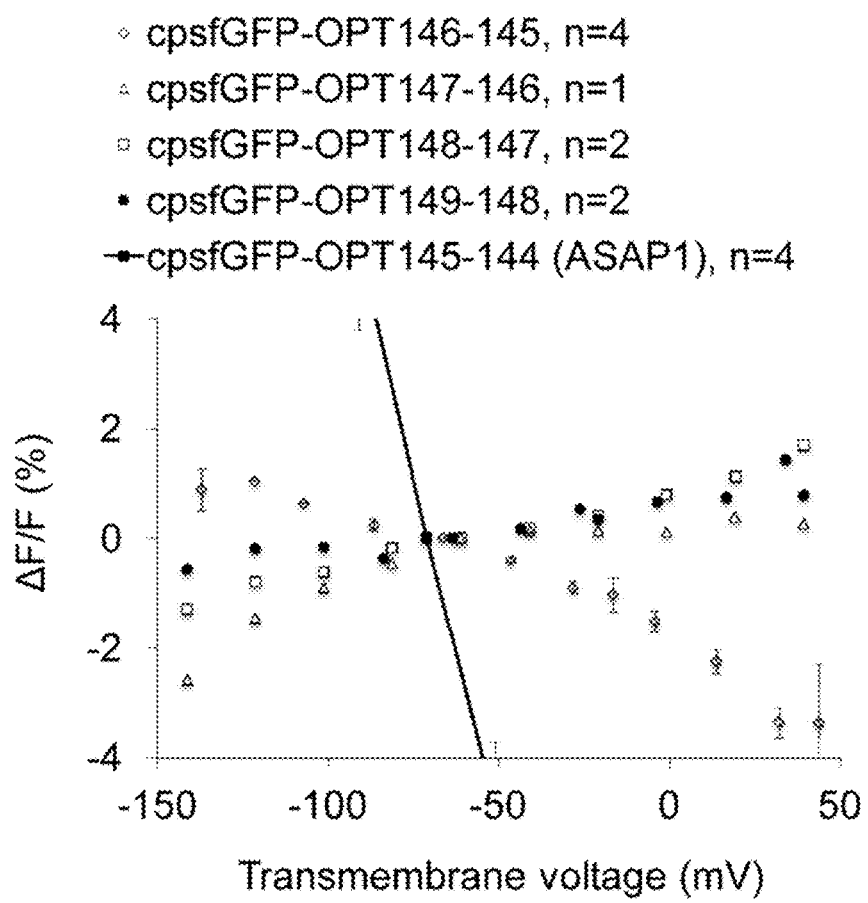
Figure 6D:
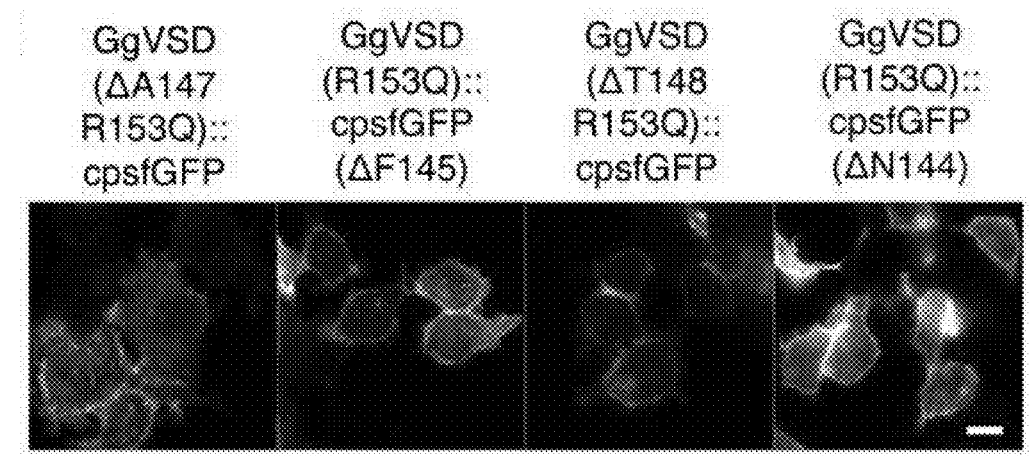
Figure 6E:
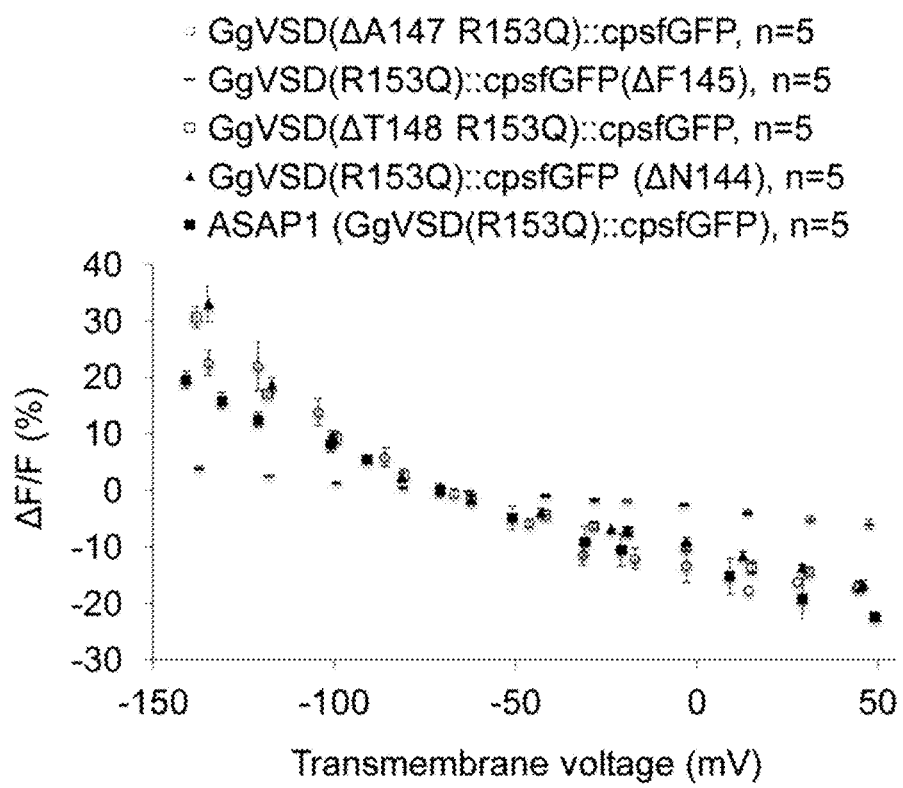
Figure 7A:
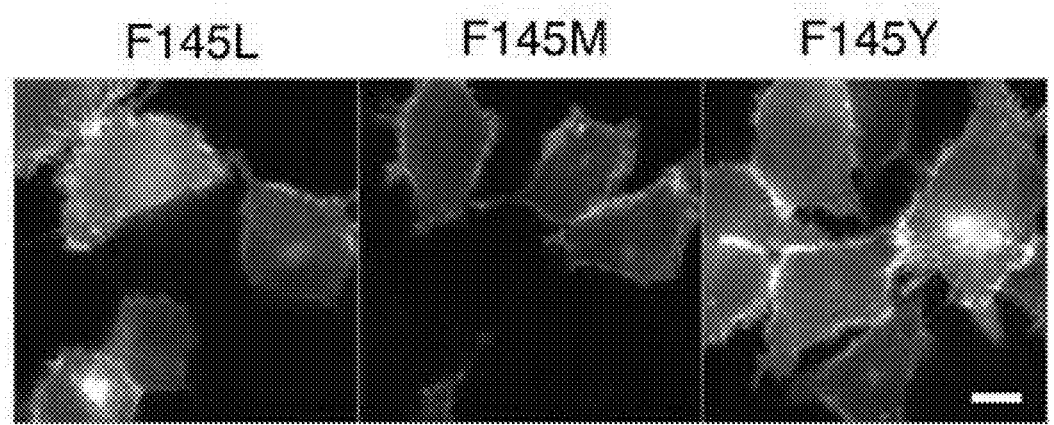
FIGS. 7A and 7B show the voltage response characteristics and membrane localization of ASAP1 variants with conservative mutations at the cspfGFP-OPT amino terminus.
Figure 7B:
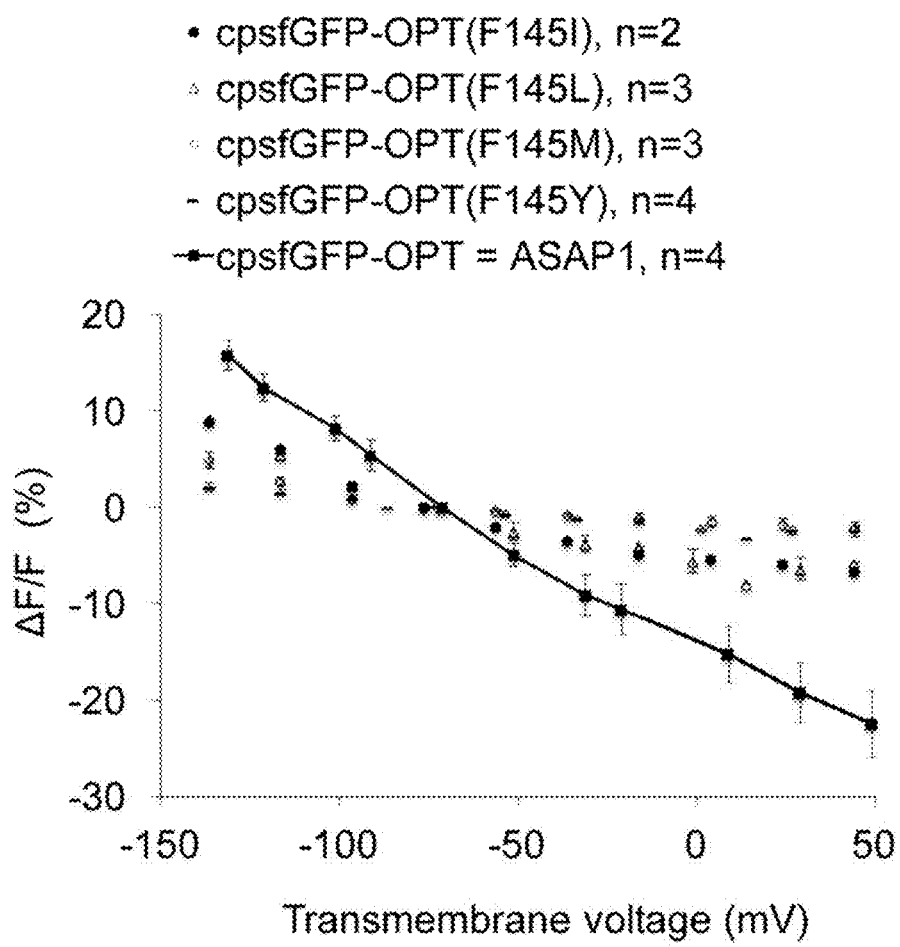

Given the diversity of voltage sensitive phosphatases (VSP), we wondered whether VSDs extracted from other VSPs might produce voltage sensors with different performance characteristics. Substituting VSDs from *Danio rerio* or *Xenopus laevis* produced voltage sensors with satisfactory expression but lowered dynamic range (FIGS. 5A and 5B). Sensors containing the VSD from *Ciona intestinalis* did not fold or localize to the plasma membrane, demonstrating that VSDs from distinct species differentially support insertion of FPs in their S3-S4 loop segment (FIG. 5A). Reversion of the R153Q mutation did not affect expression but lowered the fluorescence response (FIGS. 5A and 5C). Modifying the circular permutation breakpoint in GFP reduced the response amplitude, although interestingly some variants had inverted responses (FIGS. 6A-6C). Removing the last residue of cpsfGFP N-terminal to the junction site had no effect, whereas removal of the first residue of cpsfGFP (Phe-145 in the original GFP numbering) immediately following the junction severely reduced response (FIGS. 6D-6E). Certain conservative mutations of Phe145 also reduced dynamic range (FIG. 7). Notably, mutation of Phe-145 to Tyr reduced dynamic range, consistent with the smaller response amplitude of our initial sensors using cpGFP from GCaMP3, which contains Tyr-145. These results suggest that the modulation of cpsfGFP by voltage is sensitive to the structure near the breakpoint, as previously seen with calcium sensors based on circularly permuted fluorescent proteins (Akerboom et al. (2012) J. Neurosci. 32:13819-13840; Akerboom et al. (2013) Front. Mol. Neurosci. 6:2). In particular, they suggest that cpsfGFP responds to a conformational change on the S3 side of the linker.

Figure 1B:
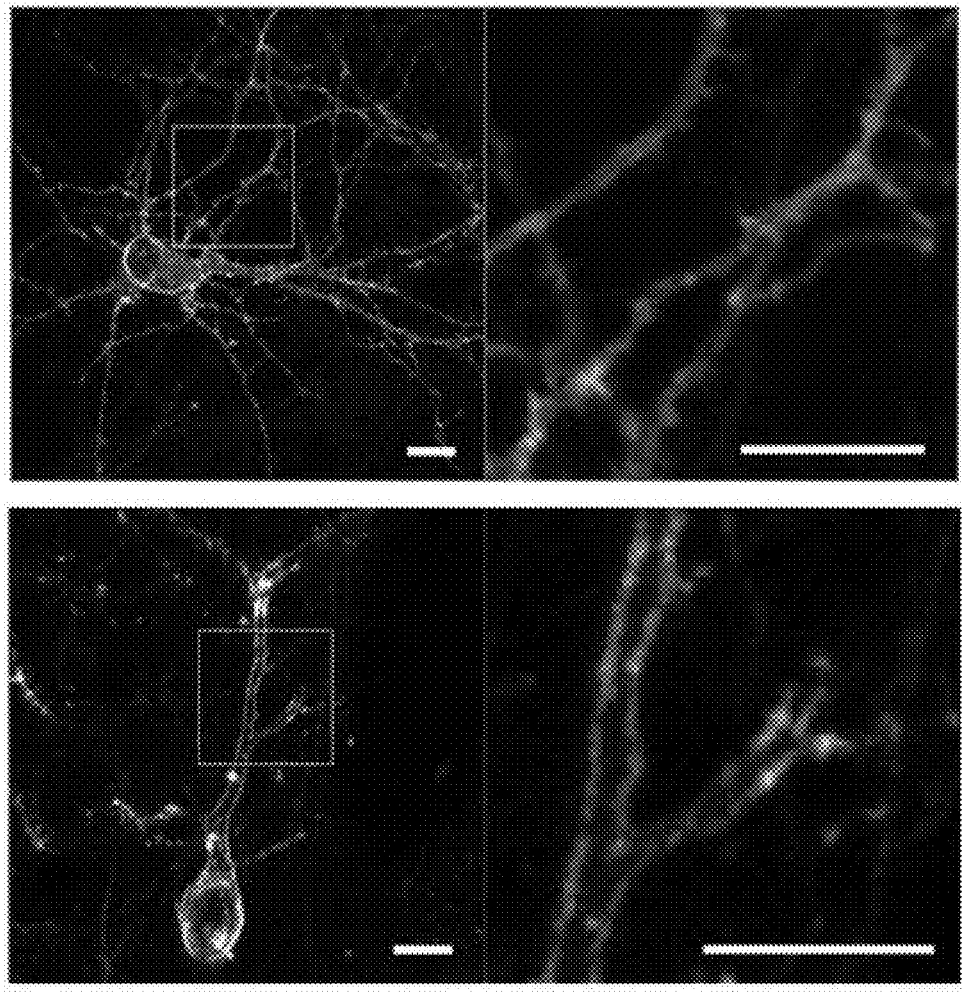
Figure 1C:
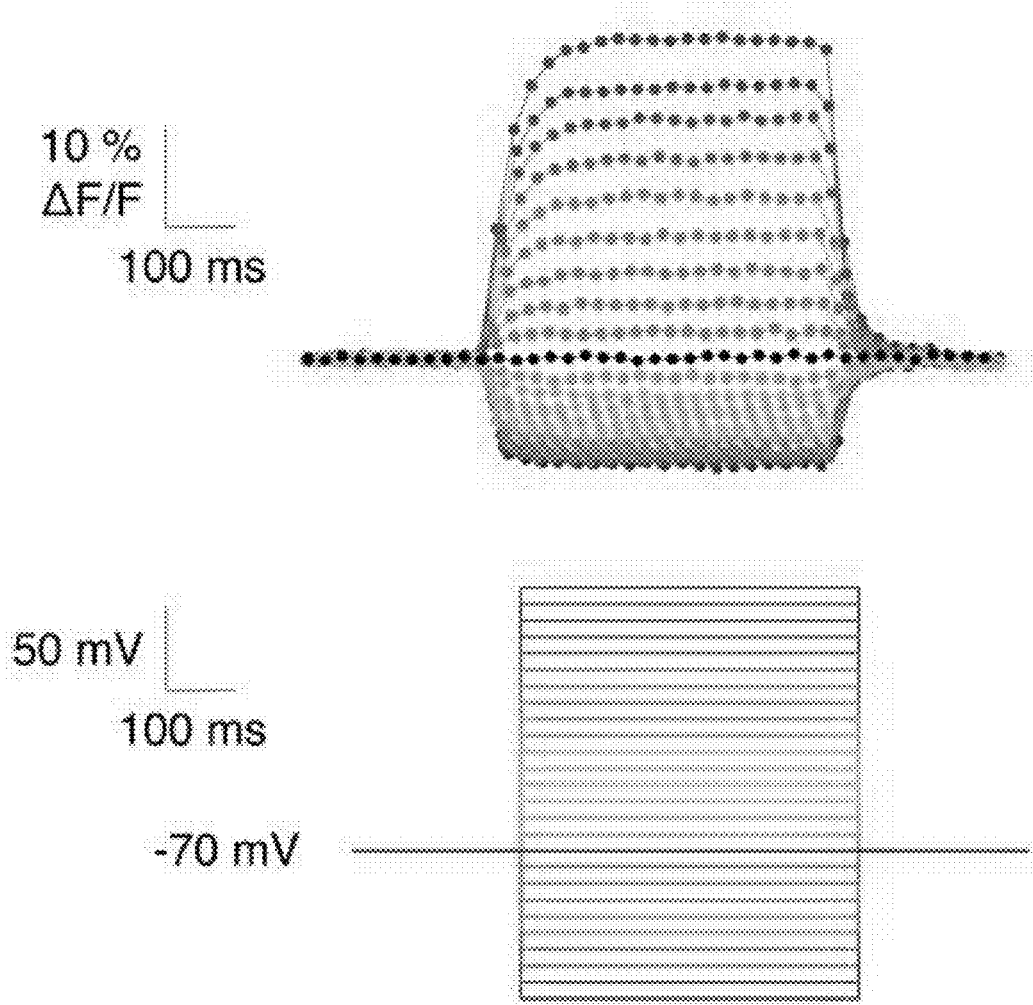
Figure 1D:
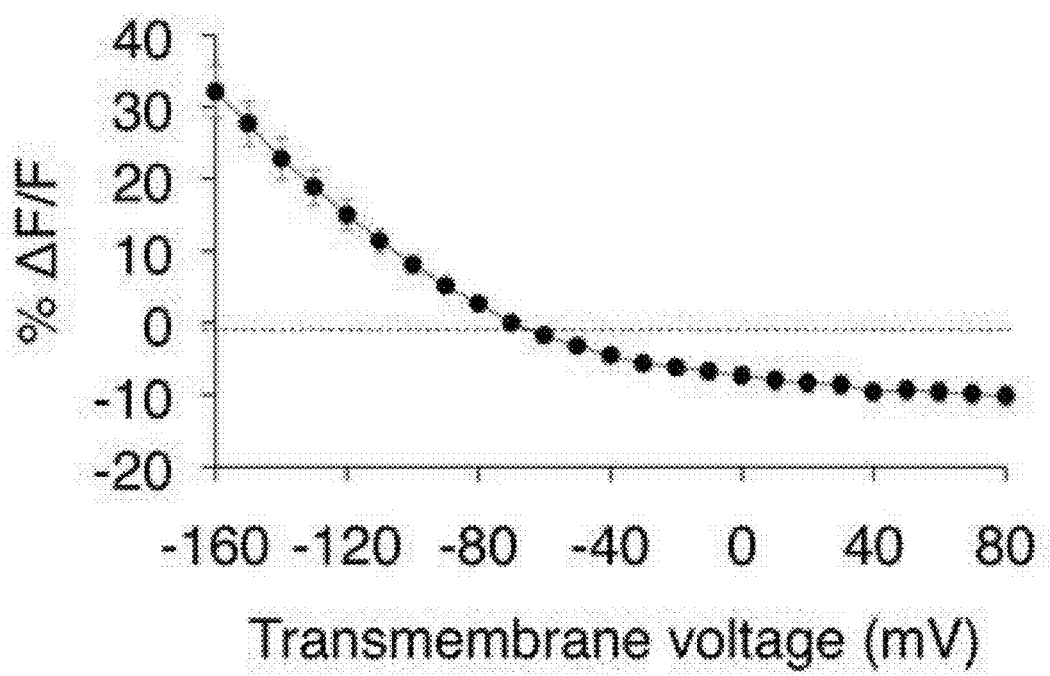

We first demonstrated that ASAP1 produced excellent membrane localization in living dissociated hippocampal neurons and fixed brain slices, both at the cell body and in individual dendrites (FIG. 1B). We next quantified ASAP1's dynamic range and kinetics. When expressed in mammalian cells, ASAP1 responded to voltage steps from −160 to 80 mV with a total fluorescence change (AF/F) of −42.3±5.0% (mean±standard error of the mean (SEM), n=8, FIGS. 1C and 1D). The response to a 100 mV depolarization from a holding potential of −70 mV was −8.6±0.3% AF/F (FIG. 1D), an order of magnitude larger than previous cpGFP-based voltage sensors such as ElectrikPk (Barnett et al. (2012) PLoS One 7:e43454). In mammalian cells at room temperature, ASAP1 had rapid biexponential kinetics, with activation and inactivation characterized by a fast component with time constants of about 2 milliseconds (n=3) (FIG. 1E). The fast component accounted for 60.2±1.2% and 43.7±0.6% of the full activation and deactivation kinetics, respectively. As comparison, we characterized ArcLight Q239, the voltage sensor with the largest fluorescence response to APs of all VSD-based sensors. The fast components of the ASAP1 response for activation and inactivation are 5.8 and 15.9 times as fast as those of ArcLight Q239, respectively, while the slow components were 1.3 and 3.0 times as fast.

Figure 1F:
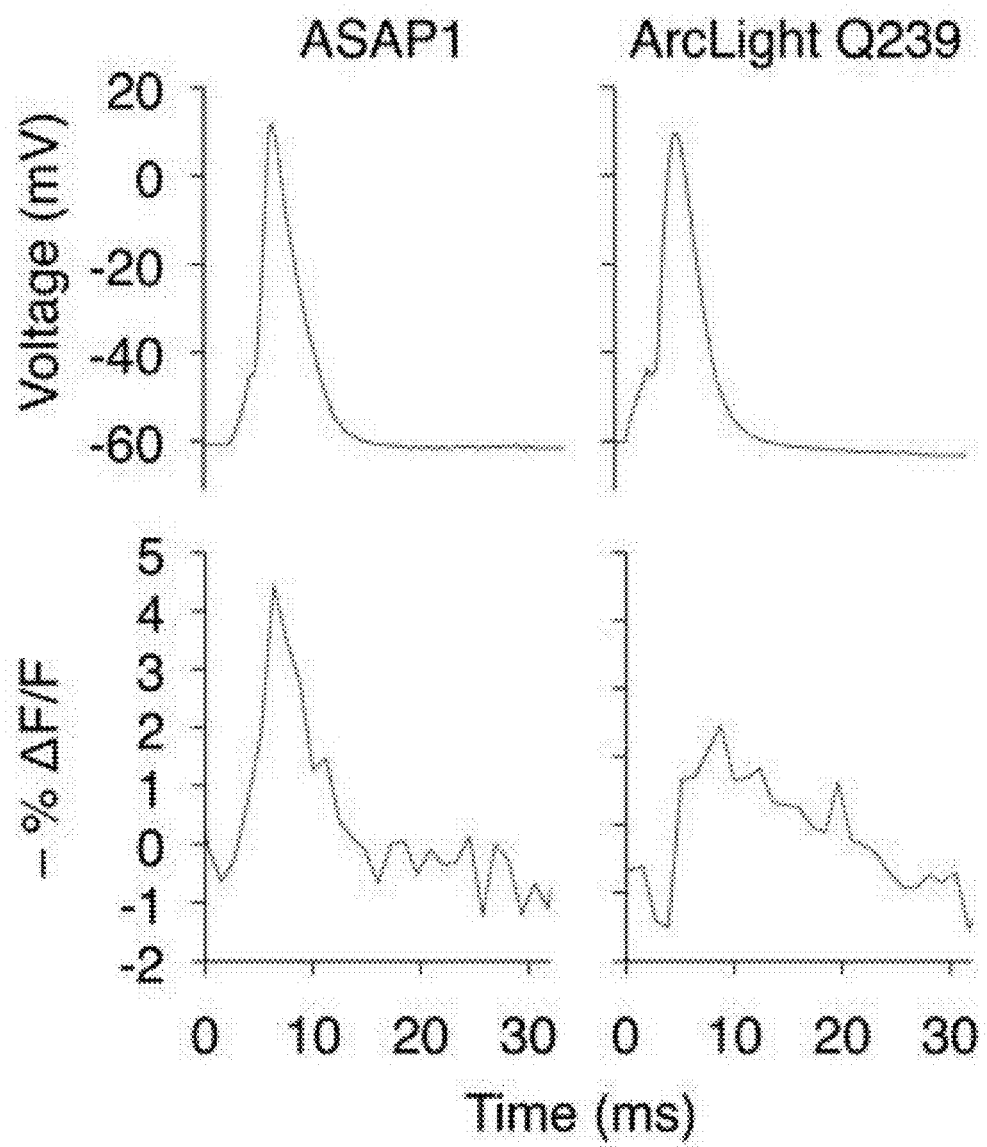
Figure 1G:
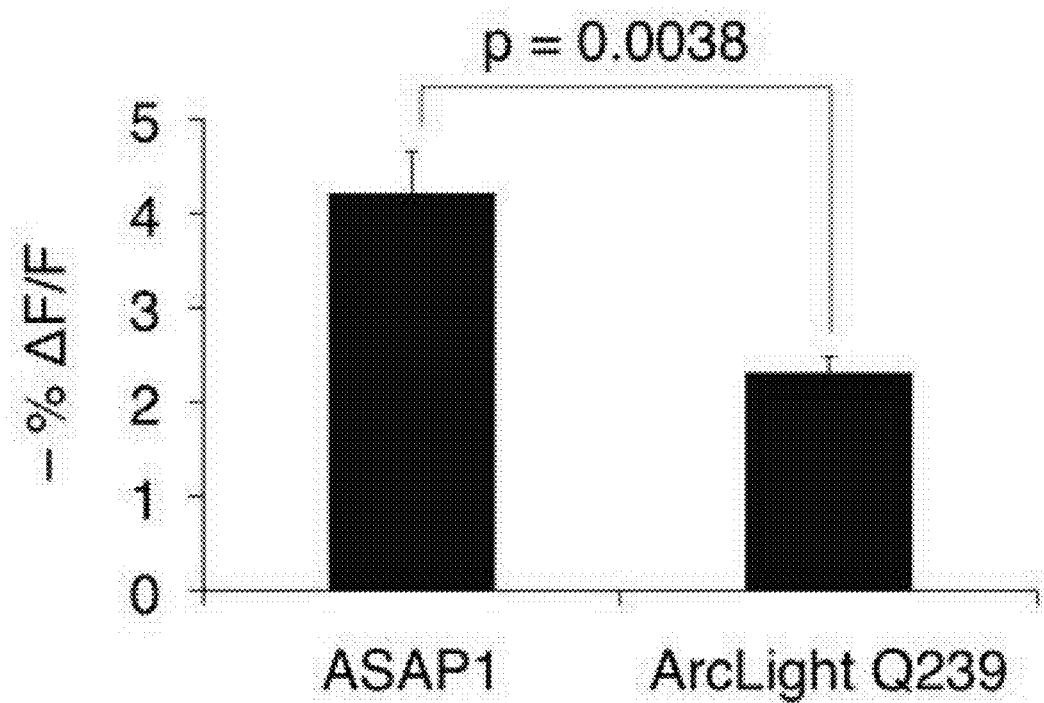

These improved kinetics might help increase the accuracy at which the fluorescence signal matches the measured transmembrane voltage, the amplitude of the fluorescence response to single APs, and the temporal resolution of AP detection with spike trains. Indeed, compared to ArcLight Q239, the fluorescence response of ASAP1 to single APs in cultured hippocampal pyramidal neurons more closely resembles the corresponding voltage response (FIG. 1F). ASAP1 also produces a fluorescence dynamic range (AF/F) of 4.22±0.44% (n=5 cells with 100 APs total), an 83% larger fluorescence change than the 2.31±0.17% we observed with Arclight (n=5 with 87 APs total; p=0.0038) (FIG. 1G). The larger response to single action potentials with ASAP1 is consistent with its 5-fold faster kinetics, which are better matched to the kinetics of action potentials.

Figure 2A:
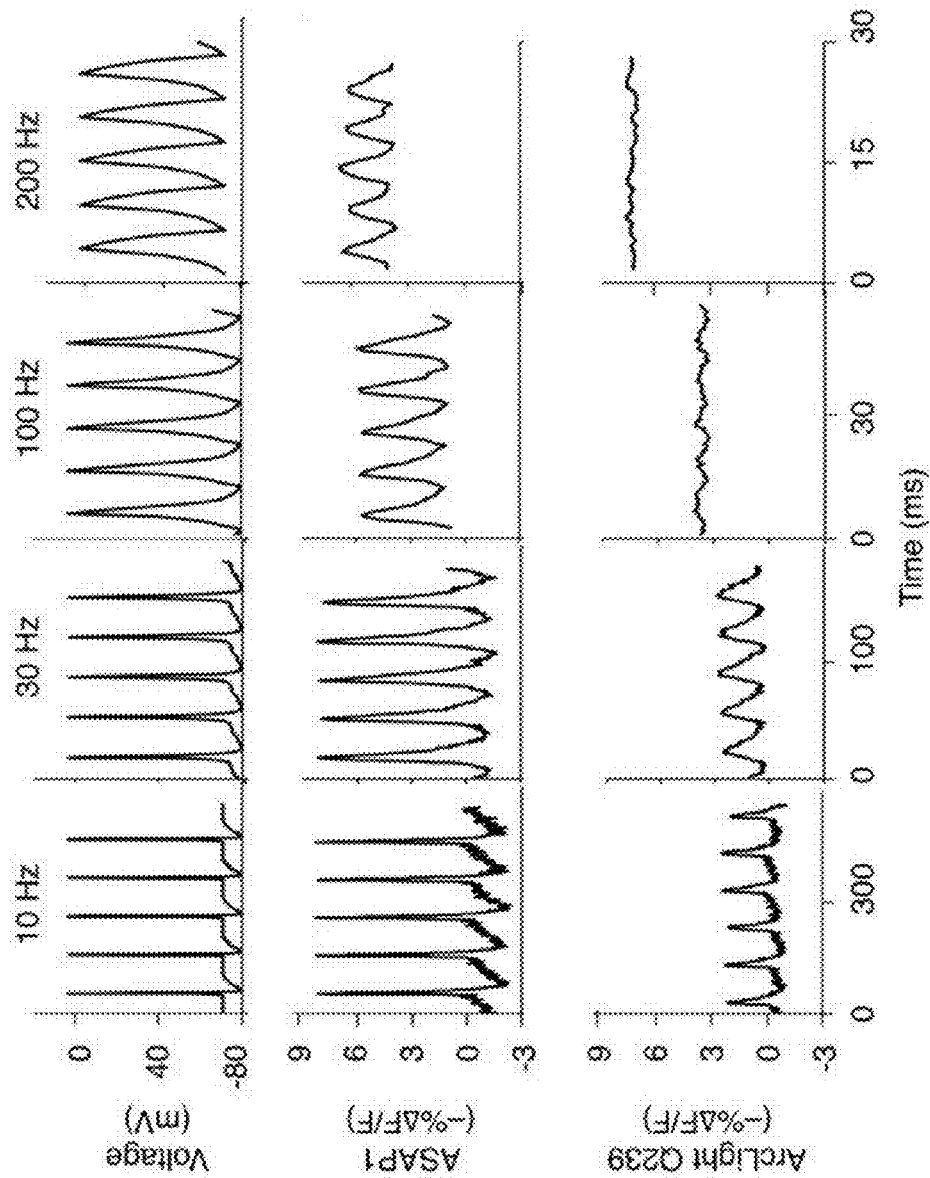
FIGS. 2A-2C show monitoring simulated AP trains and subthreshold potentials in voltage-clamped conditions.
Figure 2B:
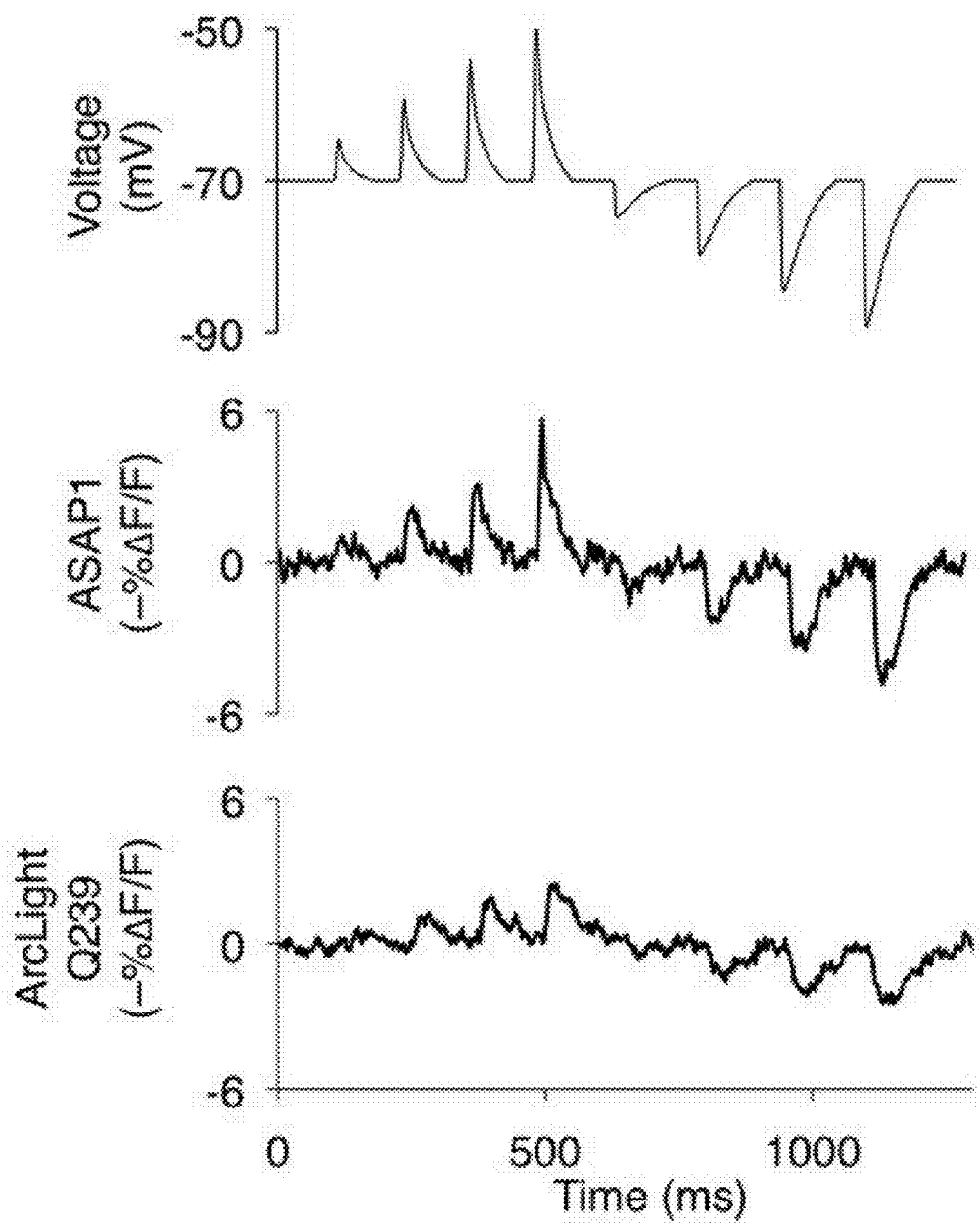
Figure 2C:
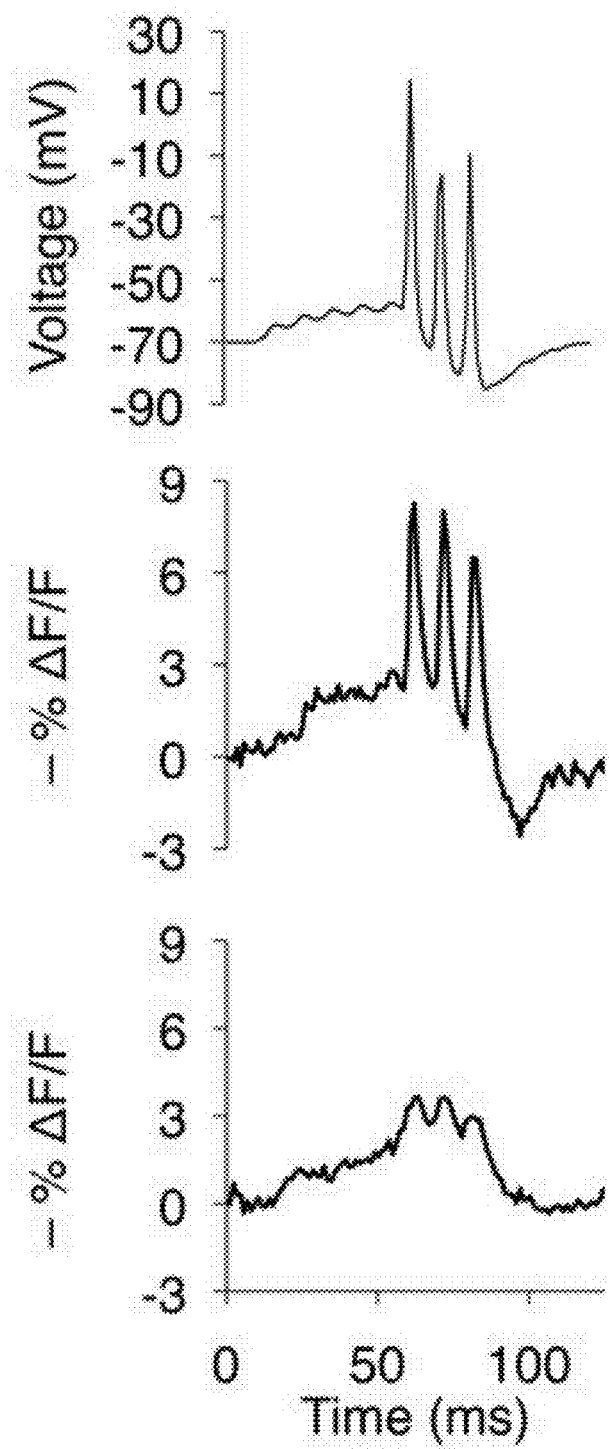
Figure 3A:
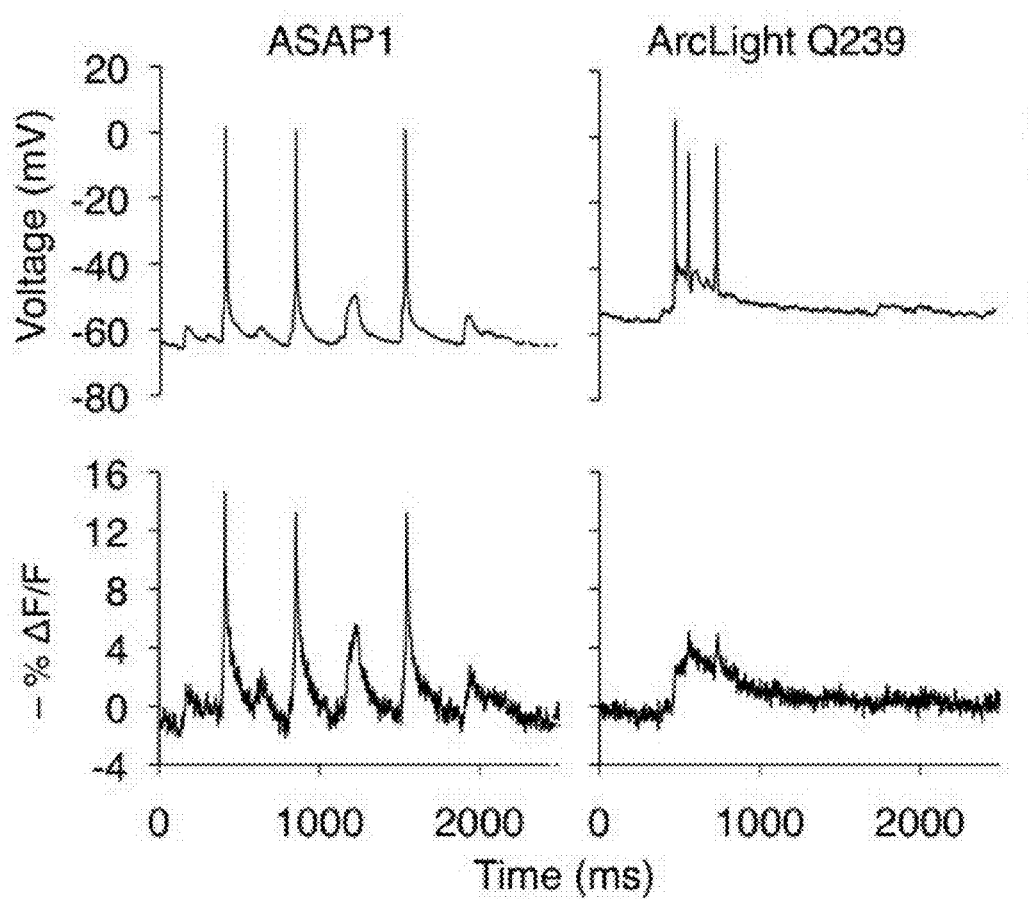
FIGS. 3A-3D show imaging neural activity in dissociated cultures and slices in current-clamped conditions.
Figure 3B:
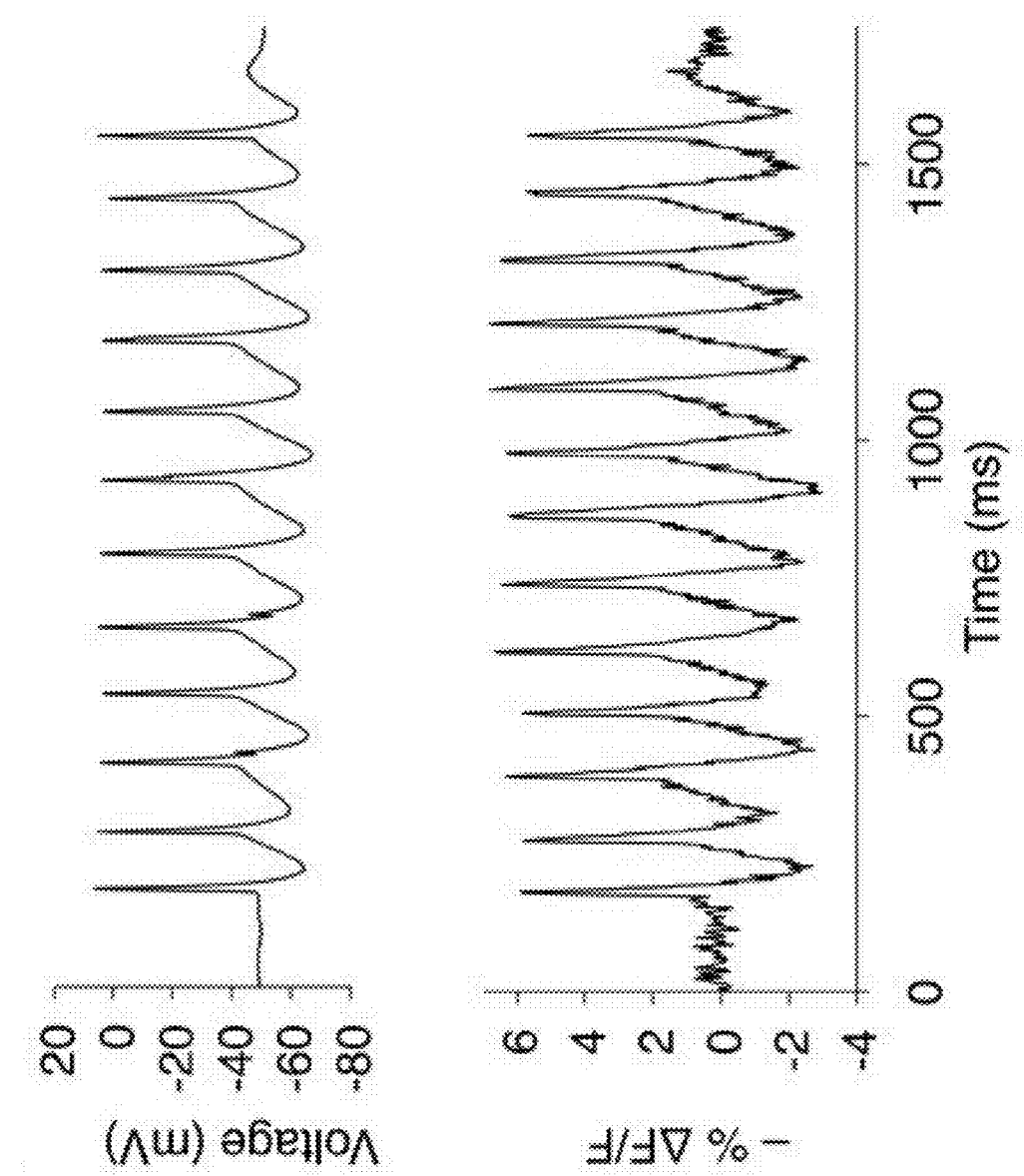
Figure 3C:
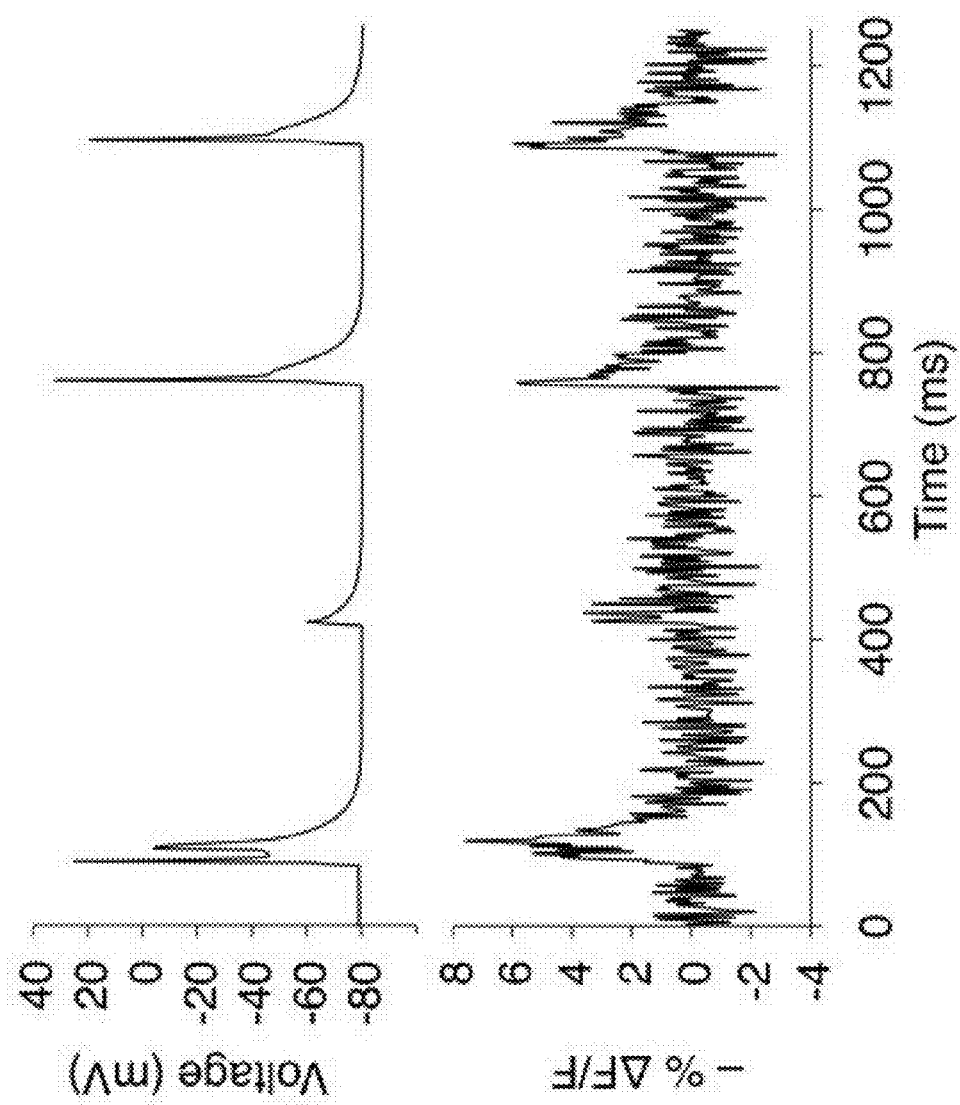
Figure 3D:
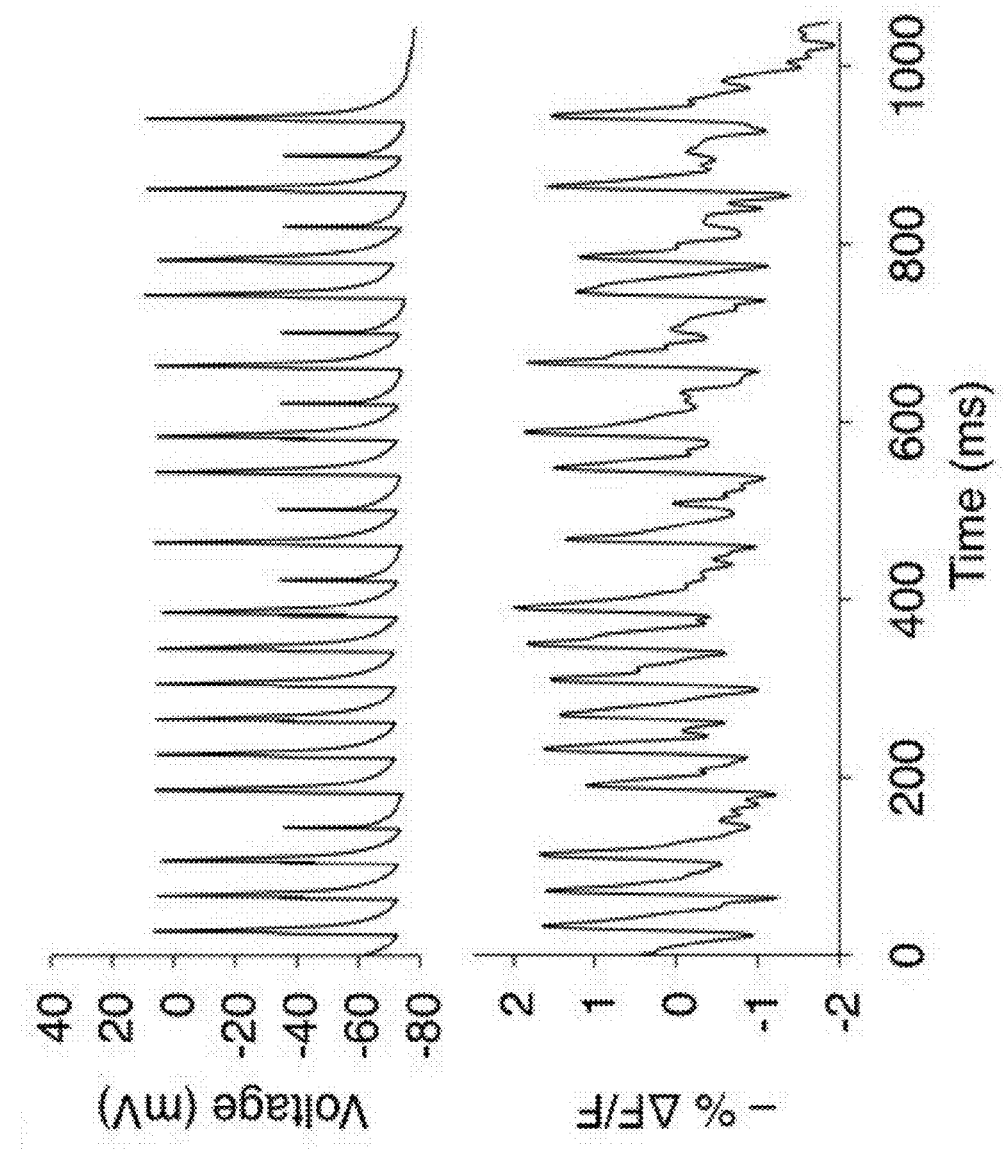

We hypothesized that the fast kinetics and large response of ASAP1 should enable it to track complex waveforms. We tested the ability of ASAP1 to track simulated spike trains of various frequencies in HEK293 cells. ASAP1 was able to track trains up to 200 Hz while clearly discerning individual peaks in single trials without filtering. In contrast, ArcLight Q239 had limited peak discrimination above 30 Hz (FIG. 2A). ASAP1 was able to detect subthreshold depolarizations in neurons in the form of simulated excitatory postsynaptic potentials (EPSPs) and inhibitory postsynaptic potentials (IPSPs) of 5 mV amplitude, similar to ArcLight (FIG. 2B). Interestingly, ASAP1 was able to resolve spikes superimposed on a large EPSP, whereas ArcLight Q239 was not (FIG. 2C). ASAP1 was also able to detect spontaneous EPSPs and spikes (FIG. 3A) and spontaneous 10-Hz bursting (FIG. 3B) in cultured hippocampal pyramidal neurons with accurate tracking of potentials between spikes. Finally, we investigated ASAP1 performance in acute cortical slices from mouse brains transfected in utero. ASAP1 reported current-induced APs in layer 5 pyramidal neurons in single trials without filtering or averaging (FIG. 3C) and was able to distinguish between subthreshold depolarizations and APs. ASAP1 was also to reliably report current-induced 25-Hz AP trains in layer 2/3 neurons (FIG. 3D), again distinguishing between subthreshold depolarizations and APs. Thus, ASAP1 is able to discriminate between subthreshold voltage changes, single action potentials, and closely spaced action potentials in neurons in culture and in brain slices.

The large fluorescence response of ASAP1 to single action potentials and its ability to track high-frequency trains make ASAP1 an excellent sensor for action potential detection and counting, either in unitary events or in trains. It is also able to detect subthreshold voltage changes, and thus is well suited as a general purpose voltage sensor. Compared to other voltage sensor designs, ASAP1 is unique in combining large responses, speed, and brightness, allowing for sensitive detection of membrane voltage changes with standard optical equipment. ASAP1 thus should facilitate efforts to map neuronal activity in the brain.

Methods

Plasmid Construction

Plasmids were constructed by standard molecular biology methods, and were verified by sequencing of all cloned fragments. Plasmids and their complete sequences can be obtained via Addgene (addgene.org/). ArcLight-Q239 (Jin et al. (2012) Neuron 75:779-785) and ASAP1 variants were cloned between the NheI-HindIII sites of pcDNA3.1/Puro-CAG (Lam et al. (2012) Nat. Methods 9:1005-1012; herein incorporated by reference). All variants contain identical Kozak sequences. We constructed a circularly permuted GFP from GCaMP3 (cpGFP145-144_GCaMP3) by inserting amino acids 145-148 ('YNSH') from EGFP into the N terminus of cpGFP149-144 from plasmid pEGFP—N-1-GCaMP3 (Addgene 22692, Tian et al. (2009) Nat. Methods 6:875-881; herein incorporated by reference). Similarly, we constructed cpGFP145-144_GECO1.2 by inserting the same four amino acids from EGFP ('YNSH') to the N terminus of cpGFP149-144 from CMV-GGECO1.2 (Addgene 32446, Zhao et al. (2011) Science 333:1888-1891; herein incorporated by reference). cpsfGFP145-144 is a circular permutant of a superfolder GFP variant evolved for use in a split GFP system, and contains seven mutations ("GFP1-10 OPT" mutations) not present in the original superfolder GFP (Pedelacq et al. (2006) Nat. Biotechnol. 24:79-88; herein incorporated by reference). Voltage sensors encoding cpGFP from GCaMP3, GECO1.2 and sfGFP were cloned in pcDNA3.1/Puro-CAG. To evaluate sensor brightness, we cloned an 'IRESmCherry-CAAX' fragment downstream of the promoter, The Internal Ribosome Entry Site (IRES), originally extracted from encephalomyocarditis virus (EMCV), allows expression of the voltage sensor and mCherry-CAAX from the same promoter (CAG).

HEK293A Cell Culture, Transfection and Imaging

HEK293A cells were maintained in high-glucose Dulbecco's Modified Eagle Medium (DMEM, HyClone) supplemented with 5% fetal bovine serum (FBS, Life Tech) and 2 mM glutamine (Sigma) at 37° C. in air with 5% $CO_2$. Cells were plated onto glass-bottom 24-well plates for standard imaging, or onto uncoated No. 0 12 mm coverslips for patch clamping experiments. Transfections were carried out using FuGene HD (Promega) according to manufacturer instructions, except that cells were transfected at about 50% confluence with lower amounts of DNA (200 ng) and transfection reagent (0.6 μl) to reduce cell toxicity. Cells were cultured for about 48 hours before experiments were performed. For standard imaging without patch-clamping, we used an IX81 microscope with a 60×1.42-numerical aperture (NA) PlanApo oil-immersion objective (Olympus). Fluorescence excitation was delivered using a 120 W Mercury vapor short arc lamp (X-Cite 120PC, Exfo) through a 485/22 nm filter. Fluorescence emission was passed through a 540/40 nm filter, and recorded using an Orca ER CCD (Hamamatsu). For patch-clamp experiments, we used an Axopatch 700B amplifier (Axon Instruments) and borosilicate glass electrodes with resistances of 2.5-5 M. Cells were superfused in a chamber mounted on the stage of an Axiovert 100M inverted microscope (Zeiss) with a 40×1.3-N.A. oil-immersion objective (Zeiss). Fluorescence excitation was delivered using a high-power blue LED (UHP-MIC-LED-460, Pryzmatix) through a 472/30 nm filter at a power density of 0.4-4.7 mW/mm$^2$. Fluorescence emission was passed through a 525/50 nm filter, and recorded using an Andor iXon 860 electron-multiplied charge-coupled device camera cooled to −80° C. For step voltages, we captured images at 40 Hz without binning, and the fluorescence response was measured from pixels at the perimeter (membrane) of the cell (step voltages). For experiments with trains of artificial AP waveforms, we captured images at 827 Hz with 4×4 binning, and fluorescence response was measured using pixels from the entire cell. The action potential waveform, recorded from a hippocampal neuron, has a half-width of 2.0 milliseconds and peak amplitude of 75 mV. Electrophysiological data was recorded with Clampex (Molecular Devices) while fluorescence images were acquired with Solis (Andor).

Determination of Activation and Inactivation Kinetics

To measure the kinetics of ASAP1 and ArcLight-Q239, emission was passed through a 520/40-nm band-pass filter to a PMM02 photomultiplier tube (Thorlabs) and sampled at 5-10 kHz. Double-exponential models were applied to the rising and falling portions of the imaging trace during command step voltages.

Example 2

Performance of ASAP1 Variants as Voltage Sensors

We tested the performance of a variety of ASAP1 variants in which the *Gallus gallus* (chicken)) VSD was replaced with homologous VSDs from other species, including *Danio rerio* (zebrafish), *Xenopus laevis* (African clawed frog), *Alligator mississippiensis* (American alligator), and *Metaseiulus occidentalis* (mite). In addition, we tested an ASAP1 variant in which the circularly permuted GFP was replaced with a circularly permuted variant of mApple, cpmApple151-150, previously described by Zhao et al. (Science (2011) 333:1888-1891; herein incorporated by reference in its entirety).

Polynucleotides encoding the ASAP1 variants, including the *Danio rerio* (SEQ ID NO:15), *Xenopus laevis* (SEQ ID NO:17), *Metaseiulus occidentalis* (SEQ ID NO:16), and cpmApple151-150 (SEQ ID NO:14) ASAP1 variants were cloned into a pcDNA3.1-euro-CAG vector and expressed in HEK293A mammalian cells. Single cells expressing the voltage sensors were patch-clamped and imaged as described in Example 1. Fluorescence excitation was delivered using a Lambda HPX with a "cool white" LED light source (Sutter) through a 550/30 filter. The excitation power at the sample plane was 12.5 mW/mm$^2$. Fluorescence emissions were passed through a 595/30 filter, and imaged at 200 Hz.

Figure 8:
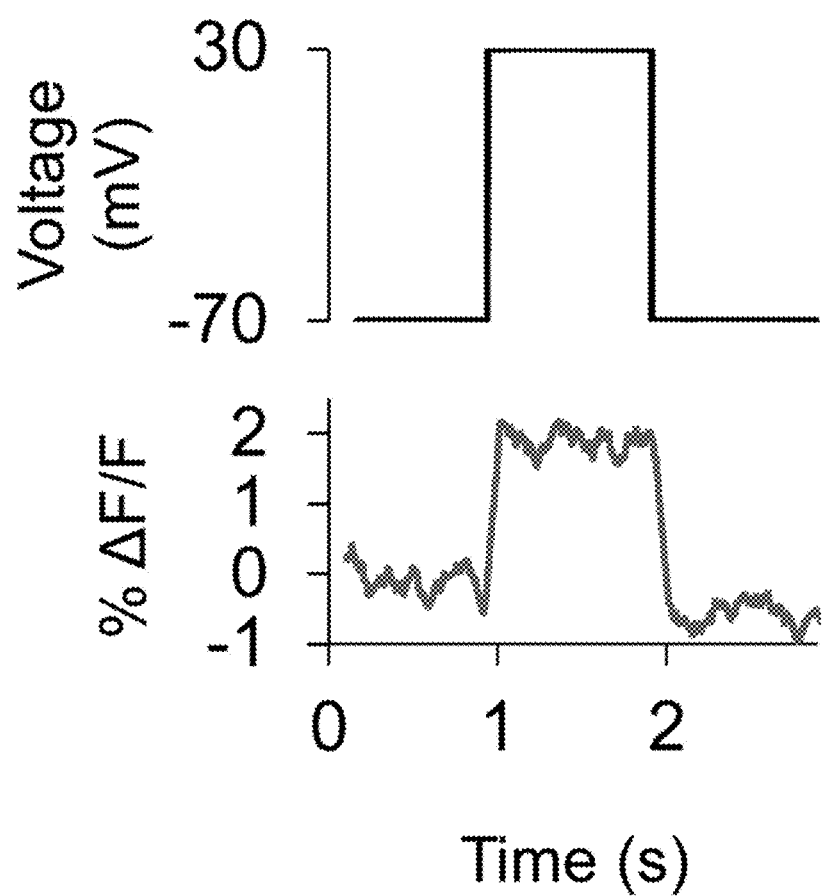
FIG. 8 shows the fluorescence response for the ASAP1 variant comprising cpmApple151-150. The bottom panel shows the fluorescence response of a single mammalian HEK293A cell to a one-second 100 mV voltage pulse.

The fluorescence response for the ASAP1 variant comprising cpmApple151-150 is shown in FIG. 8. The fluorescence response was measured for a single mammalian HEK293A cell expressing the ASAP1 cpmApple151-150 variant. The ASAP1 cpmApple151-150 variant responded to a one-second 100 mV voltage pulse with detectable changes in fluorescence showing that it is functional as a voltage sensor.

Figure 9A:
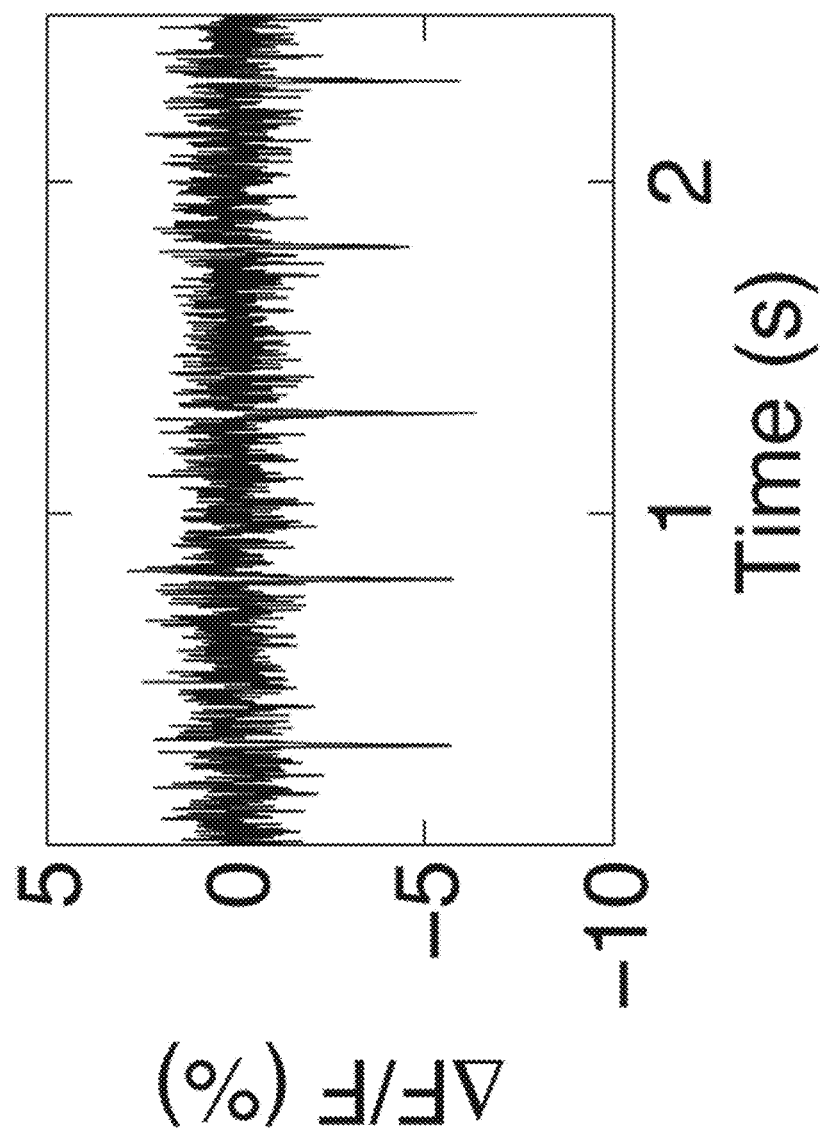
FIGS. 9A-9C show the fluorescence response for the ASAP1 variant comprising a voltage-sensing domain from *Alligator mississippiensis*.
Figure 9B:
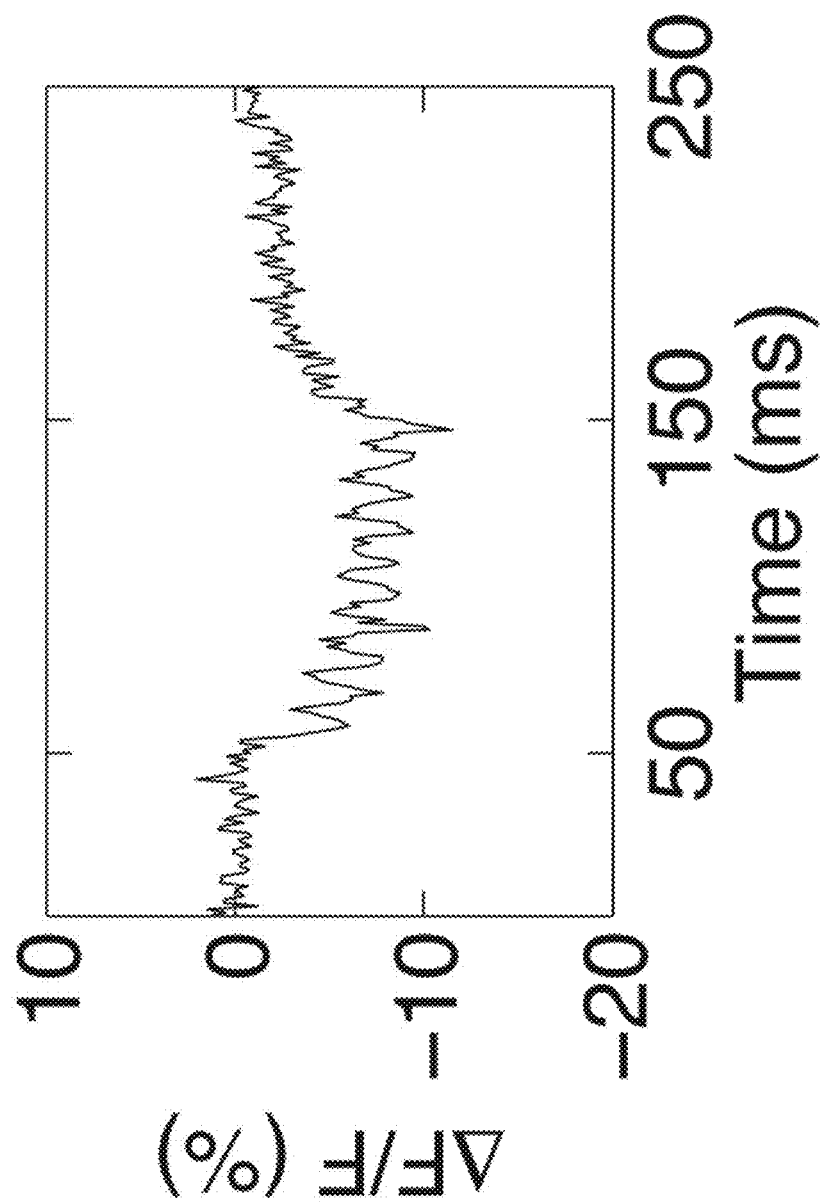
Figure 9C:
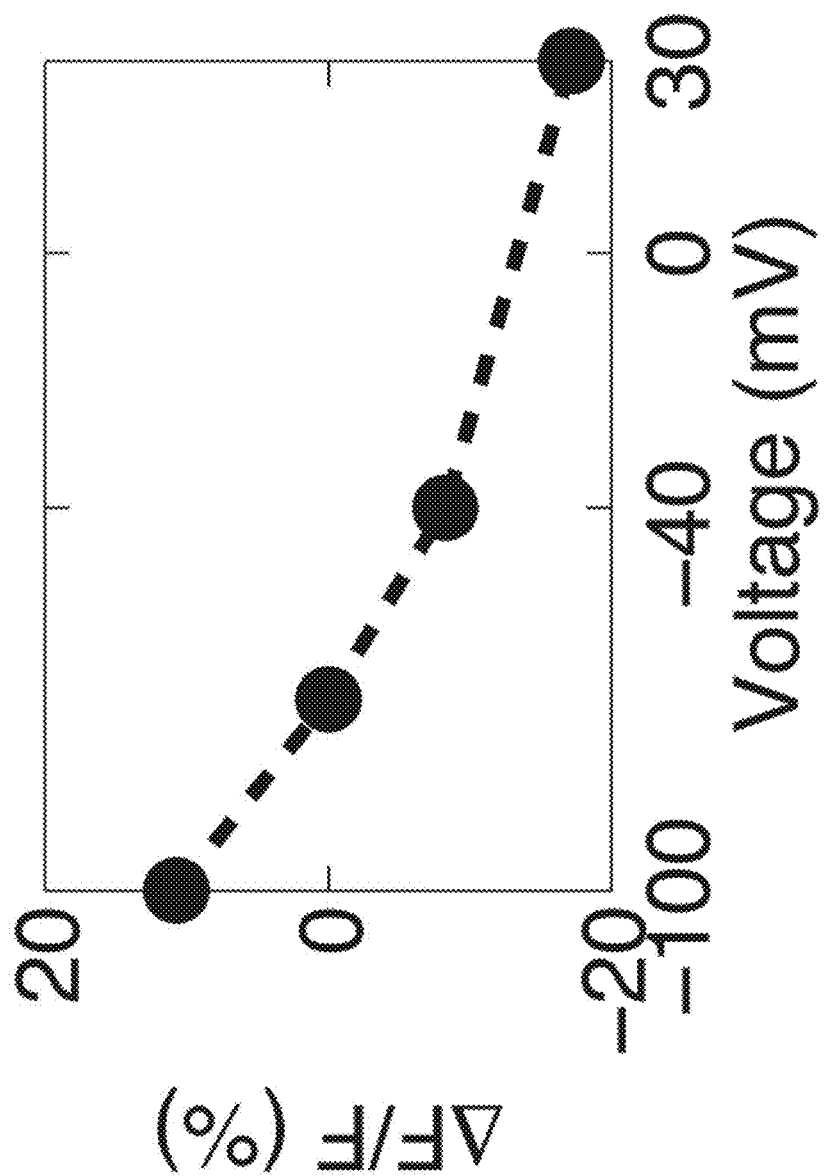
Figure 10A:
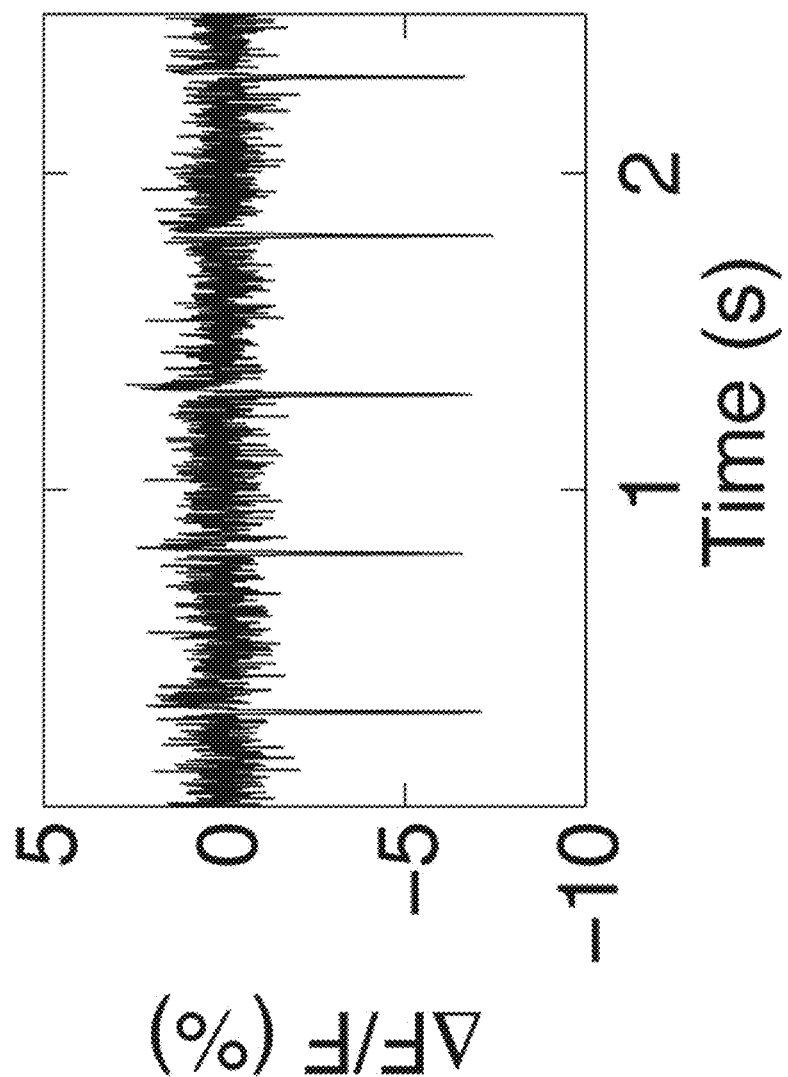
FIGS. 10A-10C show the fluorescence response for the ASAP1 variant comprising a voltage-sensing domain from *Metaseiulus occidentalis*.
Figure 10B:
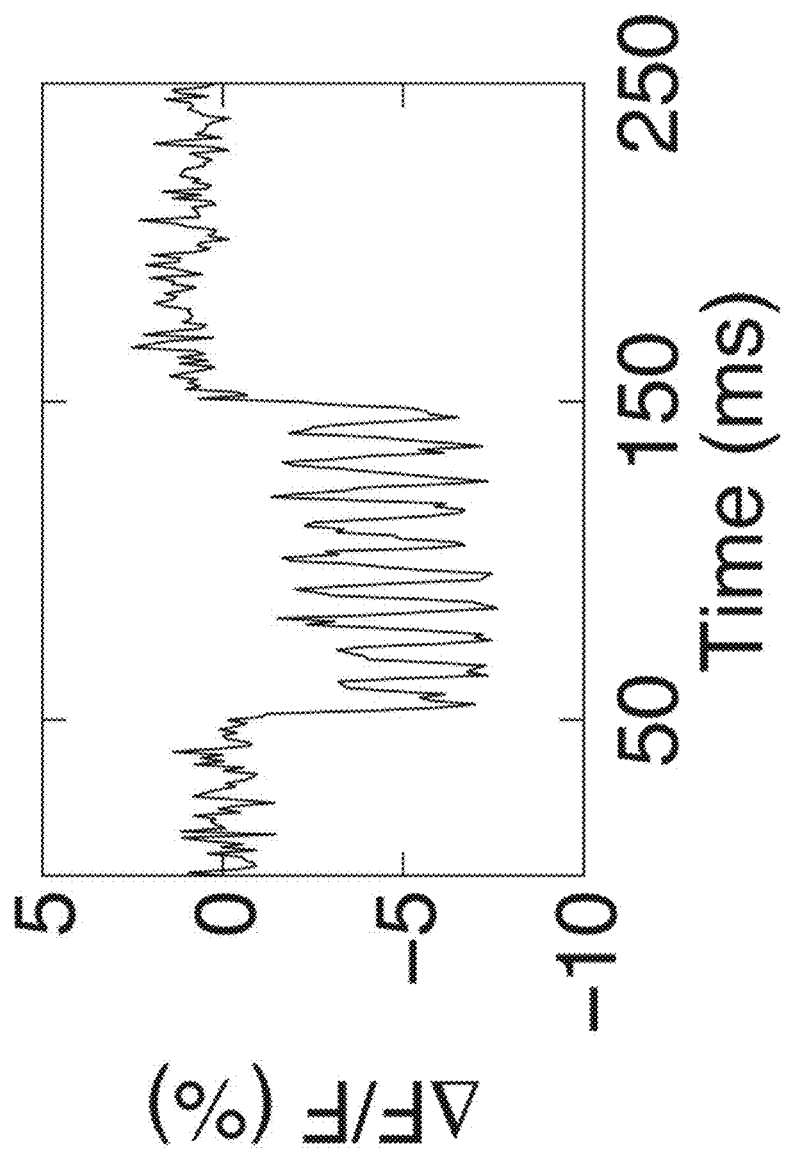
Figure 10C:
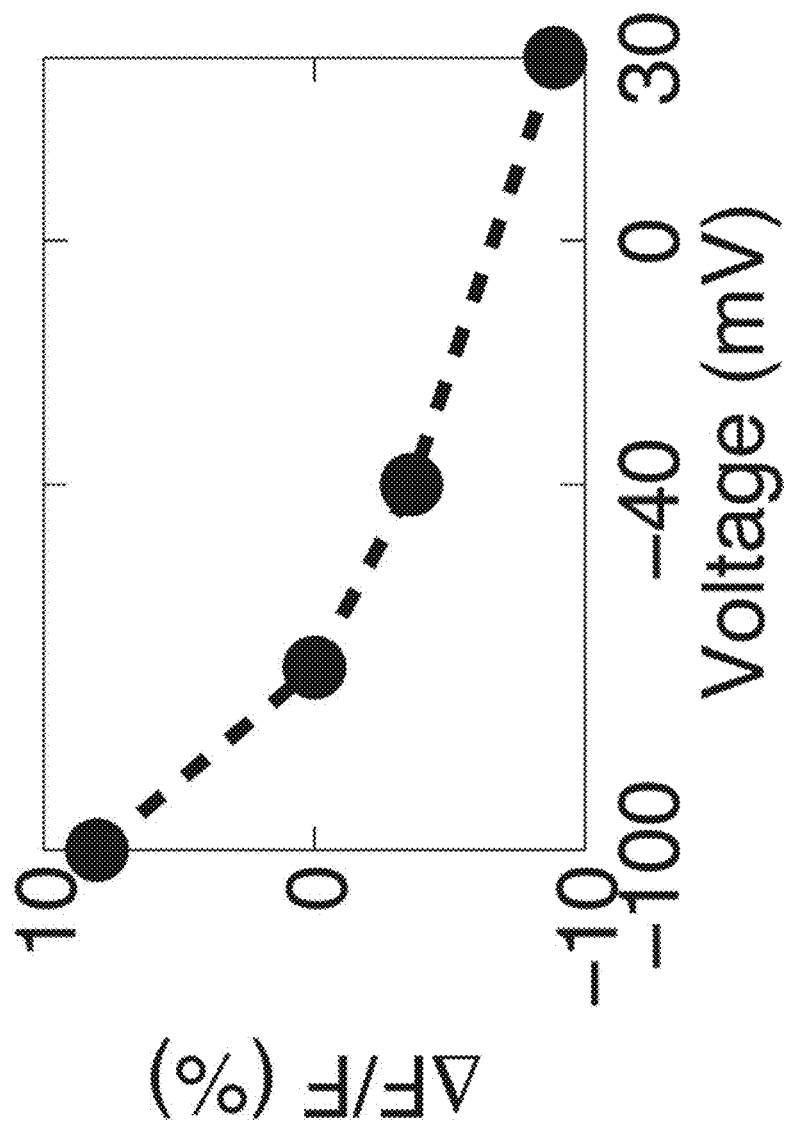

The results of replacing the *Gallus gallus* VSD with homologous VSDs from other species are shown in FIGS. 5A-5C (for ASAP1 variants with the *Xenopus laevis, Danio rerio*, and *Ciona intestinalis* VSDs), FIGS. 9A-9C (for the ASAP1 variant with the *Alligator mississippiensis* VSD), and FIGS. 10A-10C (for the ASAP1 variant with the *Metaseiulus occidentalis* VSD). All of these ASAP1 variants demonstrated voltage-dependent fluorescence responses that will allow them to be used as voltage sensors. The results indicate that voltage sensors can be designed with VSDs from various animal types, including fish, amphibians, reptiles and insects.

Thus, various ASAP1 variants comprising alterations in the VSD or fluorophore can be used as voltage sensors. The choice of VSD and fluorophore may depend on the desired speed, dynamic range, or brightness of the voltage sensor needed for a particular application. Additionally, ASAP1 variants can be designed with different fluorescent proteins to produce voltage sensors with fluorescent emissions at different wavelengths. Such ASAP1 variants can be used in combination for simultaneous monitoring of multiple cells and potentially be used in multiplexed optical monitoring of electrical activity, for example, to distinguish cells in tissues and the behavior of different cell types.

While the preferred embodiments of the invention have been illustrated and described, it will be appreciated that various changes can be made therein without departing from the spirit and scope of the invention.

What is claimed is:

1. A polynucleotide encoding a fluorescent protein voltage sensor comprising: (i) a voltage-sensing domain (VSD) comprising four transmembrane segments; and (ii) a circularly permuted fluorescent protein, wherein the circularly permuted fluorescent protein is inserted into an extracellular loop between the third transmembrane segment (S3) and the fourth transmembrane segment (S4) of the VSD at a position 4, 5, or 6 amino acids downstream of the C-terminal end of the S3.

2. A recombinant polynucleotide comprising the polynucleotide of claim 1 operably linked to a promoter.

3. The recombinant polynucleotide of claim 2, wherein the promoter is a cell-type specific promoter.

4. The recombinant polynucleotide of claim 3, wherein the cell-type specific promoter is a neuron-specific promoter or a cardiac-specific promoter.

5. The recombinant polynucleotide of claim 2 comprising a polynucleotide selected from the group consisting of:
   a) a polynucleotide comprising the nucleotide sequence of SEQ ID NO:12;
   b) a polynucleotide comprising a nucleotide sequence at least 95% identical to the nucleotide sequence of SEQ ID NO:12, wherein the fluorescence intensity of the encoded polypeptide is voltage dependent;
   c) a polynucleotide encoding a polypeptide comprising an amino acid sequence selected from the group consisting of SEQ ID NOS:1-3 and SEQ ID NOS:13-17; and
   d) a polynucleotide encoding a polypeptide comprising a sequence at least 95% identical to an amino acid sequence selected from the group consisting of SEQ ID NOS:1-3 and SEQ ID NOS:13-17, wherein the fluorescence intensity of the polypeptide is voltage dependent.

6. A host cell comprising the recombinant polynucleotide of claim 2.

7. The host cell of claim 6, wherein the host cell is an excitable cell.

8. The host cell of claim 7, wherein the excitable cell is selected from the group consisting of a neuron, a cardiac cell, and an endocrine cell.

9. A method for monitoring the membrane potential of an excitable cell, the method comprising:
   a) transfecting the excitable cell with the recombinant polynucleotide of claim 2, whereby the fluorescent protein voltage sensor is expressed and localizes to a membrane of the cell; and
   b) illuminating the excitable cell with light at an excitation wavelength of the fluorescent protein voltage sensor; and
   c) monitoring the fluorescence response, wherein the intensity of the fluorescence emitted by the fluorescent protein voltage sensor is correlated with the membrane potential of the excitable cell.

10. The method of claim 9, wherein the excitable cell is transfected in vitro or in vivo.

11. The method of claim 9, wherein the membrane is a plasma membrane or an organelle membrane.

12. The method of claim 9, wherein the fluorescence response is monitored after exposing the excitable cell to a stimulus.

13. The method of claim 12, wherein the stimulus is selected from the group consisting of an electrical current, a drug, a ligand for a receptor, a ligand for an ion channel, a ligand for an ion transporter, a hormone, and a second messenger.

14. The method of claim 9, wherein changes in the intensity of the fluorescence emitted by the fluorescent protein voltage sensor indicate depolarization.

15. The method of claim 9, wherein monitoring the fluorescence response comprises performing fluorescence microscopy.

16. The method of claim 15, wherein fluorescence microscopy is performed using confocal microscopy, two-photon excitation microscopy, light sheet microscopy, or light-field microscopy.

17. The method of claim 9, wherein the excitable cell is selected from the group consisting of a neuron, a cardiac cell, and an endocrine cell.

18. The method of claim 17, wherein the fluorescent protein voltage sensor localizes to the plasma membrane of a cell body, dendrite, or axon of the neuron or the sarcolemma of the cardiac cell.

19. The method of claim 9, wherein monitoring the fluorescence response comprises detecting a single action potential.

20. The method of claim 9, wherein monitoring the fluorescence response comprises detecting a subthreshold potential change.

21. The method of claim 20, wherein the subthreshold potential change is an excitatory postsynaptic potential (EPSP) or an inhibitory postsynaptic potential (IPSP).

22. The method of claim 9, wherein monitoring the fluorescence response comprises detecting depolarization or hyperpolarization.

23. The method of claim 9, wherein monitoring the fluorescence response comprises detecting a train of action potentials.

24. The method of claim 23, wherein the action potential waveform has a frequency of up to 200 Hz.

25. A method for monitoring the membrane potential of an excitable cell, the method comprising:
   a) inserting the fluorescent protein voltage sensor encoded by the polynucleotide of claim 1 into a membrane of the excitable cell; and
   b) illuminating the excitable cell with light at an excitation wavelength of the fluorescent protein voltage sensor; and
   c) monitoring the fluorescence response, wherein the intensity of the fluorescence emitted by the fluorescent protein voltage sensor is correlated with the membrane potential of the excitable cell.

26. The method of claim 25, wherein the membrane is a plasma membrane or an organelle membrane.

27. The method of claim 25, wherein the fluorescence response is monitored after exposing the excitable cell to a stimulus.

28. The method of claim 27, wherein the stimulus is selected from the group consisting of an electrical current, a drug, a ligand for a receptor, a ligand for an ion channel, a ligand for an ion transporter, a hormone, and a second messenger.

29. The method of claim 25, wherein changes in the intensity of the fluorescence emitted by the fluorescent protein voltage sensor indicate depolarization.

30. The method of claim 25, wherein monitoring the fluorescence response comprises performing fluorescence microscopy.

31. The method of claim 30, wherein fluorescence microscopy is performed using confocal microscopy, two-photon excitation microscopy, light sheet microscopy, or light-field microscopy.

32. The method of claim 25, wherein the excitable cell is selected from the group consisting of a neuron, a cardiac cell, and an endocrine cell.

33. The method of claim 32, wherein the fluorescent protein voltage sensor localizes to the plasma membrane of a cell body, dendrite, axon of the neuron or the sarcolemma of the cardiac cell.

34. The method of claim 25, wherein monitoring the fluorescence response comprises detecting a single action potential.

35. The method of claim 25, wherein monitoring the fluorescence response comprises detecting a subthreshold potential change.

36. The method of claim 35, wherein the subthreshold potential change is an excitatory postsynaptic potential (EPSP) or an inhibitory postsynaptic potential (IPSP).

37. The method of claim 25, wherein monitoring the fluorescence response comprises detecting depolarization or hyperpolarization.

38. The method of claim 25, wherein monitoring the fluorescence response comprises detecting a train of action potentials.

39. The method of claim 38, wherein the action potential waveform has a frequency of up to 200 Hz.

40. A method of screening an agent for its effect on the membrane potential of an excitable cell, the method comprising:
   a) monitoring the membrane potential of the excitable cell, according to the method of claim 9, before and after treatment of the excitable cell with the agent; and
   b) comparing the membrane potential before and after treatment of the cell with the agent to detect any changes in the membrane potential resulting from treatment of the excitable cell with the agent.

41. The method of claim 40, wherein the agent is an ion channel modulator, an ion channel blocker, an ion channel opener, a ligand for an ion channel, a ligand for an ion transporter, a ligand for a receptor, a hormone, or a second messenger.

42. A method of screening an agent for its effect on the membrane potential of an excitable cell, the method comprising:
   a) monitoring the membrane potential of the excitable cell, according to the method of claim 25, before and after treatment of the excitable cell with the agent; and
   b) comparing the membrane potential before and after treatment of the excitable cell with the agent to detect any changes in the membrane potential resulting from treatment of the excitable cell with the agent.

43. The method of claim 42, wherein the agent is an ion channel modulator, an ion channel blocker, an ion channel opener, a ligand for an ion channel, a ligand for an ion transporter, a ligand for a receptor, a hormone, or a second messenger.

44. A method for producing a fluorescent protein voltage sensor, the method comprising:
   a) transforming a host cell with the recombinant polynucleotide of claim 2;
   b) culturing the transformed host cell under conditions whereby the fluorescent protein voltage sensor is expressed; and
   c) isolating the fluorescent protein voltage sensor from the host cell.

45. A kit comprising the recombinant polynucleotide of claim 2.

46. A kit comprising the host cell of claim 6.

47. The polynucleotide of claim 1, wherein the VSD is from a voltage sensitive phosphatase.

48. The polynucleotide of claim 1, wherein the voltage sensitive phosphatase is from a bird, a fish, an amphibian, a reptile, or an insect.

49. The polynucleotide of claim 48, wherein the voltage sensitive phosphatase is from *Gallus gallus, Xenopus laevis, Danio rerio, Alligator mississippiensis*, or *Metaseiulus occidentalis*.

50. The polynucleotide of claim 1, wherein the VSD is from a voltage-gated ion channel or transporter.

51. The polynucleotide of claim 1, wherein the VSD comprises a mutation comprising a substitution of a glutamine for the amino acid at the position corresponding to 153 numbered relative to the reference sequence of SEQ ID NO:4.

52. The polynucleotide of claim 1, wherein the circularly permuted fluorescent protein emits green, blue, cyan, yellow, orange, red, or far-red light.

53. The polynucleotide of claim 1, wherein the circularly permuted fluorescent protein is selected from the group consisting of circularly permuted green fluorescent protein (cpGFP), circularly permuted superfolder GFP (cpsfGFP), circularly permuted mApple (cpmApple), circularly permuted mCherry (cpmCherry), circularly permuted mKate (cpmKate), circularly permuted enhanced green fluorescent protein (cpEGFP), circularly permuted Venus (cpVenus), circularly permuted Citrine (cpCitrine), and circularly permuted enhanced yellow fluorescent protein (cpEYFP).

54. The polynucleotide of claim 53, wherein the circularly permuted fluorescent protein is cpsfGFP or cpmApple.

55. The polynucleotide of claim 1, wherein the polynucleotide is selected from the group consisting of:
a) a polynucleotide encoding a polypeptide comprising an amino acid sequence selected from the group consisting of SEQ ID NOS:1-3 and SEQ ID NOS:13-17; and
b) a polynucleotide encoding a polypeptide comprising an amino acid sequence having at least 95% identity to an amino acid sequence selected from the group consisting of SEQ ID NOS:1-3 and SEQ ID NOS:13-17, wherein the fluorescence intensity of the polypeptide is voltage dependent.

56. The polynucleotide of claim 1, wherein the VSD comprises a polypeptide selected from the group consisting of:
a) a polypeptide comprising an amino acid sequence selected from the group consisting of SEQ ID NO:4, SEQ ID NO:19, and SEQ ID NO:20; and
b) a polypeptide comprising an amino acid sequence having at least 95% identity to an amino acid sequence selected from the group consisting of SEQ ID NO:4, SEQ ID NO:19, and SEQ ID NO:20, wherein the polypeptide has voltage sensing characteristics.

57. The polynucleotide of claim 1, wherein the circularly permuted fluorescent protein comprises a polypeptide selected from the group consisting of:
a) a polypeptide comprising an amino acid sequence selected from the group consisting of SEQ ID NO:5 and SEQ ID NO:18; and
b) a polypeptide comprising an amino acid sequence having at least 95% identity to an amino acid sequence selected from the group consisting of SEQ ID NO:5 and SEQ ID NO:18, wherein the fluorescence intensity of the fluorescent protein voltage sensor is voltage dependent.

58. The polynucleotide of claim 1, wherein the fluorescent protein voltage sensor further comprises a targeting sequence.

59. The polynucleotide of claim 58, wherein the targeting sequence is a membrane-targeting sequence or an organelle-targeting sequence.

60. The polynucleotide of claim 59, wherein the membrane-targeting sequence is a prenylation sequence or a signal peptide.

61. The polynucleotide of claim 59, wherein the targeting sequence localizes the fluorescent protein to a subcellular region of a cell.

62. The polynucleotide of claim 1, wherein the circularly permuted fluorescent protein is inserted after the amino acid at the position corresponding to 147, 148, or 149 numbered relative to the reference sequence of SEQ ID NO:3.

* * * * *